(12) United States Patent
Pascal et al.

(10) Patent No.: US 6,239,130 B1
(45) Date of Patent: May 29, 2001

(54) PHOSPHODIESTERASE 4-INHIBITING DIAZEPINOINDOLONES

(75) Inventors: Yves Pascal, Rueil Malmaison; Catherine Burnouf, Ste Grenevieve-des-Bois; Bernard Gaudilliere, Nanterre; Henry Jacobelli, Paray Vieille Poste, all of (FR); Alain Calvet, Ann Arbor, MI (US); Adrian Payne, Westerham (GB); Svein Dahl, Tromsdalen (NO)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/380,883

(22) PCT Filed: Apr. 30, 1998

(86) PCT No.: PCT/EP98/02827

§ 371 Date: Nov. 10, 1999

§ 102(e) Date: Nov. 10, 1999

(87) PCT Pub. No.: WO98/49169

PCT Pub. Date: Nov. 5, 1998

(30) Foreign Application Priority Data

Apr. 30, 1997 (FR) ................................. 97 05422

(51) Int. Cl.[7] ................. C07D 487/06; C07D 519/00; A61K 31/55

(52) U.S. Cl. ............................. 514/220; 540/496

(58) Field of Search ............................. 540/496; 514/220

(56) References Cited

FOREIGN PATENT DOCUMENTS

WO 96/11690 * 4/1996 (WO).

* cited by examiner

*Primary Examiner*—Bruck Kifle
(74) *Attorney, Agent, or Firm*—Charles W. Ashbrook

(57) ABSTRACT

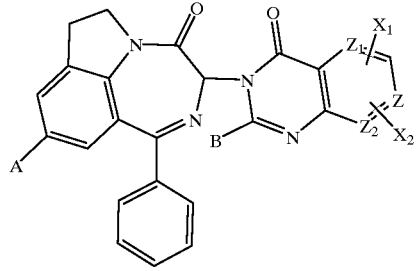

The present invention presents compounds that inhibit phosphodiesterase 4 having Formula (I). The present invention also provides methods of using the compounds of Formula (I) to prevent or treat asthma, atopic dermatitis, rheumatoid arthritis, inflammatory bowel disorders, pulmonary hypertension, liver injury, bone loss, septic shock, or multiple sclerosis, and to pharmaceutical compositions that contain the compounds of Formula (I).

24 Claims, No Drawings

PHOSPHODIESTERASE 4-INHIBITING DIAZEPINOINDOLONES

FIELD OF THE INVENTION

The present invention relates to new [1,4]diazepino[6,7, 1-hi]indol-4-ones which are useful for the preparation of medicaments that enable complaints which are amenable to therapy by a phosphodiesterase 4 inhibitor to be treated. These medicaments are useful, in particular, as anti-inflammatories, anti-allergics, bronchodilators or anti-asthmatics and are bereft of digestive or cardiac side-effects. Conditions also amenable to treatment with a compound according to the invention include inflammatory bowel diseases like ulcerative colitis and Crohn's disease, disorders characterized by a significant increase of TNF-α, such as pulmonary hypertension (primary or secondary), liver failure in particular following immunologic or inflammatory hepatic injury, bone loss (osteoporosis or osteomalacia), septic shock, and multiple sclerosis.

TECHNOLOGICAL BACKGROUND OF THE INVENTION

Cyclic adenosine 3',5'-monophosphate (cAMP) is a ubiquitous intracellular second messenger, intermediate between a first messenger (hormone, neurotransmitter or autacoid) and the cellular functional responses: the first messenger stimulates the enzyme responsible for cAMP synthesis; cAMP then participates, depending on the cells in question, in a very large number of functions: metabolic, contractile or secretory.

The effects of cAMP come to an end when it is degraded by the cyclic nucleotide phosphodiesterases, intracellular enzymes which catalyze its hydrolysis to inactive adenosine 5'-monophosphate.

In mammals, at least seven types of cyclic nucleotide phosphodiesterases (PDE) are distinguished, numbered from 1 to 7 according to their structure, their kinetic behavior, their substrate specificity or their sensitivity to effectors (Beavo J. A. et al. (1990) Trends Pharmacol. Sci. 11, 150–155. Beavo J. A. et al. (1994) Molecular Pharmacol. 46, 399–405). The distribution of these different types varies according to the tissues.

Accordingly, a specific inhibitor of one type of PDE isoenzyme should bring about an increase in the cAMP only in the cells in which this type of enzyme is to be found.

An increase in the cAMP in the leukocytes involved in inflammation inhibits their activation: inhibition of the synthesis and release of mediators in the mast cells, monocytes, eosinophilic and basophilic polynuclear leukocytes, inhibition of neutrophilic and eosinophilic polynuclear leukocyte chemotaxis and degranulation, inhibition of lymphocyte division and differentiation. Among these mediators, the cytokines, in particular (tumor necrosis factor)TNF-α and interleukins, produced by the T lymphocytes and eosinophilic polynuclear leukocytes play an important part in the triggering of inflammatory manifestations, especially in response to stimulation by an allergen in the airways. Furthermore, cAMP decreases the tonus of the smooth muscle fibers of the airways.

In these cells and these tissues, the PDE4 enzymes play an important part in the hydrolysis of cAMP. Selective PDE4 inhibitors can hence be expected to possess therapeutic activity as anti-inflamnnatory, antiallergic and bronchodilatory medicaments, and in the treatment of asthma where an infiltration of the airways by inflammatory cells and bronchoconstriction are observed. Asthma is a frequent and often severe condition. While mortality trends for other medical conditions amenable to treatment have declined in recent decades, asthma has become more prevalent, more severe and more deadly, despite the availability of improved pharmacotherapy to treat it (Lang D. M., Ann. Allergy Asthma Immunol ,1997; 78: 333–7.) Prevalence is especially high in children, which makes the availability of an oral treatment highly desirable.

For some years, extensive research has been carried out in order to obtain and develop potent PDE4 inhibitors. This proves difficult on account of the fact that many potential PDE4 inhibitors are not without activity with respect to the phosphodiesterases of the other families.

The level of activity and of selectivity of PDE4 inhibitors represents a considerable problem in view of the range of flnctions which are regulated by cAMP. There hence exists a need for potent and selective PDE4 inhibitors, that is to say ones that have no action with respect to the PDEs belonging to other families. The international Patent Application published under No. WO 96 11690 describes the application of diazepinoindolone derivatives of formula

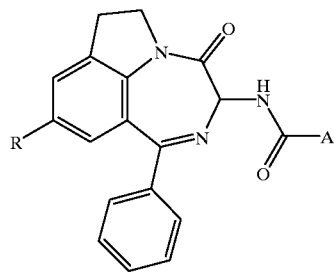

in which R is hydrogen, lower alkyl or lower alkoxy and A is an optionally substituted aromatic ring system, for the preparation of medicaments intended for the treatment of complaints which are amenable to a phosphodiesterase 4 inhibitor. International Application WO 97/36905 describes diazepinoindoles of formula

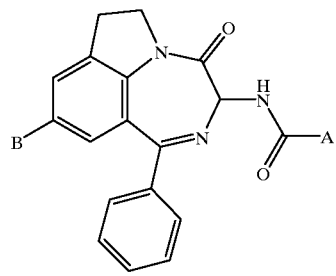

in which A is aryl or nitrogenous heteroaryl, optionally substituted; B is a hydroxyl or amino radical which is itself optionally substituted. These products are useful for treating complaints which are amenable to therapy by the inhibition of PDE4.

The search for potent and selective PDE4 inhibitors remains a major objective for the treatment of pathologies in which the PDE4 enzymes are involved.

SUMMARY OF THE INVENTION

The present invention provides new [1,4]diazepino[6,7, 1-hi]indol-4-one derivatives, which are very potent PDE4 inhibitors, at concentrations at which they have no action on the other PDE families. The invention relates to the diazepinoindolones (I) of formula

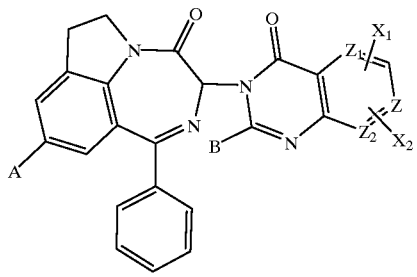

in which:

A is hydrogen, $C_1$–$C_4$alkyl, $OR^1$, hydroxy, nitro, cyano, —$NH_2$, —$NHR^1$, or —$NR^1R^2$;

$R^1$ and $R^2$ independently are $C_1$–$C_4$alkyl, cyclopropyl, cyclopropylmethyl, or $NR^1R^2$ taken together with the nitrogen to which they are bound complete a ring having 4 or 5 carbon atoms;

B is hydrogen, $C_1$–$C_4$alkyl, —$CH_2OM$, —$CH_2OC(=O)$ $(CH_2)_a(CO)_bY^1$–$Y^2$, or —$(CH_2)_cC(=O)OM$;

$Y^1$ is —$(VCH_2CH_2)_c$—, with V=—NH— or —O—; or
$Y^1$ is —$NHCHR^A$—$C(=O)$—;

$Y^2$ is hydrogen, hydroxy, —$OCH_3$, or 4-morpholinyl;

M is hydrogen or $C_1$–$C_4$alkyl;

a=1 or 2; b=0 or 1; c=0, 1, or 2;

Z is CH, then $Z_1$ and $Z_2$ both are CH or N; or

Z is N, then $Z_1$ and $Z_2$ are CH;

$X_1$ and $X_2$ independently are hydrogen, $C_1$–$C_4$alkyl, —$(CH_2)_n$—OR, halogen, cyano,

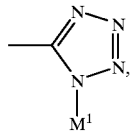

—O—$C_1$–$C_6$alkyl, —$C(=O)R^3$, $C(=O)OR^3$,—$C(=O)$ $NR^4R^3$, or

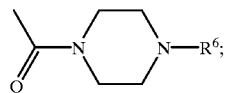

$R^3$ is hydrogen, $C_1$–$C_6$alkyl, benzyl, phenethyl, or —$Q^1$–$Q^2$;

$R^4$ is hydrogen, or $C_1$–$C_4$alkyl;

$R^5$ is hydrogen, $C_1$–$C_4$alkyl, —$CHR^A$—$C(=O)OM^1$, or —$Q^3$–$Q^4$, $R^6$ is hydrogen, $C_1$–$C_4$alkyl, or —$Q^3$–$Q^5$;

$R^A$ is a residue of a natural α-amino-acid, the carbon atom to which it is linked having either a S configuration, or a R configuration;

$Q^1$ is —$(CH_2)_n$—$(CHOH)_m$—$(CH_2)_p$—;

$Q^2$ is hydroxy, —O—$C_1$–$C_6$alkyl, —$OC(=O)$— $C_1$–$C_6$alkyl, or 4-morpholinyl;

$Q^3$ is —$(CH_2)_n$—;

$Q^4$ is —$NHM^1$, —$NM^1M^2$, or 4-morpholinyl;

$Q^5$ is —$M^1$ or —$OM^1$;

$M^1$ and $M^2$ are independently hydrogen or $C_1$–$C_4$alkyl;

n is 1,2, or 3; m is 0, 1, 2, 3, or 4; p is 0, 1, 2, or 3, provided that if m is not 0, then p is not 0;

their racemic forms and each of their isomers, in particular those whose configuration is determined by carbon 3 of the [1,4]diazepino[6,7,1-hi]-indol-4-one ring system, and the pharmaceutically acceptable salts, solvates, esters, amides, and prodrugs thereof.

The invention also relates to a process for preparing them and to their application for obtaining medicaments intended for treating complaints which are amenable to therapy by the inhibition of PDE4.

DETAILED DESCRIPTION OF THE INVENTION

The invention relates to the diazepinoindolones (I) of formula xi

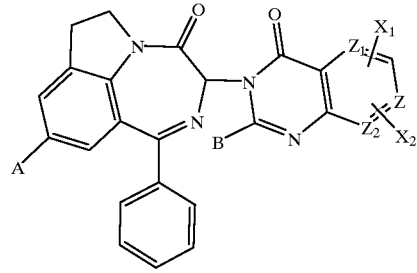

in which:

A is hydrogen, $C_1$–$C_4$alkyl, $OR^1$, hydroxy, nitro, cyano, —$NH_2$, —$NHR^1$, or —$NR^1R^2$;

$R^1$ and $R^2$ independently are $C_1$–$C_4$alkyl, cyclopropyl, cyclopropylmethyl, or $NR^1R^2$ taken together with the nitrogen to which they are bound complete a ring having 4 or 5 carbon atoms;

B is hydrogen, $C_1$–$C_4$alkyl, —$CH_2OM$, —$CH_2OC(=O)$ $(CH_2)_a(CO)_bY^1$–$Y^2$, or —$(CH_2)_cC(=O)OM$;

$Y^1$ is —$(VCH_2CH_2)_c$—, with V=—NH— or —O—; or
$Y^1$ is —$NHCHR^A$—$C(=O)$—;

$Y^2$ is hydrogen, hydroxy, —$OCH_3$, or 4-morpholinyl;

M is hydrogen or $C_1$–$C_4$alkyl;

a=1 or 2; b=0 or 1; c=0, 1, or 2;

Z is CH, then $Z_1$ and $Z_2$ both are CH or N; or

Z is N, then $Z_1$ and $Z_2$ are CH;

$X_1$ and $X_2$ independently are hydrogen, $C_1$–$C_4$alkyl, —$(CH_2)_n$—$OR^3$, halogen, cyano,

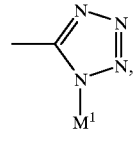

—O—$C_1$–$C_6$alkyl, —$C(=O)R^3$, —$C(=O)OR^3$,—$C(=O)$ $NR^4R^5$, or

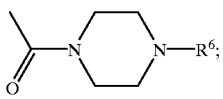

$R^3$ is hydrogen, $C_1$–$C_6$alkyl, benzyl, phenethyl, or —$Q^1$–$Q^2$;

$R^4$ is hydrogen, or $C_1$–$C_4$alkyl;

$R^5$ is hydrogen, $C_1$–$C_4$alkyl, —CHR$^A$—C(=O)OM$^1$, or —$Q^3$–$Q^4$;

$R^6$ is hydrogen, $C_1$–$C_4$alkyl, or —$Q^3$–$Q^5$;

$R^A$ is a residue of a natural α-amino-acid, the carbon atom to which it is linked having either a S configuration, or a R configuration;

$Q^1$ is —(CH$_2$)$_n$—(CHOH)$_m$—(CH$_2$)$_p$—;

$Q^2$ is hydroxy, —O—$C_1$–$C_6$alkyl, —OC(=O)—$C_1$–$C_6$alkyl, or 4-morpholinyl;

$Q^3$ is —(CH$_2$)$_n$—;

$Q^4$ is —NHM$^1$, —NM$^1$M$^2$, or 4-morpholinyl;

$Q^5$ is —M$^1$ or —OM$^1$;

$M^1$ and $M^2$ are independently hydrogen or $C_1$–$C_4$alkyl;

n is 1, 2, or 3; m is 0, 1, 2, 3, or 4; p is 0, 1, 2, or 3, provided that if m is not 0, then p is not 0;

their racemic forms and their isomers, in particular those whose configuration is determnined by carbon 3 of the [1,4]diazepino[6,7,1-hi]indol-4-one ring system, as well as their pharmaceutically acceptable salts, solvates, esters, amides, and prodrugs.

In a preferred embodiment of the compounds of Formula I, the carbon 3 of the [1,4]diazepino[6,7,1-hi]-indol-4-one ring system has the S configuration according to the rule of Cahn, Ingold and Prelog.

In another preferred embodiment of the compounds of Formula I, A is hydrogen, methyl, hydroxy, —OCH$_3$, —NH$_2$, —NHCH$_3$; —N(CH$_3$)$_2$ or 1-pyrrolidinyl; B is $C_1$–$C_4$alkyl, —CH$_2$OH, —CH$_2$OCH$_3$, —CO$_2$—CH$_2$—CH$_3$; and $X_1$ et $X_2$ are independently hydrogen, methyl, methoxy, —CH$_2$OH, F, Cl, Br, —C(=O)OR$^3$, or C(=O)NR$^4$R$^5$;

$R^3$, $R^4$, and $R^5$ being as defined above.

In another preferred embodiment of the compounds of Formula I,

A is —CH$_3$ or —NH$_2$; and

B is —CH$_3$ or —CH$_2$OCH$_3$.

In another preferred embodiment of the compounds of Formula I,

Z, $Z_1$, $Z_2$ are CH; and $X_1$ or $X_2$ is methyl, F, Cl, or Br at position 5 of the quinazoline ring system.

In another especially preferred embodiment of the compounds of Formula I,

Z, $Z_1$, $Z_2$ are CH;

A is —NH$_2$; and $X_1$ or $X_2$ is —C(O)OR$^3$ or —C(=O)NR$^4$R$^5$ at position 7 of the quinazoline ring system;

$R^3$, $R^4$, and $R^5$ being as defined above.

In a most preferred embodiment of the present invention, the compounds are (3S)3-(2-Methyl-4oxo-4H-quinazolin-3yl)-1-phenyl-6,7-dihydro-3H[1,4]diazepino[6,7,1-hi]indol-4-one;

9-Methoxy-3-(2-methyl-4-oxo-4H-quinazolin-3yl)-1-phenyl-6,7-dihydro-3H-[1,4]diazepino[6,7,1-hi]indol-4-one;

2-Methyl-3-(9-methoxy-4-oxo-1-phenyl-3,4,6,7-tetrahydro-[1,4]diazepino[6,7,1-hi]indol-3-yl)-4-oxo-3,4-dihydro-quinazoline-7-carboxylic acid methyl ester;

2-Methyl-3-(9-methoxy-4-oxo-1-phenyl-3,4,6,7-tetrahydro-[1,4]diazepino[6,7,1-hi]indol-3-yl)-4-oxo-3,4-dihydro-quinazoline-7-carboxylic acid.

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid methyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

D-Glucamine 2-methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylate salt;

(3R) 2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

(3S) 2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-morpholin-4-yl-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-acetoxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-methoxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-hydroxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 1-(2S)-glycerol ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-hydroxy-3-morpholin-4-yl-propyl ester.

9-Methyl-3-(2-methyl-4-oxo-4H-quinazolin-3yl)-1-phenyl-6,7-dihydro-3H-[1,4]diazepino[6,7,1-hi]indol-4-one;

(3S)9-Methyl-3-(2,5-dimethyl-4-oxo-4H-quinazolin-3yl)-1-phenyl-6,7-dihydro-3H-[1,4]diazepino[6,7,1-hi]indol-4-one;

(3S)9-Methyl-3-(2,6-dimethyl-4-oxo-4H-quinazolin-3yl)-1-phenyl-6,7-dihydro-3H-[1,4]diazepino[6,7,1-hi]indol-4-one;

(3S)9-Methyl-3-(2,6-dimethyl-4-oxo-4H-quinazolin-3yl)-1-phenyl-6,7-dihydro-3H-[1,4]diazepino[6,7,1-hi]indol-4-one;

(3S)9-Methyl-3-(2,8-dimethyl-4-oxo-4H-quinazolin-3yl)-1-phenyl-6,7-dihydro-3H-[1,4]diazepino[6,7,1-hi]indol-4-one;

3-(5-Methoxy-2-methyl-4-oxo-4H-quinazolin-3yl)-9-methyl-1-phenyl-6,7-dihydro-3H-[1,4]diazepino[6,7,1-hi]indol-4-one;

3-(7-Methoxy-2-methyl-4-oxo-4H-quinazolin-3yl)-9-methyl-1-phenyl-6,7-dihydro-3H-[1,4]diazepino[6,7,1-hi]indol-4-one;

3-(6-Methoxy-2-methyl-4-oxo-4H-quinazolin-3yl)-9-methyl-1-phenyl-6,7-dihydro-3H-[1,4]diazepino[6,7,1-hi]indol-4-one;

3-(6-Bromo-2-methyl-4-oxo-4H-quinazolin-3yl)-9-methyl-1-phenyl-6,7-dihydro-3H-[1,4]diazepino[6,7,1-hi]indol-4-one;

3-(5-Hydroxymethyl-2-methyl-4-oxo-4H-quinazolin-3yl)-9-methyl-1-phenyl-6,7-dihydro-3H-[1,4]diazepino[6,7,1-hi]indol-4-one;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-5-carboxylic acid tertiobutyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-5-carboxylic acid;

3-(7-Hydroxymethyl-2-methyl-4-oxo-4H-quinazolin-3-yl)-9-methyl-1-phenyl-6,7-dihydro-3H-[1,4]diazepino[6,7,1-hi]indol-4-one;

(3S)3-(5-Fluoro-2-methyl-4-oxo-4H-quinazolin-3-yl)-9-methyl-1-phenyl-6,7-dihydro-3H-[1,4]diazepino[6,7,1-hi]indol-4-one;

3-(5-Chloro-2-methyl-4-oxo-4H-quinazolin-3-yl)-9-methyl-1-phenyl-6,7-dihydro-3H-[1,4]diazepino[6,7,1-hi]indol-4-one;

(9-Methyl-3-oxo-4H-quinazolin-3-yl)-1-phenyl-6,7-dihydro-3H-[1,4]diazepino [6,7,1-hi]indol-4-one.

3-(9-Methyl-4-oxo-1-phenyl-3,4,6,7-tetrahydro-[1,4]diazepino [6,7,1-hi]indol-3-yl)-4-oxo-3,4-dihydro-quinazoline-2-carboxylic acid ethyl ester;

5-Chloro-3-(9-methyl-4-oxo-1-phenyl-3,4,6,7-tetrahydro-[1,4]diazepino[6,7,1-hi]indol-3-yl)-4-oxo-3,4-dihydro-quinazoline-2-carboxylic acid ethyl ester;

[3-(9-Methyl-4-oxo-1-phenyl-3,4,6,7-tetrahydro-[1,4]diazepino[6,7,1-hi]indol-3-yl)-4-oxo-3,4-dihydro-quinazolin-2-yl]-acetic acid ethyl ester;

Acetic acid 3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethyl ester;

9-Methyl-3-(2-methyloxymethyl-4-oxo-4H-quinazolin-3yl)-1-phenyl-6,7-dihydro-3H-[1,4]diazepino[6,7,1-hi]indol-4-one;

9-Methyl-3-(2-hydroxymethyl-4-oxo-4H-quinazolin-3yl)-1-phenyl-6,7-dihydro-3H-[1,4]diazepino[6,7,1-hi]indol-4-one;

Succinic acid mono-[3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethyl] ester;

[2-(2-Methoxy-ethoxy)-ethoxy]-acetic acid mono-[3-(9-methyl-4-oxo-1-phenyl-3,4,6,7-tetrahydro-[1,4]diazepino[6,7,1-hi)indol-3-yl)-4-oxo-3,4-dihydro-quinazolin-2-ylmethyl] ester;

N-(2-Morpholin-4-yl-ethyl)-succinamic acid 3-(9-methyl-4-oxo-1-phenyl-3,4,6,7-tetrahydro-[1,4]diazepino[6,7,1-hi]indol-3-yl)-4-oxo-3,4-dihydro-quinazolin-2-yl-methyl ester;

Succinic acid 3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethyl ester 2-morpholin-4-yl-ethyl ester;

6-t-Butoxycarbonylamino-2-{3-[3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethoxycarbonyl]-propionylamino}-hexanoic acid methyl ester;

3-[3-(9-Methyl-4-oxo-1-phenyl-3,4,6,7-tetrahydro-[1,4]diazepino[6,7,1-hi]indol-3-yl)-4-oxo-3,4-dihydro-quinazolin-2-yl]-propanoic acid ethyl ester.

(3S) 3-(2-Methyl-4-oxo-4H-pyrido[3,4-d]pyrimidin-3-yl)-9-methyl-1-phenyl-6,7-dihydro-3H-[1,4]diazepino[6,7,1-hi]indol-1-one;

3-(2-Methyl-4-oxo-4H-pteridin-3-yl)-9-methyl-1-phenyl-6,7-dihydro-3H-[1,4]diazepino[6,7,1-hi]indol-4-one;

9-Amino-3-(2-methyl-4-oxo-4H-pyrido[3,4-d]pyrimidin-3-yl)-1-phenyl-6,7-dihydro-3H-[1,4]diazepino[6,7,1-hi]indol-4-one.

3-(2-Methyl-4-oxo-4H-quinazoin-3-yl)-9-nitro-I -phenyl-6,7-dihydro-3H-[1,4]diazepino[6,7,1-hi]indol-4-one;

3-(2,5-Dimethyl-4-oxo-4H-quinazoin-3-yl)-9-nitro-1-phenyl-6,7-dihydro-3H-[1,4]diazepino[6,7,1-hi]indol-4-one;

3-(2,6-Dimethyl-4-oxo-4H-quinazolin-3-yl)-9-nitro-1-phenyl-6,7-dihydro-3H-[1,4]diazepino[6,7,1-hi]indol-4-one;

3-(2,7-Dimethyl-4-oxo-4H-quinazolin-3-yl)-9-nitro-1-phenyl-6,7-dihydro-3H-[1,4]diazepino[6,7,1-hi]indol-4-one;

3-(2,8-Dimethyl-4-oxo-4H-quinazolin-3-yl)-9-nitro-1-phenyl-6,7-dihydro-3H-[1,4]diazepino[6,7,1-hi]indol-4-one;

3-(2,6,8-Trimethyl-4-oxo-4H-quinazolin-3-yl)-9-nitro-1-phenyl-6,7-dihydro-3H-[1,4]diazepino[6,7,1-hi]indol-4-one;

3-(8-Bromo-2,6-dimethyl-4-oxo-4H-quinazolin-3-yl)-9-nitro-1-phenyl-6,7-dihydro-3H-[1,4]diazepino[6,7,1-hi]indol-4-one;

(3S)3-(2-Methyl-4-oxo-4H-pyrido [3,4-d]pyrimidin-3-yl)-9-nitro-1-phenyl-6,7-dihydro-3H-[1,4]diazepino[6,7,1-hi]indol-4-one;

5-Chloro-2-methyl-3-(9-nitro-4-oxo-1-phenyl-3,4,6,7-tetrahydro-[1,4]diazepino[6,7,1-hi]indol-3-yl)-4-oxo-3,4-dihydro-quinazoline.

(3S)9-Amino-3-(2-methyl-4-oxo-4H-quinazolin-3-yl)-1-phenyl-6,7-dihydro-3H-1,4]diazepino[6,7,1-hi]indol-4-one;

3-(9-Amino-4-oxo-1-phenyl-3,4,6,7-tetrahydro-[1,4]diazepino[6,7,1-hi]indol-3-yl)-2-methyl-4-oxo-3,4-dihydro-quinazoline-7-carboxylic acid methyl ester, and its enantiomers;

3-(9-Amino-4-oxo-1-phenyl-3,4,6,7-tetrahydro-[1,4]diazepino[6,7,1-hi]indol-3-yl)-2-methyl-4-oxo-3,4-dihydro-quinazoline-7-carboxylic acid;

9-Amino-3-(2-methyl-4-oxo-4H-quinazolin-3-yl)-1-phenyl-6,7-dihydro-3H-[1,4]diazepino[6,7,1-hi]indol-4-one;

9-Amino-3-(2,5-dimethyl-4-oxo-4H-quinazolin-3-yl)-1-phenyl-6,7-dihydro-3H-[1,4]diazepino[6,7,1-hi]indol-4-one;

9-Amino-3-(2,6-dimethyl-4-oxo-4H-quinazolin-3-yl)-1-phenyl-6,7-dihydro-3H-[1,4]diazepino[6,7,1-hi]indol-4-one;

9-Amino-3-(2,8-dimethyl-4-oxo-4H-quinazolin-3-yl)-1-phenyl-6,7-dihydro-3H-[1,4]diazepino[6,7,1-hi]indol-4-one;

9-Amino-3-(2,6,8-trimethyl-4-oxo-4H-quinazolin-3-yl)-1-phenyl-6,7-dihydro-3H-[1,4]diazepino[6,7,1-hi)indol-4-one;

9-Amino-3-(5-chloro-2-methyl-4-oxo-4H-quinazolin-3-yl)-1-phenyl-6,7-dihydro-3H-[1,4]diazepino[6,7,1-hi]indol-4-one.

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carbonitrile;

9-Methyl-3-[2-methyl-4-oxo-7-(1H-tetrazol-5-yl)-4H-quinazolin-3-yl]-1-phenyl-6,7-dihydro-3H-[1,4]diazepino[6,7,1-hi]indol-4-one;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-N-methylcarboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-N-dimethylcarboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid (2-morpholin-4-yl-ethyl)-amide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid (3-(morpholin-4yl-propyl)-amide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-(2-amino)-ethylcarboxamide, and the hydrochloride salt thereof;

3-{7-[4-(2-Hydroxy-ethyl)-piperazine-1-carbonyl]-2-methyl-4-oxo-4H-quinazolin-3-yl}-9-methyl-1-phenyl-6,7-dihydro-3H-[1,4]diazepino[6,7,1-hi]indol-4-one, and the hydrochloride salt thereof;

(2S) 6-t-Butoxycarbonylamino-2-{[2-methyl-3-(9-methyl-4-oxo-1-phenyl-3,4,6,7-tetrahydro-[1,4]diazepino[6,7,1-hi]indol-3-yl)-4-oxo-3,4-dihydro-quinazolin-7-carbonyl]-amino}-hexanoic acid methyl ester;

(2S) 6-Amino-2-{[2-methyl-3-(9-methyl-4-oxo-1-phenyl-3,4,6,7-tetrahydro-[1,4]diazepino[6,7,1-hi]indol-3-yl)-4-oxo-3,4-dihydro-quinazolin-7-carbonyl]-amino}-hexanoic acid methyl ester.

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid pentafluorophenyl ester;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-tyrosine;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-alanine;

N-(2-Methyl-3-(9-methyl-4-oxo-1-phenyl-3,4,6,7-tetrahydro-[1,4]diazepino[6,7,1-hi]lndol-3-yl)-4-oxo-3,4-dihydro-quinazoline-7-carboxyl-)-phenylaianine;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-glycine;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-leucine;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-aspartic acid;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-glutamic acid;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-lysine;

2{[2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carbonyl]-amino}-3-phenyl-(L)-propionic acid ethyl ester;

N-(2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxyl-)-proline.

In the foregoing as well as hereinafter:

the terms "$C_1$–$C_4$ alkyl" and "$C_1$–$C_6$ alkyl" mean straight and branched aliphatic groups having from 1 to 4, respectively from I to 6, carbon atoms, examples of which include methyl, ethyl, isopropyl, tert.-butyl, n-hexyl, and isohexyl;

the terms "O—$C_1$–$C_4$ alkyl" and "O—$C_1$–$C_6$ alkyl" mean above-mentioned alkyl groups having from 1 to 4, respectively from 1 to 6, carbon atoms, attached to an oxygen atom, examples of which include methoxy, ethoxy, isopropoxy, tertiobutoxy, and the like;

the term "natural α amino-acid" refers to one of of the naturally occurring amino acids which are constituents of proteins: typical amino acids thus include glycine, alanine, valine, leucine, isoleucine, phenylalanine, serine, cysteine, threonine, lysine, arginine, aspartic acid, asparagine, glutamic acid, glutamine, tyrosine, methionine, tryptophan, histidine and proline;

aromatic is understood to mean a compound containing a phenyl, pyridyl or pyrazinyl ring;

halogen is understood to mean fluorine, chlorine, bromine or iodine;

the symbol "—" means a bond;

the term "patient" means all animals including humans: examples of patients include humans, cows, dogs, cats, goats, sheep, and pigs;

those skilled in the art are easily able to identify patients at risk of having, having, or having had asthma, rheumatoid arthritis, atopic dermatitis, bone loss, pulmonary hypertension, liver injury, septic shock, multiple sclerosis, or inflammatory bowel disorders such as ulcerative colitis and Crohn's disease;

a therapeutically effective amount is an amount of a compound (I) that, when administered to a patient, prevents or ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracistemally, intravaginally, intraperitoneally, intravesically, locally (powders, ointments, or drops), or as a buccal or nasal spray.

A review of salts which are acceptable in pharmacy will be found in J. Pharm. Sci., 1977, 66, 1–19.However, pharmacologically acceptable salt of a compound of formula (I) possessing a basic portion is understood to mean the addition salts of the compounds of formula (I) which are formed from nontoxic inorganic or organic acids such as, for example, the salts of hydrobromic, hydrochloric, sulfuric, phosphoric, nitric, acetic, succinic, tartaric, citric, maleic, hydroxymaleic, benzoic, fumaric, toluenesulfonic, isethionic, and the like, acids. The various quaternary ammonium salts of the derivatives (I) are also included in this category of the compounds of the invention. And pharmacologically acceptable salt of a compound of formula (I) possessing an acidic portion is understood to mean the commonplace salts of the compounds of formula (I) which are formed from nontoxic inorganic or organic bases such as, for example, alkali metal and alkaline-earth metal hydroxides (sodium, potassium, magnesium and calcium hydroxides), amines (dibenzylethylenediamine, trimethylamine, piperidine, pyrrolidine, benzylamine and the like) or alternatively quaternary ammonium hydroxides such as tetramethylammonium hydroxide.

Another aspect of the invention relates to a process for preparing the diazepinoindolones (I), which consists:

i)—for preparing compounds (I) in which A and Z have the designations of (I), B the designations of (I) except for those comprising a carboxylic acid function, and $X_1$ and $X_2$ the meanings of (I) except for those comprising a reactive hydroxyl function, in reacting an intermediate aminodi azepinoindo lone (II) of formula

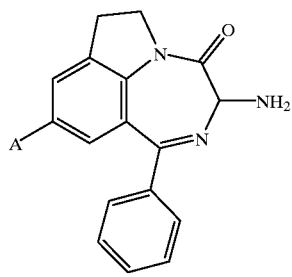

(II)

in which A has the designations of (I),
with an aromatic 2-amido acid (IIIa) of formula

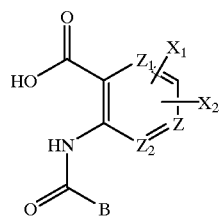

(IIIa)

in which B, Z, $Z_1$, $Z_2$, $X_1$ and $X_2$ have the designations defined above, or
with a 4-oxo-4H-oxazine (IIIb) of formula

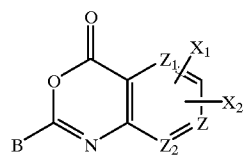

(IIIb)

in which B, Z, $X_1$ and $X_2$ have the designations defined above, or with a mixture comprising from 95 to 5% by weight of an intermediate (IIIa) with from 5 to 95% of an intermediate (IIIb), in which B, Z, $X_1$ and $X_2$, which are identical for both intermediates, have the designations defined above, the intermediates (IIIa) and (IIIb) being isolated or otherwise after their preparation by N-acylation and then, where appropriate, cyclization of an aromatic 2-amino acid (III) of formula

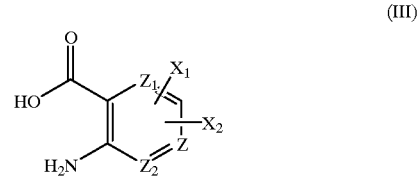

(III)

with 1,1,1-trimethoxyethane, or with a reactant $(B-CO)_n W$ in which B has the designations of (I) except for those comprising a carboxylic acid function, and W is halogen, in particular chlorine or bromine, when n has the value 1, or alternatively is oxygen when n has the value 2;

ii)—for preparing compounds (I) in which B and Z have the designations of (I), A the designations of (I) except for amino and $X_1$ or $X_2$ the meanings of (I) except for those comprising a reactive hydroxyl function, in N-acylating an intermediate diazepinoindolone (IV) of formula

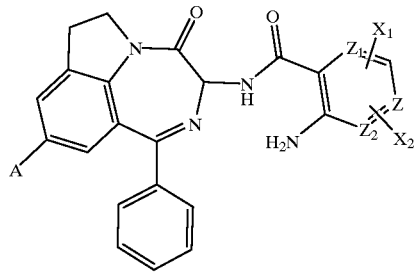

in which A, Z, $X_1$ and $X_2$ have the designations defined above, with a reactant $(B-CO)_n W$ defined above in which B has the meanings designated above, to obtain an intermediate (V) of formula

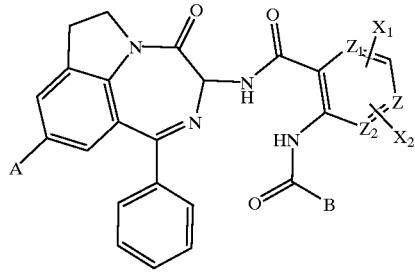

which is cyclized to a diazepinoindolone (I);

iii)—for preparing a compound (I) in which A is amino and where B, Z, $X_1$ and $X_2$ have the meanings of (I), in reducing with sodium sulfide or a metal chloride, in particular tin chloride, a compound (I) in which A is nitro; or iv)—for preparing a compound (I) in which A and Z have the meanings of (I), and B and/or $X_1$ and/or $X_2$ are functionalized:
in hydrolyzing in an acid or alkaline medium a compound (I) comprising an amide (—CO—N<) or ester (—CO—O— or —O—CO—) function, to obtain a corresponding acid or alcohol compound (I);

in reducing with a complex metal hydride or organometallic hydride a compound (I) comprising an acid (—CO—OH) or ester (—CO—O—) finction, to obtain a corresponding alcohol compound (I);

in carrying out the hydrogenolysis in the presence of a metal catalyst of a compound (I) comprising an ether, in particular a benzyl ether (—O—CH$_2$-C$_6$H$_5$), function, to obtain a corresponding alcohol compound (I);

in esterifying or transesterifying with an alcohol a compound (I) having an acid (—CO$_2$H) or ester (—CO—O—) function, to obtain a compound (I) ester of said alcohol; or in amidating with ammonia or a primary or secondary amine a compound (I) comprising an acid (—CO—OH) or ester (—CO—O) function, to obtain a corresponding primary, secondary or tertiary amide compound (I).

in a process A1a, an isobutyl chloroformate/N-methylmorpholine combination in a process A1b and, preferably, an O-[(ethoxycarbonyl)cyanomethylamino]-N,N,N',N'-tetramethyluronium tetrafluoroborate/N,N-diisopropylethylamine (OTUT/DIEA) combination in a process Al c.

To carry out these processes A1, the acetamido acid (lila) is employed in isolated form or, according to a preferred alternative method, in the form of an unisolated compound (IIIa) prepared beforehand by reacting an acid (III) with the acylating agent (B—CO)$_n$W or 1,1,1-trimethoxyethane described above, according to widely documented techniques.

In the experimental part which illustrates the invention, Example 15 is representative of the process A1a, Example 19 of the process A1b and Examples 1 and 3 of the alternatives of the process A1c;

2)—in a process A2 wherein an amine (II) is condensed with a 4-oxo-4H-oxazine (IIIb), in carrying out the operation in an anhydrous medium in a chlorinated hydrocarbon such as CH$_2$Cl$_2$ or an aromatic hydrocarbon such as toluene, Scheme 1

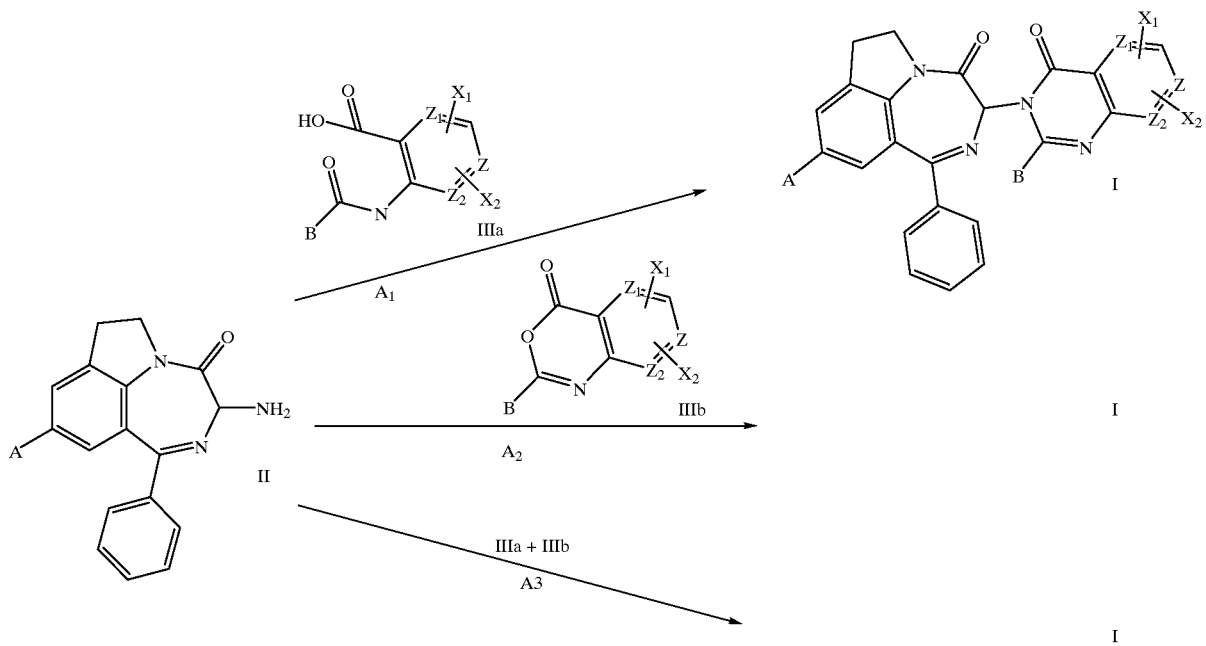

More specifically, the process A for preparing the compounds (I), by reacting an amino intermediate (II) with an intermediate prepared from a 2-amino acid (III), as presented in Scheme 1, consists:

1)—in a process A1 wherein a 2-acetamido acid (IIIa) is employed, in carrying out the N-acylation of the amine (II) and cyclizing the intermediate obtained to obtain the diazepinoindolone (I). The operation is carried out in an anhydrous organic solvent such as a chlorinated hydrocarbon, for instance CH$_2$Cl$_2$ or chloroform, a linear or cyclic ether such as 1,2-dimethoxyethane, tetrahydro[uran or dioxane, an aprotic polar solvent such as pyridine, dimethyl sulfoxide, N,N-dimethylformamide or any other suitable solvent, and mixtures thereof. Advantageously, the reaction is carried out in the presence of a condensing agent and optionally of an organic base. Thus, as condensing agent, phosphorus trichloride is used heating, where appropriate under pressure, above the boiling point of the solvents in order to favor the progress of the reaction.

Just as in the process A1, the intermediate (IIIb) is employed in isolated form or, alternatively, in unisolated form, it being prepared beforehand by conventional processes of acylation of a compound (III) with the agent (B—CO)nW described above and in which, preferably, n has the value 2 and W is oxygen, or alternatively being prepared by a cyclization reaction of an intermediate (IIIa) under the action of an anhydride such as acetic anhydride, Example 7 of the experimental part being representative of this process A2; or 3)—in a process A3, in condensing an amine (II) with a mixture in varied proportions of unisolated intermediates (IIIa) and (IIIb) (which mixture is obtained beforehand by reacting an acid (III) in the presence of a strong organic base with an acylating agent (B—CO)$_n$W described above and in which, preferably, n has the value 1 and W is halogen, and in particular chlorine) in an anhydrous medium in a halogenated hydrocarbon such as CH$_2$Cl$_2$. Example 16 of the experimental part is representative of this process.

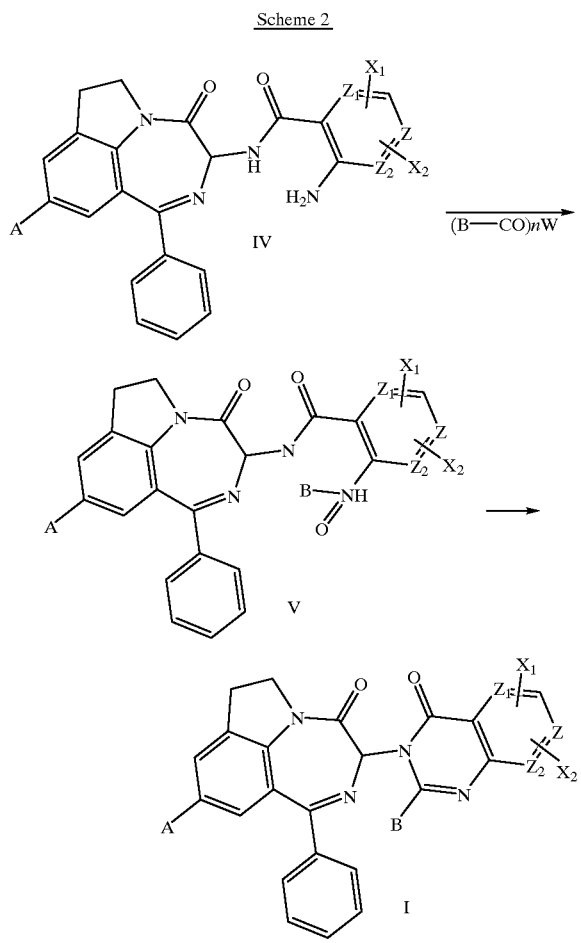

The process B as presented in scheme 2 consists, in a first step, in carrying out the N-acylation of an intermediate (IV), which is carried out by conventional methods such as the reaction of (IV) with the acylating agent (B—CO)$_n$W described above, to obtain an intermediate (V) which, in a second step, is cyclized to a compound (I); this is carried out by heating in an inert solvent having a high boiling point, such as xylene or 1,2-dichlorobenzene, which is preferred. In the experimental part illustrating the invention, Example 27 is representative of this process.

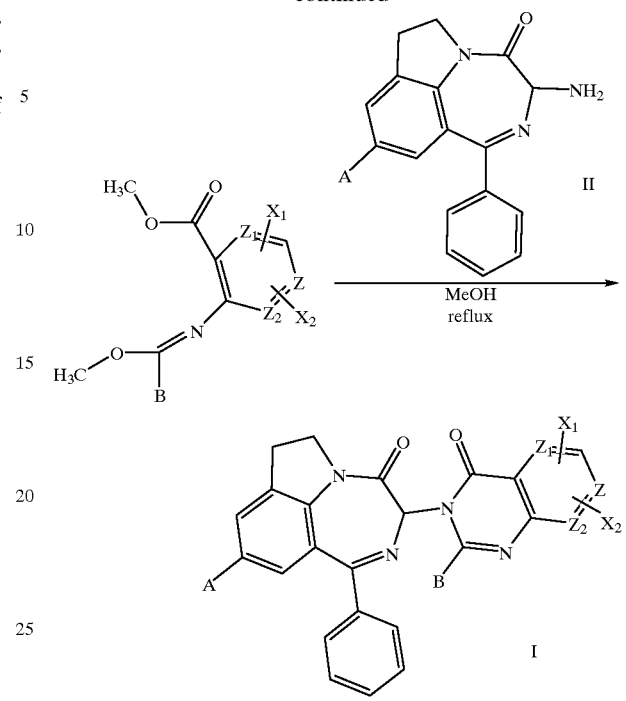

The process A4 as presented in scheme 3 consists in carrying out the N-acylation of the amine (II) with a imine derivative of an aromatic ester (IIc), and cyclizing the intermediate obtained under conditions similar to those of process A2. The intermediate (IIIc), isolated or, preferably, not isolated is first prepared by conventional condensation of an aromatic amine (IVc) with a 1,1,1-trimethoxy-alkane, 1,1,1-trimethoxy-ethane being preferred (B=CH$_3$). The reaction can be carried out in an organic anhydrous solvent like those indicated for process A1. Example 28A is representative of this process.

-continued

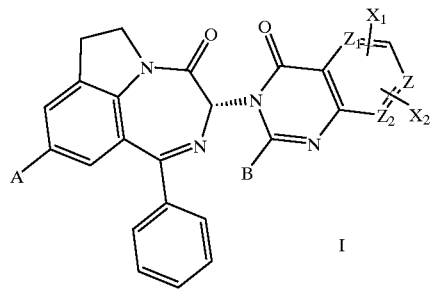

I

The process A5, preferred, as presented in scheme 4 consists in reacting an optically active amine (IVd), prepared according to WO 97/36905, with an ortho-ester, 1,1,1-trimethoxyethane being preferred (B=CH$_3$), to obtain the imine derivative (Vd), and cyclizing the intermediate obtained in a neutral solvent with an acid catalyst.

The process C consists in reducing specifically a compound (I) in which A is nitro to a compound (I) in which A is amino, which is carried out with suitable reducing systems, namely, inter alia, titanium chloride or zinc in an acid medium, or alternatively and preferably, according to a process C1, sodium sulfide in an ethanolic medium, or, according to the process C2, tin chloride in an ethanolic medium, which processes are represented in the experimental part of the invention by Examples 29 and 32, respectively.

The processes D, which, starting from (I), enable compounds to be prepared in which B and/or X$_1$ and/or X$_2$ are functionalized, make use of processes which are known to a person skilled in the art and are widely documented, references to which will be found in a general work such as "Advanced Organic Chemistry" by J. March (3rd Edition—Ed. J. Wiley Intersciences), and which, as may be recalled briefly, consists:

1)—for hydrolyzing an amide (—CO—N=) to a corresponding acid by a process D1a, in performing a hydroxy-de-amination in an aqueous medium and in the presence of an acid catalyst or basic catalyst under conditions suited to the nature of the amide and in the presence of water-miscible inert solvents;

2)—for hydrolyzing an ester (—CO—O—) or (—O—CO—) and obtaining a corresponding acid or alcohol by a process D1b, in performing a hydroxy-de-alkoxylation in an aqueous medium in the presence of an acid catalyst or, and preferably, basic catalyst. The hydrolysis can take place in a two-phase heterogeneous medium for water-insoluble esters, or alternatively in solution in the presence of water-miscible solvents such as, in particular, C$_1$ to C$_4$ alcohols, under time and temperature conditions specific to the product to be treated;

3)—for reducing an acid (—CO—OH) or an ester (—CO—O—) and obtaining a corresponding alcohol by a process D2, in reacting a hydride; a general account of the possibilities will be found in "Advanced Organic Chemistry"—J. March.—3rd Edition—(Ed. J. Wiley Intersciences) p. 1093 et seq. The process D2a consists of a reduction with metal hydrides or organometallic hydrides: the monometallic hydrides are of general formula $M_1(H)_{Y1}(R_3)_{Z1}$ in which $M_1$ is aluminum or boron, $R_3$ is linear- or branched-chain C$_2$ to C$_4$ lower alkyl, Y1 is 1, 2 or 3, Z1 is 0, 1 or 2, the sum Y1+Z1 being in any case equal to 3.

The dimetallic complex hydrides are of formula $M_2M_1(H)_{Y2}(R_3)_{Z2}$ in which $M_1$ is aluminum or boron, $M_2$ is an alkali metal, in particular lithium or sodium, $R_3$ is linear- or branched-chain C$_2$ to C$_4$ lower alkyl or alternatively linear- or branched-chain C$_2$ to C$_4$ lower alkoxy or alternatively alkoxyalkoxy, Y2 is 1, 2, 3 or 4, Z2 is 0, 1, 2 or 3, the sum Y2+Z2 being in any case equal to 4.

Among these hydrides, the dimetallic ones are preferred and, when Z2 is equal to 0, those in which $M_1$ is aluminum and $M_2$ lithium, or alternatively those in which $M_1$ is boron and $M_2$ sodium, namely, in the latter case, sodium borohydride which, favorably, is used in the presence of a Lewis acid such as AlCl$_3$ or in the presence of a sulfuric acid. As regards the hydrides in which Z2 is 1, 2 or 3, those in which Z2 has the value 2, $M_2$ is sodium and $M_1$ aluminum and $R_3$ is alkoxyalkoxy such as a methoxyethoxy group are preferred.

An alternative process D2b consists in performing this reduction on an intermediate ester of the acid, produced in situ for example with an alkyl chloroformate, and in then reducing this unisolated ester with a hydride; as an illustration, Example 11 is representative of this process;

4)—for the hydrogenolysis of a benzyl ether (—O—CH$_2$—C$_6$H$_5$) in the presence of a catalyst and to obtain a corresponding alcohol by a process D3, in performing the reaction in a neutral protic solvent, for instance a water-miscible primary alcohol of boiling point below 100° C., such as ethanol, which is preferred. A suitable catalyst is, inter alia, palladium absorbed on charcoal in the proportion of 5 to 10% and appropriately activated. The reaction is conducted under a hydrogen pressure of 1 to 10 bar and at a temperature of 20 to 70° C. depending of the reactivity of the compound to be treated;

5)—for esterifying, according to a process D4a, a compound (I) comprising an acid function (—CO—OH), and for transesterifying, according to a process D4b, a compound (I) comprising an ester function (—CO—O—):

according to D4a, in reacting the acid compound (I) with a primary alcohol derivative in an anhydrous neutral solvent such as DMF in the presence of a coupling agent such as a carbodiimide (for instance N,N'-diisopropylcarbodiimide (DIC) or N,N'-dicyclohexylcarbodiimide (DCC)) and a catalyst like 4-dimethylamino-pyridine tosylate, or alternatively in the presence of carbonyldiimidazole, which is preferred, as in Example 10 which is representative of this process, and according to D4.b, in reacting an ester compound (I) with an alcohol in the presence of a metal catalyst, optionally in the form of its alkoxide with a C$_1$ to C$_3$ primary alcohol, it being possible for the reaction to be carried out in a neutral aromatic solvent such as benzene, toluene or xylene, and the reaction being favored by the removal of the alcohol formed during the transesterification, which may be achieved by continuous azeotropic distillation;

6)—for amidating with ammonia or a primary or secondary amine an acid compound (I) according to a process D5a, in reacting the acid compound with the amine in the presence of a coupling agent identical to the ones indicated for D4a, or also, in tetrahydro[uran, in the presence of "PyBrop", which is bromotris(pyrrolidino) phosphonium hexafluorophosphate. An alternative method D5b, which is preferred, consists in preparing "in situ", in a first stage, a halide of the acid (I), which is produced with suitable reagents such as, advantageously, oxalyl chloride, and then, in a second stage, in reacting the acid chloride thereby obtained with the amine, which can be in gaseous or liquid form or in solution in a neutral solvent. By way of illustration, Example 8 represents this process;

7)—for dehydrating an amide —CO—NH$_2$ into nitrile, according to a process D6, in reacting an amide compound (I) with a dehydrating agent according to processes referred to in particular in *Advanced Organic Chemistry*—J. March,—3rd Edition—(Ed. J. Wiley Intersciences) or, preferably, using the Burgess reagent, which is the internal salt of (methoxycarbonylsulfamoyl) triethylammonium hydroxide;

8)—for adding an azide and an unsubstituted amide compound (1) in order to obtain the corresponding tetrazole according to a process D7, in reacting the amide with NaN$_3$ in the presence of ammonium chloride;

9)—to obtain from an acid a ketone of formula (I) with X$_1$ or X$_2$=—C(=O) R$^3$ where R$^3$ is preferably C$_1$–C$_4$alkyl , in first preparing a derivative of the acid: acyl chloride, anhydride, ester or amide, which is further reacted according to conventional techniques with an organo-metallic compound, such as R$^3$MgX at a low temperature, or with an alkyl-lithium. In the latter case, one can use directly the acid or, preferably, its lithium salt;

10)—to demethylate a compound (I) wherein A=—OCH$_3$ and obtain the corresponding phenol, in reacting (I) with BBr$_3$ according to a process identical to the one described in application WO 97/36905, Example 1;

11)—to obtain a compound (I) wherein A=—CN, in carrying out a cyanation with BRCN or Cl$_3$C—CN in acidic medium according to processes referred to in particular in *Advanced Organic Chemistty*—J. March,—3rd Edition—(Ed. J. Wiley Intersciences) page 497.

The invention also relates to a medicament for preventing or treating inflammatory disorders including, where it is present, an autoimrnune component, allergic disorders or bronchoconstriction, and which is useful, in particular, in the treatment of asthma, rheumatoid arthritis, atopic dermatitis or inflammatory intestinal diseases. Treatment of animals, including humans, consist in administering a diazepinoindolone according to the invention, in a pharmaceutical dosage form which is suited to the disease to be treated. Conditions also amenable to treatment with a compound according to the invention include inflammatory intestinal diseases like ulcerative colitis and Crohn's disease, disorders characterized by an important increase of TNF-α, such as pulmonary hypertension (primary or secondary), liver failure in particular following immunologic or inflammatory hepatic injury, bone loss (osteoporosis or osteomalacia), septic shock, and multiple sclerosis.

The examples which follow illustrate, without, however, limiting it, the implementation of the processes and the products of the invention. The purity, identity and physicochemical properties of the products and of the essential intermediates prepared are determined; thus:

the purity is verified by thin-layer chromatography (TLC) on silica gel (Merck 60–F254), and the Rf observed is recorded for the elution solvent used which is, more often than not, identical to the one used for the preparative chromatographic purification of the compounds. These solvents are identified by the following designations:

C/A20: cyclohexane/acetone, 80:20 (v/v),
C/A30: cyclohexane/acetone, 70:30 (v/v),
D/A1: CH$_2$Cl$_2$/acetone, 99:1 (v/v),
D/A1.5: CH$_2$Cl$_2$/acetone, 98.5:1.5 (v/v),
D/A2: CH$_2$Cl$_2$/acetone, 98:2 (v/v),
D/A3: CH$_2$Cl$_2$/acetone, 97:3 (v/v),
D/A4: CH$_2$Cl$_2$/acetone, 96:4 (v/v),
D/A5: CH$_2$Cl$_2$/acetone, 95:5 (v/v),
D/A6: CH$_2$Cl$_2$/acetone, 94:6 (v/v),
D/A10: CH$_2$Cl$_2$/acetone, 90:10 (v/v),
D/A20: CH$_2$Cl$_2$/acetone, 80:20 (v/v),
D/A30: CH$_2$Cl$_2$/acetone, 70:30 (v/v),
D/M1: CH$_2$Cl$_2$/methanol, 99:1 (v/v),
D/M2: CH$_2$Cl$_2$/methanol, 98:2 (v/v),
D/M3: CH$_2$Cl$_2$/methanol, 97:3 (v/v),
D/M5: CH$_2$Cl$_2$/methanol, 95:5 (v/v),
D/M7: CH$_2$Cl$_2$/methanol, 93:7 (v/v),
D/M30: CH$_2$Cl$_2$/methanol, 70:30 (v/v),
D/MN2: CH$_2$Cl$_2$/10% ammoniacal methanol, 98:2 (v/v),
D/MN5: CH$_2$Cl$_2$/10% ammoniacal methanol, 95:5 (v/v)
D/MN 10: CH$_2$Cl$_2$/10% ammoniacal methanol, 90:10 (v/v),
D/MN20: CH$_2$Cl$_2$/10% ammoniacal methanol, 80:20 (v/v),
Ea: ethyl acetate;

the identity of the products obtained with the proposed structures is verified by their proton nuclear magnetic resonance spectrum and by their infrared spectrograrn.

The $^1$H NMR spectra are recorded at 400 MHz on a Brhcker make instrument, the compounds being dissolved in deuterochloroformn with tetramethylsilane as internal reference. The nature of the signals, their chemical shifts in ppm and the number of protons they represent are noted.

The infrared spectra are recorded in a potassium bromide disk on a Shimadzu IR-435 spectrometer.

the physicochemical properties, recorded wherever a sufficient amount of product was available, are their uncorrected melting point, determined by the capillary tube method, and their optical rotation, determined at room temperature in the region of 20° C. on a Polartronic instrument in a cell 10 cm long, and the results of which enable the optical purity to be assessed in some cases by calculation of the enantiomeric excess (e.e.). Commonly used abbreviations for some reagents and solvents have been used, such as:

THF, for tetrahydro[uran;
DMF, for N,N-dimethylformamide;
OTUT, for O-[(ethoxycarbonyl)cyanomethylamino]-N,N,N',N'-tetramethyluronium tetrafluoroborate;
DIEA, for N,N-diisopropylethylamine.

As regards the experimental description, concentration or removal of the solvents is understood to mean, where appropriate after they are dried over a suitable drying agent such as NA$_2$SO$_4$ or MgSO$_4$, a distillation under a vacuum of 25 to 50 mm of Hg and with moderate heating on a water bath; flash chromatography on a silica column is understood to mean the implementation of a method adapted from that of Still et al. (1978) J. Org. Chem. 43: 2923, the purity of the elution fractions being verified before they are pooled and evaporated under the conditions defined above.

EXAMPLES

Intermediate Compounds

Intermediate 1: (3RS)-3-Amino-1-phenyl-6,7-dihydro-3H-[1,4]diazepino[6,7,1-hi]indol-4-one [(II); A=H]

The preparation of the racemic compound is described in Example 1 stages a) and b) of EP 0 340 064 A1, in which the enantiomers are also disclosed.

Intermediate 2.a: (3RS)-3-amino-9-methyl-1-phenyl-6,7-dihydro-3H-[1,4]diazepino[6,7,1-hi]indol-4-one [(II); A=CH$_3$).

The compound is synthesized as described in Patent FR 94 12282 (Publication No. 2 725 719), in the preparation of the intermediate 2.a.

Intermediate 2.b: (3R)-3-amino-9-methyl-1-phenyl-6,7-dihydro-3H-[1,4]diazepino[6,7,1-hi]indol-4-one [(II); A=CH$_3$].

The compound is synthesized as described in Patent FR 94 12282 (Publication No. 2 725 719), in the preparation of the intermediate 2.b.

Intermediate 3.a: (3RS)-3-amino-9-nitro-1-phenyl-6,7-dihydro-3H-[1,4]diazepino[6,7,1-hi]indol-4-one [(II): A=NO₂ and
Intermediate 3.b: (3R)-3-amino-9-nitro-1-phenyl-6,7-dihydro-3H-[1,4]diazepino[6,7,1-hi]indol-4-one [(II); A=NO₂]. The compound is synthesized as described in International Application WO 97/36905 (intermediate 2, stage 1) from the precursor of the same stereochemistry.
Intermediate 4: (3R)-3,9-diamino-1-phenyl-6,7-dihydro-3H-[1,4]diazepino[6,7,1-hi]indol-4-one [(II); A=—NH₂]. The compound is synthesized as described in International Application WO 97136905 (intermediate 2, stage 2).
Intermediate 5: (3S)-3-amino-N-(9-nitro-4-oxo-1-phenyl-6,7-dihydro-3H-[1,4]diazepino[6,7,1-hi]indol-3-yl) isonicotinamide
Stage 1: 25.4 g (184 mmol) of 3-arninoisonicotinic acid in 600 ml of dioxane are introduced into a reactor, and 184 ml of IN NaOH solution are then added. The mixture is cooled with stiring to 5° C. and 60.24 g (236 mmol) of di-t-butyl dicarbonate are then added dropwise. The mixture is then maintained for 4 h at 20–25° C. and thereafter 38.6 g (200 mmol) of citric acid are added portionwise. The solvents are distilled off and the residue is taken up with 500 ml of water. The insoluble matter is filtered off, washed with water and then dried under vacuum at 50° C. 36.5 g of 3-(t-butyloxycarbonylarnino)isonicotinic acid are obtained. Yld=81%—TLC (D/M30): Rf=0.45.
Stage 2: 11.1 g (46.5 mmol) of the compound obtained in the preceding stage in 500 ml of THF dried over molecular sieve are introduced into a reactor protected from moisture. With stirring, 19.5 ml, equivalent to 14.13 g (139.6 mmol), of triethylamine are added and, after solubilization, 15.0 g (46.5 mmol) of the intermediate (R) amine 3.b and then 26.0 g (55.8 mmol) of PyBrop are added. The mixture is stirred for 20 h at 20–25° C. and the solvents are then removed by distillation. The residue is purified by flash chromatography on a silica column. Elution with the mixture D/M2 enables 9.0 g of (3S)-3-t-butyloxycarbonylamino-N-(9-nitro-4-oxo-1-phenyl-3,4,6,7-tetrahydro-[1,4]diazepino[6,7,1-hi]indo]-3-yl) isonicotinamide to be obtained. Yld=36%—TLC (D/M5): Rf=0.45.
Stage 3: 9.0 g (16.6 rmnol) of the compound obtained in the preceding stage in 90 ml of CH₂Cl₂ are introduced into a reactor protected from moisture. With stirring at 20–25° C., 45 ml of pure trifluoroacetic acid are introduced dropwise. The mixture is then maintained for 1 h under these conditions and thereafter the solvents are removed by distillation. The residue is taken up with 100 ml of ethyl acetate and the mixture is extracted with 3 times 75 ml of saturated NaHCO₃ solution and then with water. The ethyl acetate is removed by distillation and the residual product, intermediate 5 in amorphous form, is found to be pure by TLC.
Weight: 5.1 g—Yld=69.0%—TLC (D/M5): Rf=0.25.

Example 1
(3S)-3-(2-methyl-4-oxo-4H-quinazolin-3-yl)-1-phenyl-6,7-dihydro-3H[1,4]diazepino[6,7,1-hi]indol-4-one.
(I); A=H, Z=CH, B=CH₃, X₁=H, X₂=H (process A1c)
In a reactor protected from moisture, 2.65 g (5.5 mmol) of the intermediate amine 1 of R configuration are dissolved with stirring in 30 ml of CH₂Cl₂.1.08 g (6.0 mmol) of 2-acetamidobenzoic acid and then 1.8 g (5.5 mmol) of OTUT are added. The mixture is cooled to 0° C. and 1.4 g (11 mmol) of DIEA are then added. After 16 h with stirring at laboratory temperature, the insoluble matter is filtered off and the filtrate extracted successively with IN HCl solution and saturated NaHCO₃ solution and lastly with water. The solvent is evaporated off and the residue purified by flash chromatography on a silica column, eluting with the solvent D/A3. 0.65 g of a crystallized white solid is obtained. Yld=28%—M.p.=210C—TLC (D/M3): Rf=0.26—["]$_D$=+23.6E (c=1, CH₂Cl₂).
¹H NMR (ppm): 1.75 (s, 1H); 2.85 (s,3H); 3.15 (m,1H); 3.4 (m,1H); 4.0 (m, 1H); 4.22 (m, 1H); 7.12 (m, 1H); 7.20 (s, 1H); 7.45 (m, 5H); 7.55 (d, 2H); 7.75 (m, 2H); 8.2 (d, 1H). IR: 1660, 1570, 1460, 1440, 1380, 1340, 1290, 1240, 1170, 770, 690 cm⁻¹.
(3S)-3-(2-methyl-4-oxo-4H-quinazolin-3-yl)-1-phenyl-6,7-dihydro-3H [1,4]diazepino[6,7,1-hi]indol-4-one.
(I); A=H, Z=CH, B=CH₃, X₁=H, X₂=H (process A4)
1 g of 2-amino-N-((3R) 9-amino-4-oxo-1-phenyl-3,4,6,7-tetrahydro-[1,4]diazepino[6,7,1-hi]-indol-3-yl)-benzamide is dissolved in 10 ml of . 1,1,1-trimethoxyethane in a reactor. The medium is stirred and refluxed for 5 h, and then concentrated to dryness at 50° C. under vacuum. The residue is dissolved in 10 ml CH₂Cl₂ ; a few drops of trifluoroacetic acid are added. After 10 h, the solvent is evaporated off and the residue purified by chromatography on a silica column, eluting with CH₂Cl₂.containing increasing concentration of MeOH. The title compound is obtained as a white solid, with a yield of 96% and an e.e.>97%.

Example 2
9-methyl-3-(2-methyl-4-oxo-4H-quinazolin-3-yl)-1-phenyl-6,7-dihydro-3H-[1,4]diazepino [6,7,1-hi] indol-4-one.
(I); A=CH₃, Z=CH, B=CH₃,X₁=H, X₂=H (process A1c)
In a 50-ml reactor protected from moisture and under a nitrogen atmosphere, 2.3 g (7.9 mmol) of the intermediate amine 2.a are introduced into 25 ml of CH₂Cl₂, followed by 1.41 g (7.9 mmol) of 2-acetamidobenzoic acid. The mixture is cooled to 0° C. and 2.24 g (17 mmol) of DIEA are added. The mixture is kept stirring for 1 min at 0° C. and then for 12 h at room temperature, and 2.56 g (7.9 mmol) of OTUT are then added. The mixture is cooled to 0° C. and 2.24 g of DIEA are added. The mixture is maintained for 1 min at 0° C. and then 2 h at room temperature. 2.56 g of OTUT and 2.24 g of DIEA are then added under the same conditions; the mixture is then kept stirring for 48 h at room temperature and thereafter washed with 20 ml of water. The solvent is evaporated off and the residue purified by flash chromatography on silica, eluting with the solvent D/A2. The fractions determined pure by TLC are pooled and the solvent is evaporated off. 1.4 g of a light yellow solid are obtained. Yld=40%—TLC (D/A5): Rf=0.36.
¹H NMR δ (ppm): 2.2 (s, 3H); 2.8 (s, 3H); 3.05 (m, 1H); 3.3 (m, 1H); 3.4 (m, 1H); 4.65 (m, 1H); 7.0 (s, 1H); 7.1 (s, 1H); 7.35–7.7 (m, 9H); 8.15 (d, 1H).
IR: 3300, 2850, 1660, 1580, 1570, 1460, 1380, 1290, 1230, 1170, 870, 770, 690 cm⁻¹.

Example 2A
9-methoxy-3-(2-methyl-4-oxo-4H-quinazolin-3-yl)-1-phenyl-6,7-dihydro-3H-[1,4]diazepino [6,7,1-hi] indol-4-one.
(I); A=OCH₃, Z=CH, B=CH₃, X₁=H, X₂=H (process A12c).
0.834 g (4.65 mmol) of acetylanthranilic acid and 1.3 g (4.23 mmol) of 3-amino-9-methoxy-1-phenyl-6,7-dihydro-3H-[1,4]diazepino[6,7,1-hi]indol-4-one are dissolved in 13 ml of CH₂Cl₂, the mixture is stirred at room temperature and 0.7 g (5 mmol) of phosphorus trichloride is added. The mixture is stirred for 20 h and 0.35 g of phosphorus trichlonrde is added, followed by a fuirther 0.35 g 8 h later. The mixture is cooled, 50 ml of saturated NaHCO$_3$ solution and 100 ml of CH$_2$Cl$_2$ are added and the organic phase is separated out after settling has taken place and washed with water. This solution is dried, evaporated and purified by chromatography in the mixture DM1. 0.33 g of yellow powder is obtained. M.p.=277° C.—Yld 17%.—TLC (DM3): Rf=0.47.

$^1$H NMR δ (ppm): 2.7 (s, 3H); 3.15 (m, 1H); 3.4 (m, 1H); 3.75 (s, 3H); 3.9 (q, 1H); 4.6 (m, 1H); 6.7 (s, 1H); 7.0 (s, 1H); 7.3 (s, 1H); 7.5 (m, 4H); 7.55 (m, 2H); 7.6 (m, 1H); 7.8 (m, 1H); 8.1 (dd, 1H).

IR: 3300, 2850, 1660, 1580, 1570, 1460, 1380, 1290, 1230, 1170, 870, 770, 690 cm$^{-1}$.

Example 2B

Methyl 2-methyl-3-(9-methoxy-4-oxo-1-phenyl-3,4,6,7-tetrahydro[1,4]diazepino[6,7,1-hi]indol-3-yl)-4-oxo-3,4-dihydroquinazoline-7-carboxylate.

(I); A=OCH$_3$, Z=CH, B=CH$_3$, X$_1$=H, X$_2$=CO$_2$CH$_3$ at 7. (Process A1c).

The compound is prepared in two steps according to Example 6A below, using dimethyl 2-aminoterephthalate and 3-amino-9-methoxy-1-phenyl-6,7-dihydro-3H-[1,4]diazepino [6,7,1-hi]indol-4-one.

Yld: 56%—powder—M.p.=264–265° C.—TLC (D/MS): Rf=0.8.

$^1$H NMR δ (ppm): 2.7 (s, 3H); 3.15 (m, 1H); 3.35 (m, 1H); 3.7 (s, 1H); 3.95 (s, 3H); 4.0 (m, 1H); 4.6 (t, 1H); 6.65 (s, 1H); 6.9 (s, 1H); 7.45–7.6 (m, 6H); 8 (dd, 1H); 8.2 (m, 2H).

Example 2C 2-methyl-3-(9-methoxy-4-oxo-1-phenyl-3,4,6,7-tetrahydro[1,4]diazepino[6,7,1-hi]indol-3-yl)-4-oxo-3,4-dihydroquinazoline-7-carboxylic acid.

(I); A=OCH$_3$, Z=CH, B=CH$_3$, X$_1$=H, X$_2$=CO$_2$H at 7 (process D1b).

1.3 g of product of Example 2B (2.55 mmol) are dissolved in 55 ml of THF, 18 ml of water containing 0.33 g of potassium hydroxide are added and the mixture is stirred at 20–25° C. for 5 h. Ice is added and the mixture is acidified to pH=5. It is extracted with CH$_2$Cl$_2$. The extracts are purified by chromatography. 0.55 g obtained. Yld: 44%. Decomposition starting at 225° C.—TLC (DM5): Rf=0.1.

$^1$H NMR δ (ppm): 2.7 (s, 3H); 3.2 (m, 1H); 3.4 (m, 1H); 3.8 (s, 3H); 3.9 (m, 1H); 4.6 (t, 1H); 6.65 (d, 1H); 6.9 (s, 1H); 7.5 (m, 6H); 8.0 (d, 1H); 8.1 (m, 2H).

Example 3

(3S)-9-methyl-3-(2,5-dimethyl-4-oxo-4H-quinazolin-3-yl)-1-ph enyl-6,7-dihydro-3H-[1,4]-diazepino[6,7,1-hi]indol-4-one.

(I); A=CH$_3$, Z=CH, B=CH$_3$, X$_1$=H, X$_2$=CH$_3$ at position 5 (process A1c)

In a 50-ml round-bottomed flask protected from moisture and under a nitrogen atmosphere, 1.2 g (4.12 mmol) of the intermediate amine 2.b of R configuration, 0.88 g (4.53 mmol) of 2-acetamido-6-methylbenzoic acid, prepared by reacting 2-amino-6-methylbenzoic acid with acetic anhydride, and then 1.33 g (4.12 mmol) of OTUT are introduced into 20 ml of CH$_2$Cl$_2$. The medium is cooled in an ice bath and 1.44 ml (8.24 mmol) of DIEA are added. The mixture is kept stirring for 1 min at 0° C. and then for 16 h at room temperature, and 1.33 g of OTUT are then added. The mixture is cooled to 0° C. and 1.44 ml of DIEA are added. The mixture is maintained for 1 min at 0° C. and then for 1.5 h at room temperature, and then washed with 1N HCl followed by saturated NaHCO$_3$. It is dried over Na$_2$SO$_4$, the solvent is evaporated off and the residue purified by flash chromatography on silica, eluting with the solvent D/M1. The fractions determined pure by TLC are pooled and the solvent is evaporated off. The product is recrystallized in methanol. Weight=0.85 g—Yld: 46%—white solid—M.p.=225° C.—["]$_D$=+23.6E (c=1, CH$_2$Cl$_2$).—TLC (D/M2): Rf=0.42.

$^1$H NMR δ (ppm): 2.35 (s, 3H); 2.8 (2s, 6H); 3.1 (m, 1H); 3.4 (m, 1H); 4.0 (q, 1H); 4.7 (t, 1H); 7.05 (s, 1H); 7.4 (m, 10H).

Example 4

(3S)-9-methyl-3-(2,6-dimethyl-4-oxo-4H-quinazolin-3-yl)-1-phenyl-6,7-dihydro-3H-[1,4]diazepino[6,7,1-hi]indol-4-one. (I); A=CH$_3$, Z=CH, B=CH$_3$, X$_1$=H, X$_2$=CH$_3$ at position 6 (process A1c)

In a first step, 2-acetamido-5-methylbenzoic acid is prepared as described in the preceding example from 2-amino-5-methylbenzoic acid, and the compound is then prepared according to a procedure identical to Example 3.

Yld: 31%—pink solid—M.p.=152° C.—TLC (D/M2): Rf=0.39

$^1$H NMR δ (ppm): 2.3 (s, 3H); 2.4 (s, 3H); 2.8 (s, 3H); 3.05 (m, 1H); 3.3 (m, 1H); 3.9 (q, 1H); 4.65 (t, 1H); 7.3 (m, 10H); 7.95 (s, 11H).

Example 5

(3S)-9-methyl-3-(2,8-dimethyl-4-oxo-4H-quinazolin-3-yl)-1-ph enyl-6,7-dihydro-3H-[1,4]diazepino[6,7,1-hi]indol-4-one. (I); A=CH$_3$, Z=CH, B=CH$_3$, X$_1$=H, X$_2$=CH$_3$ at position 8 (process A1.c)

The compound is prepared in two steps according to Example 3, using 2-amino-3-methylbenzoic acid—Yld: 15%—brown solid—M.p.=158° C.—TLC (D/M2): Rf=0.72

$^1$H NMR δ (ppm): 2.3 (s, 3H); 2.6 (s, 3H); 2.8 (s, 3H); 3.0 (m, 1H); 3.3 (m, 1H); 3.9 (q, 1H); 4.65 (t, 1H); 7.3 (m, 10H); 8.0 (d, 1H).

Example 6

3-(5-methoxy-2-methyl-4-oxo-4H-quinazolin-3-yl)-9-methyl-1-phenyl-6,7-dihydro-3H-[1,4]diazepino[6,7,1-hi]indol-4-one. (I); A CH$_3$, Z=CH, B=CH$_3$, X$_1$=H, X$_2$=OCH$_3$ at position 5 (process A1c)

The compound is prepared in two steps according to Example 3, using 2-amino-6-methoxybenzoic acid. Yld: 25%—M.p.=160–162° C.—TLC (C/A30): Rf=0.22.

$^1$H NMR δ (ppm): 2.35 (s, 3H); 2.6 (s, 3H); 3.1 (m, 1H); 3.35 (m, 1H); 3.8 (s, 3H); 3.9 (q, 1H); 4.55 (t, 1H); 6.9 (s, 1H); 7.0 (m, 2H); 7.05 (d, 1H); 7.5 (m, 6H); 7.7 (t, 1H).

IR: 3400, 2900, 1680, 1590, 1560, 1470, 1380, 1320, 1260, 1080, 700 cm$^{-1}$

Example 6A 3-(7-methoxy-2-methyl-4-oxo-4H-quinazolin-3-yl)-9-methyl-1-phenyl-6,7-dihydro-3H-[1,4]-diazepino[6,7,1-hi] indol-4-one.

(I); A=CH$_3$, Z=CH, B=CH$_3$, X$_1$=H, X$_2$=OCH$_3$ at 7 (process A11.c)

The compound is prepared in two steps using 2.05 g of methyl 2-amino-4-methoxybenzoate, which is refluxed for 6 h in 6 ml of 1,1,1-trimethoxyethane. The volatile products are evaporated and stripped off under high vacuum. The intermediate compound is not purified, and is used directly in the following step. 0.65 g of the amine 2.a is added to 5 ml of methanol and the solution is refluxed for 16 h under a nitrogen atmosphere. The product is purified by flash chromatography on silica in the mixture D/M1.

Yld: 9%—TLC (D/M2): Rf=0.3.

$^1$H NMR δ (ppm): 2.3 (s, 3H); 2.7 (s, 3H); 3.0–3.1 (m, 1H); 3.25–3.35 (m, 1H); 3.85–3.95 (m, 4H); 4.6–4.7 (m, 1H); 6.9–7.05 (m, 3H); 7.15–7.55 (m, 7H); 8.05 (d, 1H).

IR: 3500, 2900, 1685, 1600, 1585, 1565, 1425, 1380, 1280, 1160, 1020, 780, 700 cm$^{-1}$

Example 6B 3-(6-methoxy-2-methyl-4-oxo-4H-quinazolin-3-yl)-9-methyl-1-phenyl-6,7-dihydro-3H-[1,4]-diazepino[6,7,1-hi]indol-4-one.

(I); A=CH$_3$, Z=CH, B=CH$_3$, X$_1$=H, X$_2$=OCH$_3$ at 6 (process A1c)

The compound is prepared in two steps according to Example 6A, using methyl 2-amino-5-methoxybenzoate. Yld: 28%—TLC (D/M2): Rf=0.4. White powder—m.p. >270° C.

$^1$H NMR (ppm): 2.4 (s, 3H); 2.6 (s, 3H); 3.15 (m, 1H); 3.35 (m, 1H); 3.85 (s, 3H); 4.0 (q, 1H); 4.55 (t, 1H); 7.0 (s, 1H); 7.05 (m, 2H); 7.4–7.55 (m, 8H); 7.6 (d, 1H).

IR: 1690, 1660, 1590, 1490, 1370, 1270, 1240, 1140, 1100, 1020, 970, 940, 700 cm$^{-1}$

Example 6C 3-(6-bromo-2-methyl-4-oxo-4H-quinazolin-3-yl)-9-methyl-1-phenyl-6,7-dihydro-3H-[1,4]diazepino-[6,7,1-hi]indol-4-one.

(I); A=CH$_3$, Z=CH, B=CH$_3$, X$_1$=H, X$_2$=Br at 6 (process A1c)

The compound is prepared in two steps according to Example 6A, using methyl 2-amino-5-bromobenzoate.

Yld: 33%—TLC (D/M2): Rf=0.75.—White powder—M.p.=178–181° C.

$^1$H NMR δ (ppm): 2.35 (s, 3H); 2.65 (s, 3H); 3.1–3.2 (mn, 1H); 3.3–3.4 (m, 1H); 4.0 (m, 1H); 4.6 (m, 1H); 6.95 (s, 1H); 7.05 (s, 1H); 7.45–7.55 (m, 6H); 7.65 (d, 1H); 8.0 (d, 1H); 8.15 (s, 1H).

IR: 1660, 1580, 1460, 1380, 1330, 1270, 1230, 1150, 1110, 830, 770, 700 cm$^{-1}$.

Example 6D 3-(5-hydroxymethyl-2-methyl-4-oxo-4H-quinazolin-3-yl)-9-methyl-1-phenyl-6,7-dihydro-3H-[1,4]diazepino[6,7,1-hi]indol-4-one. (I); A=CH$_3$, Z=CH, B=CH$_3$, X$_1$=H, X$_2$=CH$_2$OH at 5 (process D2b)

The product is prepared as in Example 11 below, starting with the product of Example 6F. Starting with 0.3 g, 12 mg of white foam are obtained after flash chromatography.

Yld: 4%—TLC (D/M2): Rf=0.45.

Example 6E tert-Butyl 2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-5-carboxylate.

(I); A=CH$_3$, Z=CH, B=CH$_3$, X$_1$=H, X$_2$=CO$_2$C(CH$_3$)$_3$ at 5 (process A1c)

1.55 g (6.2 mmol) of methyl 2-amino-6-tert-butyloxycarbonylbenzoate are refluxed in 5 ml of 1,1,1-trimethoxyethane for 5 h and the solution is evaporated to dryness under a high vacuum. 1.854 g of the intermediate 2a (6 mmmol) and 4 ml of methanol are added and the mixture is refluxed for 24 h. After chromatography, 1 g (Yld=41%) of product which crystallizes from CH$_3$OH is obtained. White crystals—M.p.=255° C.—TLC (D/M2.5): Rf=0.5.

$^1$H NMR δ (ppm): 1.6 (s, 9H); 2.35 (s, 3H); 2.8 (s, 3H); 3.05 (m, 1H); 3.15 (m, 1H); 3.35 (m, 1H); 3.45 (m, 1H); 4.65–4.75 (m, 1H); 7.05 (s, 1H); 7.15 (s, 1H); 7.25–7.6 (m, 7H); 7.7 (d, 1H).

IR: 3300, 12900, 1720, 1640, 1590, 1570, 1440, 1360, 1310, 1280, 1140, 980, 780, 750, 705 cm$^{-1}$.

Example 6F 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-5-carboxylic acid. (I); A CH$_3$, Z=CH, B=CH$_3$, X$_1$=H, X$_2$=CO$_2$H at 5 (process D1b)

0.5 g of the ester obtained in the above example is dissolved in 7 ml of CH$_2$Cl$_2$.3 ml of trifluoroacetic acid are added dropwise and the mixture is stirred for 90 min at room temperature. Water, ice and CH$_2$Cl$_2$ are added, the organic phase is washed with saturated sodium chloride solution, the phases are separated after settling has taken place and the organic phase is dried. Obtained: 0.42 g—Yld: 95%—White powder—M.p.=195–200° C. TLC (D/M15): Rf=0.2.

$^1$H NMR δ (ppm): 2.35 (s, 3H); 2.7 (s, 3H); 3.1–3.2 (m, 1H); 3.4–3.5 (m, 1H); 3.95–4.05 (m, 1H); 4.55–4.65 (m, 1H); 6.9 (s, 1H); 7.05 (s, 1H); 7.4–7.55 (m, 7H); 7.7 (d, 1H); 7.8–7.9 (t, 1H).

IR: 3400, 1670, 1590, 1570, 1540, 1480, 1300, 1250, 1160, 830, 790, 695 cm$^{-1}$.

Example 7

2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-7-carboxylic acid. (I); A=CH$_3$, Z=CH, B=CH$_3$, X$_1$=H, X$_2$=CO$_2$H at position 7 (process A2)

In an autoclave, a mixture of 1 g (4.9 imnol) of 2-methyl-4-oxo-4H-benzo[d][1,3]oxazine-7-carboxylic acid (prepared from 2-aminoterephthalic acid and acetic anhydride according to J. Am. Chem. Soc., 29 (1907) p.86) and 1.42 g (4.9 mmol) of the intermediate 2.a in 15 ml of CH$_2$Cl$_2$ is brought to 200° C. under a pressure of 3 bar for 8 h. The medium is cooled, the solvent is evaporated off and the residue is purified by flash chromatography on a silica column, eluting with the solvents D/M3, D/M5 and D/M7. The fractions of interest are pooled, evaporated and again subjected to flash chromatography on silica, eluting with the solvent D/MN20. 100 mg of an amorphous solid are obtained. Yld: 4%—TLC (D/MN20): Rf=0.37.

$^1$H NMR δ (ppm): 2.35 (s, 3H); 2.65 (s, 3H); 3.1 (m, 1H); 3.35 (q, 1H); 3.95 (q, 1H); 4.45 (t, 1H); 6.95 (s, 1H); 7.05 (s, 1H); 7.4–7.55 (m, 6H); 8.0 (d, 1H); 8.1 (d, 2H).

Example 7A

Methyl 2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-7-carboxylate.

(I); A=CH$_3$, Z=CH, B=CH$_3$, X$_1$=H, X$_2$=CO$_2$CH$_3$ at 7. (Process A1c)

The compound is prepared in two steps according to Example 6A, using dimethyl 2-aminoterephthalate.

Yld: 32%—Powder—M.p.=246° C.—TLC (I)/M1): Rf=0.15.

$^1$H NMR δ (ppm): 2.3 (s, 3H); 2.8 (s, 3H); 3.0–3.1 (m, 1H); 3.2–3.3 (m, 1H); 3.85–3.95 (m, 4H); 4.6–4.7 (m, 1H); 7.0 (s, 1H); 7.1 (s, 1H); 7.3 (s, 1H); 7.35–7.6 (m, 5H); 8.0 (d, 1H); 8.2 (d, 1H); 8.3 (s, 1H).

IR: 3400, 1730, 1675, 1585, 1435, 1280, 1240, 760, 700 cm$^{-1}$.

Example 7B 2-methyl-3-(9-methyl-4-oxo-1-phenyl-3,4,6,7-tetrahydro-1,4]diazepino[6,7,1-hi]indol-3-yl)-4-oxo-3,4-dihydroquinazoline-7-carboxylic acid. Same product as Ex. 7: (I); A=CH$_3$, Z=CH, B=CH$_3$, X$_1$=H, X$_2$=CO$_2$H at 7 (process D1b)

1.3 g (2.6 mmol) of the product of Example 7A are dissolved in 100 ml of TBE; 20 ml of water containing 0.35 g of potassium hydroxide are added and the mixture is stirred at room temperature for 5 h. Ice is added and the mixture is acidified to pH=2. A yellow precipitate is filtered off, which is purified as in Example 7. 0.75 g (60%) obtained.

Example 7C

Salt of 2-methyl-3-(9-methyl-4-oxo-1-phenyl-3,4,6,7-tetrahydro[1,4]diazepino[6,7,1-hi]indol-3-yl)-4-oxo-3,4-dihydroquin azoline-7-carboxylic acid with D-glucamine.

The acid of Example 7B is refluxed in 80 ml of methanol, 0.2 g (0.417 mmol), the suspension almost completely dissolves. 0.076 g of D-glucamine (0.417 mmol) is added. The entire mixture dissolves on refluxing. It is left to cool, the solvent is evaporated off and the product is crystallized from ethanol. HPLC (ODH column thermostatically adjusted to 37° C., 1 mlmin, eluent (%): 94.9 hexane/5 ethanol/0.1 trifluoroacetic acid. 140 mg are obtained (Yld: 51%).

TLC (D/MN20): Rf=0.45.

Example 7D (3R)-2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylic acid (I); A $CH_3$, Z=CH, B=$CH_3$, $X_1$=H, $X_2$=$CO_2H$ at 7, 3R isomer.

500 mg (1.04 mmol) of the racemic acid of Example 7B in 60 ml of ethanol are stirred at reflux. 349 mg (1.04 mmol) of (−)-strychnine are added portionwise. Everything dissolves. The mixture is left for 48 h at room temperature, and 490 mg of the salt of the 3R acid are separated out with an enantiomeric excess of 70% (ee=70%). The salt crystals are recrystallized from 35 ml of ethanol. 350 mg (ee=99%) are obtained. In order to obtain the pure acid, the salt is stirred in a mixture of $CH_2Cl_2$ and 0.1 N hydrochloric acid, the aqueous phase is separated out after settling has taken place and the $CH_2Cl_2$ is washed three times with 10 ml of 0.1 N hydrochloric acid. The product is chromatographed by HPLC on a Chiralcel ODH column, eluting with a 94.9 hexane/5 ethanollO. 1 trifluoroacetic acid (%) mixture.

Example 7E (3S)-2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylic acid. (I); A $CH_3$, Z=CH, B=$CH_3$, $X_1$=H, $X_2$=$CO_2H$ at 7, 3S isomer.

3 g (6.26 mmol) of the racemic acid of Example 7B in 600 ml of methanol are stirred at reflux. 2.096 g (6.26 mrnol) of (−)-strychnine are added portionwise. Insoluble material remains, which is filtered off. 1.6 g of the (R) salt are obtained with an ee=77%. The mixture is left for 48 h at room temperature, and 2.25 g of the (S) salt are separated out with an enantiomeric excess of 60% (ee=60%). 2.25 g of the (S) salt are heated in 100 ml of ethanol. 1.2 g of (S) salt (ee=97.5%) are obtained. In order to obtain the pure acid, the salt is stirred in a mixture of $CH_2Cl_2$ and 0.1 N hydrochloric acid, the aqueous phase is separated out after settling of the phases has taken place and the $CH_2Cl_2$ is washed three times with 10 ml of 0.1 N hydrochloric acid. The product is chromatographed by HPLC on a Chiralcel ODH column, eluting with a 94.9 hexane/5 ethanol/0. 1 trifluoroacetic acid (%) mixture.

Example 8

2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-7-carboxamide. (I); A=$CH_3$, Z=CH, B=$CH_3$, $X_1$=H, $X_2$=$CONH_2$ at position 7 (process D5.b)

0.5 g (1.04 mmol) of the compound of Example 7 is introduced into a reactor protected from moisture, and 1.14 mmol of oxalyl chloride in 2M solution in $CH_2Cl_2$ are added. One drop of dimethylformamide is added and the mixture is left stirring for 16 hours at 20–25° C. The solvents are evaporated off, the residue is taken up twice in succession with benzene which is then evaporated off, thereafter 10 ml of 28% aqueous ammonia are added and the mixture is left stirring again for 16 hours. It is extracted with $CH_2Cl_2$, the organic phases are evaporated and the residue is purified by flash chromatography, first on a silica column, performing elution with ethyl acetate, and then on a so-called reverse-phase column, eluting with a 60:40 v/v water/acetonitrile mixture. The fractions determined pure are pooled and evaporated, and 0.20 g of purified product is obtained in amorphous formn.

Yld=40%—TLC (Ea): Rf=0.20.

$^1$H NMR δ (ppm): 2.3 (s, 3H); 2.85 (s, 3H); 3.1 (m, 1H); 3.35 (m, 1H); 4.0 (q, 1H); 4.7 (t, 1H); 6.0 (s, 1H); 6.1 (s, 1H); 7.0–7.6 (m, 8H); 7.9 (d, 1H); 8.1 (s, 1H); 8.25 (d, 1H)

Example 8A 2-methyl-3-(9-methyl-4-oxo-1-phenyl-3,4,6,7-tetrahydro[1,4]diazepino[6,7,1-h]indol-3-yl)-4oxo-3,4dihydroquinazoline-7-carbonitrile. (I); A=$CH_3$, Z=CH, B=$CH_3$, $X_1$=H, $X_2$=CN, at 7 (process D6).

1.5 g (3.1 mmol) of the product of Example 8 are dissolved in 100 ml of $CH_2Cl_2$ and 2.24 g (9.4 mmol) of Burgess reagent are added. The mixture is left for 4 h at 20–25° C., washed with 30 ml of water, then with normal hydrochloric acid and finally with water. The resulting solution is dried, the solvent is evaporated off and the residue is chromatographed. 1.1 g of a beige-colored solid are obtained. Yld=76%—TLC (DM1): Rf=0.38.

$^1$H NMR δ (ppm): 2.3 (s, 3H); 2.75 (m, 3H); 3.05 (m, 1H); 3.3 (m, 1H); 3.9 (m, 1H); 4.55 (m, 1H); 7.95 (m, 1H); 7.0 (m, 1H); 7.3–7.55 (m, 7H); 7.9 (m, 1H); 8.2 (m, 1H).

Example 8B 9-methyl-3–12-methyl-4-oxo-7-(1H-tetrazol-5-yl)-4H-quinazolin-3-yl]-1-phenyl-6,7-dihydro-3H-[1,4]diazepino [6,7,1-hi]indol-4-one. (I); A=$CH_3$,Z=CH, B=$CH_3$, $X_1$=H, $X_2$=$CN_4H$ at 7 (process D7).

0.86 g (1.8 mmol) of the product of Example 8 are dissolved in 19 ml of DMF and 0.18 g (2.8 mmol) of sodium azide and 0.15 g (2.8 mmol) of ammonium chloride are added. The mixture is heated at 120° C. for 32 h and every 8 h fresh additions of the same amounts of sodium azide and ammonium chloride are carried out. When the starting material has disappeared, the mixture is evaporated and the residue is washed with 30 ml of water in the presence of $CH_2Cl_2$. The organic phase is dried, evaporated and chromatographed. 0.24 g of a beige-colored solid is obtained. Yld=25%.—M.p.=287° C.—TLC (DM20): Rf=0.33.

$^1$H NMR δ (ppm): 2.35 (s, 3H); 2.7 (s, 3H); 3.15 (m, 1H); 3.35 (m, 1H); 3.95 (m, 1H); 4.55 (m, 1H); 6.95 (m, 1H); 7.05 (m, 1H); 7.4–7.6 (m, 7H); 8.15 (m, 2H); 8.25 (s, 1H).

IR: 3300, 1670, 1620, 1580, 1560, 1440, 1380, 1350, 1290, 1270, 1230, 1170, 770, 690 cm$^{-1}$.

Example 9

2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-7-(N-methylcarboxamide). (I); A=$CH_3$, Z=CH,B=$CH_3$, $X_1$=H, $X_2$=CONH—$CH_3$ at position 7 (process A1c)

The compound is prepared as described in Example 8, carrying out the amidation with a solution of methylamine in $CH_2Cl_2$. The product after chromatographic purifications is obtained in amorphous form and is beige in color. Yld=25% TLC (Ea): Rf=0.27.

¹H NMR δ (ppm): 2.4 (s, 3H); 2.8 (s, 3H); 3.0 (d, 3H); 3.1 (m, 1H); 3.3 (m, 1H); 4.0 (q, 1H); 4.7 (q, 1H); 6.0 (s, 1H); 6.4 (d, 1H); 7.0–7.6 (m, 8H); 7.9 (d, 1H); 8.0 (s, 1H); 8.2 (d, 1H).

Example 9A 2-methyl-3-(9-methyl-4-oxo-1-phenyl-3,4,6,7-tetrahydro[1,4]diazepino[6,7,1-hi]indol-3-yl)-4-oxo-3,4dihydroquinazoline-7-N-dimethylcarboxamide.
(I); A=CH₃, Z=CH, B=CH₃, X₁=H, X₂=CON(CH₃)₂ at 7 (process D5b)

The compound is prepared as described in Example 8, the amidation being carried out by a solution of dimethylamine in CH₂Cl₂. The product, after chromatographic purifications, is obtained in the form of a yellow powder. Yld=35%. M.p.=162–165° C. TLC (DM2): Rf=0.15.

¹H NMR δ (ppm): 2.35 (s, 3H); 2.7 (s, 3H); 2.9 (s, 3H); 3.15 (m, 1H); 3.4 (m, 1H); 4.0 (q, 1H); 4.55 (t, 1H); 6.95 (s, 1H); 7.05 (s, 1H); 7.4–7.6 (m, 7H); 7.65 (s, 1H); 8.1 (d, 1H).

IR: 2900; 1670; 1640; 1580; 1380; 1230; 1170; 1070; 700 cm⁻¹.

Example 9B 2-methyl-3-(9-methyl-4-oxo-1-phenyl-3,4,6,7-tetrahydro[1,4]diazepino[6,7,1-hi]indol-3-yl) 4-oxo-3,4-dihydroquinazoline-7-carboxylic acid (2-morpholin-4-yl-ethyl)amide.
(I); A=CH₃, Z=CH, B=CH₃, X₁=H, X₂=CONH(CH₂)₂N-morpholine at 7. (process D5b)

The compound is prepared as described in Example 9C below, the amidation of the product of Example 7B being carried out by a solution of 2-morpholin-4-ylethylamine in CH₂Cl₂. The product after chromatographic purifications is obtained in the form of a yellow powder.

Yld=69%. M.p.=191° C.—TLC (DM7): Rf=0.5.

¹H NMR δ (ppm): 2.3 (s, 3H); 2.5 (t, 4H); 2.6 (t, 2H); 2.75 (s, 3H); 3.0 (m, 1H); 3.3 (m, 1H); 3.6 (q, 2H); 3.7 (t, 4H); 3.9 (q, 1H); 4.6 (m, 1H); 6.9–7.1 (t, 1H) (2s, 2H); 7.2–7.5 (m, 6H); 7.8 (d, 1H); 7.9 (s, 1H); 8.2 (d, 1H).

IR: 3300; 2900; 1670; 1580; 1440; 1380; 1290; 1230; 1100; 860; 725; 700 cm⁻¹.

Example 9C 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylic acid (3-(morpholin-4-ylpropyl)amide.
(I); A=CH₃, Z=CH, B=CH₃, X₁=H, X₂=CONH(CH₂)₃N-morpholine at 7 process D5b)

0.8 g (1.67 mmol) of the racemic acid described in Example 7 and then 0.6 g (1.84 mmol) of TOTU in 20 ml of CH₂Cl₂ are introduced into a 50 ml round-bottomed flask protected from moisture and under a nitrogen atmosphere. The medium is cooled in an ice bath and 0.43 g (1.84 mmol) of DIEA is added. The mixture is stirred for 1 min at 0° C. and 0.24 g (1.67 mmol) of 3-morpholin-4-ylpropylamine is added, after which the mixture is stirred for 16 h at room temperature. The mixture is washed with 1 N HCl and then with saturated NaUCO₃. It is dried over Na₂SO₄ and the solvent is evaporated off. The product after chromatographic purification is obtained in the form of a pale yellow powder. Yld=70%.—M.p.=140° C.—TLC (DM10): Rf=0.63.

¹H NMR δ (ppm): 1.7 (t, 2H); 2.3 (s, 3H); 2.5 (m, 6H); 2.7 (s, 3H); 3.1 (m, 1H); 3.3 (m, 3H); 3.6 (m, 4H); 4.0 (q, 1H); 4.6 (t, 1H); 6.9 (s, 1H); 7.05 (s, 1H); 7.5 (m, 6H); 7.9 (d, 1H); 8.2 (m, 2H); 8.8 (t, 1H).

Example 9D 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-(2-amino)ethylcarboxamide.
(I); A=CH₃, Z=CH, B=CH₃, X₁=H, X₂=CONH(CH₂)₂NH₂ at 7 (process D5b)

The compound is prepared as described in Example 9C, the amidation being carried out by a solution of 2-aminoethylanine in CH₂Cl₂. The product after chromatographic purifications is obtained in the form of a beige-colored powder. Yld=21%.—M.p.=162–165° C. TLC (DMN20): Rf=0.47.

¹H NMR δ (ppm): 2.2 (s, 3H); 2.7 (s, 3H); 3 (m, 3H); 3.2 (m, 1H); 3.5 (q, 2H); 3.9 (q, 1H); 4.6 (t, 1H); 6.95 (s, 1H); 6.9 (s, 1H); 7 (s, 1H); 7.2–7.5 (m, 7H); 7.9 (d, 1H); 8.1 (s, 1H); 8.15 (d, 1H).

Example 9E

The hydrochloride of the product 9D above is prepared in isopropanol, by adding a 15 solution of hydrochloric acid in the same solvent. Yld=77%. The salt crystallizes with 2.5 molecules of water of solvation.

Example 9F

3-{7-[4-(2-hydroxyethyl) piperazine-1-carbonyl]-2-methyl-4-oxo-4H-quinazolin-3-yl}-9-methyl-1-phenyl-6,7-dihydro-3H-[1,4]diazepino[6,7,1-hi]indol-4-one.
(I); A=CH₃, Z=CH, B=CH₃, X₁=H, X₂=CON[(CH₂)₂]₂N(CH₂)₂OH at 7 (process D5b)

The compound is prepared as described in Example 9C, the amidation being carried out with a solution of 1-(2-hydroxyethyl)piperazine in CH₂Cl₂. The product after chromatographic purifications is obtained in the form of a white powder. Yld=71%. TLC (DM10): Rf=0.6.

¹H NMR δ (ppm): 2.3 (s, 3H); 2.4 (m, 6H); 2.7 (s, 3H); 3.1 (m, 1H); 3.3 (m, 3H); 3.55 (q, 2H); 3.65 (m, 2H); 4 (q, 1H); 4.5 (t, 1H); 4.6 (t, 1H); 6.95 (s, 1H); 7.05 (s, 1H); 7.5 (m, 8H); 8.1 (d, 1H).

Example 9G

The hydrochloride of product 9F above is prepared in isopropanol, by adding a solution of hydrochloric acid in the same solvent. Yld=83%. The salt crystallizes with 2.5 molecules of water of solvation.

Example 9H

Methyl (2S)-6-t-butoxycarbonylamino-2-{12-methyl-3-(9-methyl-4-oxo-1-phenyl-3,4,6,7-tetrahydro[1,4]diazepino[6,7,1-hi]indol-3-yl)-4-oxo-3,4-dihydroquinazolin-7-carbonyl]amino}hexanoate. (I); A=CH₃, Z=CH, B=CH₃, X₁=H,

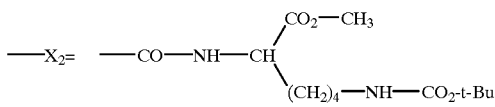

(at 7) (process D5b)

The compound is prepared as described in Example 9C, the amidation being carried out by a solution of methyl (2S)-2-amino-6-t-butoxycarbonylaminohexanoate (methyl Nε-t-BOC-(L)-lysinate) in CH₂Cl₂. The product after chromatographic purifications is obtained in the form of a beige-colored powder. Yld=93%.—TLC (DMN5): Rf=0.65.

Example 9I

Methyl (2S)-6-amino-2-{[2-methyl-3-(9-methyl-4-oxo-1-phenyl-3,4,6,7-tetrahydro-[1,4]diazepino[6,7,1-hi]indol-3-yl)-4-oxo-3,4-dihydroquinazolin-7-carbonyl]amino}hexanoate (process D5b).
(I); A=CH₃, Z=CH, B=CH₃, X₁=H, X₂=CONHCH[(CH₂)₄]NH₂]COOCH₃ at 7

The compound is prepared from the product of Example 9H, by dissolving 0.7 g (0.971 mmol) in 17 ml of CH$_2$Cl$_2$ and by adding to the mixture 3.8 ml of trifluoroacetic acid dropwise. After 2 h at 20–25° C., an examination by TLC no longer allows the starting material to be detected. The mixture is evaporated; after chromatographic purifications, 0.48 g of product is obtained in the form of a white powder. Yld=81%. M.p.=190° C.—TLC (DM10): Rf=0.32.

$^1$H NMR δ (ppm): 1.4 (m, 2H); 1.6 (m, 2H); 1.8 (q, 2H); 2.3 (s, 3H); 2.65 (d, 3H); 2.8 (m, 2H); 3.2 (m, 2H); 3.4 (m, 1H); 4 (q, 1H); 4.5 (m, 2H); 6.9 (s, 1H); 7 (s, 1H); 7.4–7.6 (m, 6H); 7.9 (d, 1H); 8.1–8.2 (2s, Id, 3H); 9.1 (d, 1H).

IR: 3300; 3000; 1680; 1420; 1200; 1120; 790; 720; 690 cm$^{-1}$.

Example 10

2-(4-morpholinyl)ethyl 2-methyl-3-(9-methyl-4-oxo-1-phenyl-3,4,6,7-tetrahydro-[1,4]diazepino-[6,7,1-hi]indol-3-yl)-4-oxo-3,4-dihydroquinazoline-7-carboxylate.

(I); A=CH$_3$, Z=CH, B=CH$_3$, X$_1$=H,

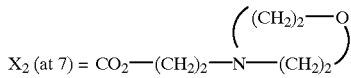

(Process D4a).

In a reactor protected from moisture, 0.3 g (0.63 mmol) of the acid obtained in Example 7 is introduced into 15 ml of sieve-dried DMF, and 0.2 g (1.25 mmol) of carbonyldiimidazole is added. The solution is stirred for 20 h at 20–25° C., 0.246 g (1.88 mmol) of (hydroxyethyl)morpholine is then added and the mixture is heated for 4 h to 60–70° C. After it has returned to approximately 200C, 75 ml of water are added and the mixture is extracted with 3 times 20 ml of ethyl acetate. The combined organic phases are washed with water and dried and the solvents are then removed. The residue is purified by flash chromatography on a silica column; elution with the solvent D/MN2 enables 0.08 g of purified product to be obtained in amorphous form. Yld= 21.5%—TLC (D/MN5): Rf=0.50.

$^1$H NMR δ (ppm): 2.3 (s, 3H); 2.55 (m, 4H); 2.7–2.8 (m, 5H); 3.0–3.1 (m, 1H); 3.25–3.35 (m, 1H); 3.7 (m, 4H); 3.85–4.0 (m, 1H); 4.45 (t, 2H); 4.65–4.7 (m, 1H); 6.0 (s, 1H); 7.1–7.55 (m, 8H); 8.0 (d, 1H); 8.2 (d, 1H); 8.3 (s, 1H);

IR: 3400, 2900, 1720, 1670, 1580, 1560, 1430, 1290, 1240, 1115, 760, 700 cm$^{-1}$

Example 10A 2-acetoxyethyl 2-methyl-3-(9-methyl-4-oxo-1-phenyl-3,4,6,7-tetrahydro[1,4]diazepino[6,7,1-hi]indol-3-yl)-4-oxo-3,4dihydroquinazoline-7-carboxylate (I); A=CH$_3$, Z=CH, B=CH$_3$, X$_1$=H, X$_2$=CO$_2$—(CH$_2$)$_2$—OCOCH$_3$ at 7. (Process D4a)

The compound is prepared as described in Example 10, the esterification being carried out with 2-acetoxyethanol. The product, after chromatographic purifications, is obtained in amorphous form and in a beige color. Yld=36%. M.p.=115–118° C.—TLC (DtMN2): Rf=0.9.

$^1$H NMR δ (ppm): 2.1 (s, 3H); 2.4 (s, 3H); 2.75 (s, 3H); 3.2 (m, 1H); 3.45 (m, 1H); 4 (q, 1H); 4.5 (m, 2H); 4.6 (mn, 3H); 7 (s, 1H); 7.1 (s, 1H); 7.5–7.6 (m, 6H); 8.05 (d, 1H); 8.2 (s, 1H); 8.3 (d, 1H).

IR: 3400, 2900, 1740, 1680, 1580, 1560, 1430, 1290, 1240, 760 cm$^{-1}$.

Example 10B

2-Methoxyethyl 2-methyl-3-(9-methyl-4-oxo-1-phenyl-3,4,6,7-tetrahydro[1,4]diazepino[6,7,1-hi] indol-3-yl)-4-oxo-3,4-dihydroquinazoline-7-carboxylate (I); A=CH$_3$, Z=CH, B=CH$_3$, X$_1$=H, X$_2$=CO$_2$—(CH$_2$)$_2$—OCH$_3$ at 7. (Process D4a)

The compound is prepared as described in Example 10, the esterification being carried out with 2-methoxyethanol. The product, after chromatographic purification, is obtained in amorphous form. Yld=17%. M.p.=108–111°° C.—TLC (D/MN2): Rf=0.17.

$^1$H NMR δ (ppm): 2.4 (s, 3H); 2.7 (s, 3H); 3.25 (m, 1H); 3.4 (m, 1H); 3.8 (m, 2H); 4.1 (q, 1H); 4.5 (m, 2H); 4.6 (t, 3H); 7 (s, 1H); 7.55 (t, 2H); 7.65 (m, 4H); 8.1 (d, 1H); 8.25 (s, 1H); 8.3 (d, 1H).

IR: 3400, 2850, 1720, 1680, 1580, 1560, 1380, 1290, 1240, 1100, 760, 690 cm$^{-1}$.

Example 10C

2-Hydroxyethyl 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylate.

(I); A=CH$_3$, Z=CH, B=CH$_3$, X$_1$=H, X$_2$=CO$_2$—(CH$_2$)$_2$-OH at 7. (Process D4.a)

The compound is prepared as described in Example 10, the esterification being carried out with ethylene glycol. The product, after chromatographic purification, is obtained in the form of a beige powder. Yld=47%. M.p.=257–259° C.—TLC (D/MN2): Rf=0.39.

$^1$H NMR δ (ppm): 2.35 (s, 3H); 2.7 (s, 3H); 3.2 (m, 1H); 3.4 (m, 1H); 3.75 (m, 2H); 4.0 (q, 1H); 4.4 (m, 2H); 4.6 (t, 1H); 5 (t, 1H); 6.95 (s, 1H); 7.05 (s, 1H); 7.4–7.6 (m, 7H); 8.05 (d, 1H); 8.2 (d, 1H); 8.25 (s, 1H).

Example 10D 1-(2S)-glyceryl 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylate.

(I); A=CH$_3$, Z=CH, B=CH$_3$, X$_1$=H, X$_2$=CO$_2$—CH$_2$CHOHCH$_2$-OH at 7. (Process E1a)

0.3 g of racemic acid of Example 7B (0.626 mmol), 46 mg of (S)-glycidol and 20 mg of tetrabutylammonium bromide are suspended in 30 ml of toluene. The mixture is refluxed for 2.5 h. At the end of the reaction, everything is dissolved. The mixture is evaporated. The products, after chromatographic purification, is obtained (120 mg) in the form of a beige powder.

Yld=47%.—M.p.=170–175° C.—TLC (D/MN1O): Rf=0.42.

$^1$H NMR δ (ppm): 2.3 (s, 3H); 2.65 (m, 1H); 2.8 (s, 3H); 3.3–3.35 (m, 3H); 3.65–3.8 (m, 2H); 3.85–4.1 (m, 2H); 4.35–4.5 (m, 2H); 4.6–4.7 (m, 1H); 7.0–7.55 (m, 8H); 7.95 (d, 1H); 8.2 (d, 1H); 8.35 (s, 1H).

IR: 3400, 2900, 1720, 1670, 1580, 1560, 1430, 1290, 1240, 1100, 760, 690 cm$^{-1}$.

Example 10E 2-hydroxy-3-morpholin-4-ylpropyl 2-methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxylate. (Process E)

(I); A=CH$_3$, Z=CH, B=CH$_3$, X$_1$=H, X$_2$=CO$_2$—CH$_2$CHOHCH$_2$-4-morpholine at 7.

The compound is prepared as described in Example 10, the esterification being carried out with 1,2-epoxy-3-N-morpholinylpropane. The product, after chromatographic purification, is obtained in the form of a powder. Yld= 56%.—M.p.=135–140° C.—TLC (D/MN3): Rf=0.35.

$^1$H NMR δ (ppm): 2.3 (s, 3H); 2.4–2.7 (m, 6H); 2.8 (s, 3H); 3–3.1 (m, 1H); 3.25–3.35 (m, 1H); 3.4–3.5 (s, 1H); 3.6–3.7 (m, 4H); 3.85–3.95 (m, 1H); 4 (m, 1H); 4.25–4.40 (m, 2H); 4.6–4.7 (m, 1H); 7.0 (s, 1H); 7.1 (s, 1H); 7.2 (s, 1H); 7.25 (s, 1H); 7.3–7.5 (m, 4H); 7.95 (d, 1H); 8.2 (d, 1H); 8.3 (s, 11H).

IR: 3500, 2950, 2800, 1720, 1680, 1580, 1560, 1430, 1290, 1240, 1115, 760, 700 cm$^{-1}$.

Example 11

3-(7-hydroxymethyl-2-methyl-4-oxo-4H-quinazolin-3-yl)-9-methyl-1-phenyl-6,7-dihydro-3H-[1,4]diazepino[6,7,1-hi]indol-4-one.

(I); A=CH$_3$, Z=CH, B=CH$_3$, X$_1$=H, X$_2$=CH$_2$OH at position 7 (process D2b)

In a reactor protected from moisture, 0.53 g (1.1 mmol) of the acid obtained in Example 7 is introduced into 10 ml of sieve-dried THF, and then, after the mixture has been cooled to 0° C., 0.17 ml of ethyl chloroformate and 0.17 ml of triethylamine are introduced. The mixture is stirred for 2 h at 0° C. and the insoluble matter is then filtered off and discarded. 0.5 g of sodium borohydride dissolved in 0.5 ml of THF is added to the filtrate and the mixture is then kept stirring for 3 h at 0° C. The solvents are removed by distillation and the residual product is purified by flash chromatography on a silica column. Elution with an ethyl acetate/cyclohexane mixture enables the product to be obtained in amorphous form. Weight: 0.08 g—Yld= 15.6%—TLC (D/M5): Rf=0.60.

$^1$H NMR δ (ppm): 2.4 (s, 3H); 2.7 (s, 3H); 3.2 (m, 1H); 3.45 (m, 1H); 4.0 (m, 1H); 4.6 (t, 1H); 4.7 (d, 2H); 5.5 (t, 1H); 7.0 (s, 1H); 7.1 (s, 1H); 7.4–7.6 (m, 7H); 7.65 (s, 1H); 8.1 (d, 1H).

IR: 3400, 2900, 1660, 1620, 1580, 1560, 1440, 1380, 1230, 1170, 1120, 780, 740, 650 cm$^{-1}$

Example 12

(3S)-3-(5-fluoro-2-methyl-4-oxo-4H-quinazolin-3-yl)-9-methyl-1-phenyl-6,7-dihydro-3H-1 1,4]diazepino[6,7,1-hi]indol-4-one.

(I); A=CH$_3$, Z=CH, B=CH$_3$, X$_1$=H, X$_2$=F at position 5 (process A1c)

2-Acetylamino-6-fluorobenzoic acid is prepared as described in Example 3 from 2-amino-6-fluorobenzoic acid, and the compound in the title is then prepared according to the procedure described in Example 3.

Yld=26%—white solid—M.p.=238° C.—["]$_D$=21E (c=1, CH$_2$Cl$_2$)—TLC (D/M2): Rf=0.40

$^1$H NMR δ (ppm): 2.3 (s, 3H); 2.85 (s, 3H); 3.05 (m, 1H); 3.3 (m, 1H); 3.9 (q, 1H); 4.65 (t, 1H); 7.3 (m, I 1H).

Example 13

3-(5-chloro-2-methyl-4-oxo-4H-quinazolin-3-yl)-9-methyl-1-phenyl-6,7-dihydro-3H-[1,4]diazepino-[6,7,1-hi]indol-4-one.

(I); A=CH$_3$, Z=CH, B=CH$_3$, X$_1$=H, X$_2$=Cl at position 5. (process A1c)

This compound is prepared from 2-amino-6-chlorobenzoic acid according to the procedure described in Example 3.

Yld: 39%—white solid—M.p.=222° C.—TLC (D/M2): Rf=0.48

$^1$H NMR δ (ppm): 2.35 (s, 3H); 2.8 (s, 3H); 3.1 (m, 1H); 3.4 (m, 1H); 3.95 (q, 1H); 4.7 (t, 1H); 7.05 (s, 1H); 7.15 (s, 1H); 7.3 (s, 1H); 7.5 (m, 8H).

Example 14 ethyl 3-(9-methyl-4-oxo-1-phenyl-3,4,6,7-tetrahydro-[1,4]diazepino[6,7,1-hi]indol-3-yl)-4-oxo-3,4-dihydroquinazoline-2-carboxylate.

(I); A=CH$_3$, Z=CH, B=—CO$_2$Et, X$_1$=H, X$_2$=H (process A2)

In a reactor under nitrogen and equipped with a CaCl$_2$ guard tube, 200 mg (0.69 mmol) of the intermediate 2.a and 122 mg (0.76 mmol) of ethyl 4-oxo-4H-benzo-[d][1,3]oxazine-2-carboxylate (prepared from N-ethoxalylanthranilic acid according to J. Am. Chem. Soc. 32, 1910, 122) are introduced into 15 ml of toluene dried over molecular sieve. The mixture is stirred for 14 h at 100° C., the solvent is then evaporated off and the residue is purified by flash chromatography on silica, eluting with the solvent C/A20. Weight=0.12 g—Yld: 20%—white solid— M.p.=253° C.—TLC (C/A30): Rf=0.37.

$^1$H NMR δ (ppm): 1.05 (t, 3H); 2.3 (s, 3H); 3.05–3.15 (m, 1H); 3.3–3.4 (m, 1H); 3.7–3.8 (m, 1H); 3.9–4.05 (m, 2H); 4.75–4.85 (m, 1H); 6.6 (s, 1H); 7(s, 1H); 7.3 (s, 1H); 7.4 (t, 2H); 7.5 (d, 1H); 7.55–7.6 (m, 3H); 7.8 (t, 1H); 7.9 (d, 1H); 8.3 (d, 1H)

IR: 3400, 2900, 1740, 1710, 1690, 1590, 1460, 1300, 1230, 1170, 1090, 890, 770, 700 cm$^{-1}$

Example 15

Ethyl 5-chloro-3-(9-methyl-4-oxo-1-phenyl-3,4,6,7-tetrahydro-[1,4]diazepino[6,7,1-hi]indol-3-yl)-4oxo-3,4-dihydroquinazoline-2-carboxylate.

(I); A=CH$_3$, Z=CH, B=—CO$_2$Et, X$_1$=H, X$_2$=Cl at position 5 (process A1.a)

In a reactor protected from moisture, 1.0 g (3.43 imnol) of the intermediate 2, 0.617 g of 2-chloro-6-(ethoxycarbonylamino)benzoic acid and 0.34 ml (3.92 mmol) of phosphorus trichloride are introduced into 20 ml of anhydrous CH$_2$Cl$_2$. The mixture is stirred at 20–25° C. for 18 h and 8.0 ml of 5% aqueous NaHCO$_3$ solution are then added. After a few minutes of stirring, the organic phase is separated and evaporated. The residue is purified by flash chromatography on a silica column. Elution with the solvent DIA5 enables, after evaporation of the fractions determined pure, 0.52 g of amorphous product to be obtained. Yld=29%. M.p.=306° C.—TLC (D/A5): Rf=0.45.

$^1$H NMR δ (ppm): 1.0 (t, 3H); 2.4 (s, 3H); 3.1 (m, 1H); 3.3 (m, 1H); 3.7 (m, 1H); 3.9 (m, 2H); 4.7 (m, 1H); 6.4 (s, 1H), 6.9 (s, 1H); 7.2–7.8 (m, 9H).

IR: 3300, 3000, 1630, 1580, 1450, 1380, 1340, 1280, 1140, 1100, 820, 780, 700 cm$^{-1}$

Example 16

Ethyl [3-(9-methyl-4-oxo-1-phenyl-3,4,6,7-tetrahydro-[1,4]diazepino[6,7,1-hi]indol-3-yl)-4-oxo-3,4-dihydro-2-quinazolinyl]acetate. (I); A=CH$_3$, Z=CH, B=CH$_2$—CO$_2$Et, X$_1$=H, X$_2$=H. (process A3)

In a reactor protected from moisture, according to a process similar to Example 15, the intermediate 2 and a 60/40 mixture of ethyl (4-oxo-4H-benzo-[d][1,3]oxazin-2-yl)acetate and 2-(2-ethoxycarbonylacetylamino)benzoic acid, obtained by reacting anthranilic acid with ethyl (chlorocarbonyl)acetate, are reacted in CH$_2$Cl$_2$ in the presence of ttiethylamine according to a method adapted from Tetrahedron Lett. 50 (1994) 34, 10331. The product is purified by flash chromatography on a silica column, eluting with the solvent C/A20. Yld=26%—M.p.=228–230° C.—TLC (C/A30): Rf=0.30

$^1$H NMR δ (ppm): 0.75 (t, 3H); 2.3 (s, 3H); 3.1 (m, 1H); 3.3 (s,2H); 3.4 (m, 1H); 3.5 (m, 1H); 3.8 (m, 3H); 4.0 (q, 1H); 4.55 (t, 1H); 6.85 (s, 1H); 6.95 (s, 1H); 7.45 (m, 4H); 7.55 (m, 3H); 7.7 (s, 1H); 7.9 (m, 1H); 8.15 (s, 1H)

IR: 3400, 2900, 1740, 1670, 1590,1570, 1470, 1390, 1330, 1300, 1230, 1200, 1150, 770, 710 cm$^{-1}$

Example 17

Methyl 3-(9-methyl-4-oxo-1-phenyl-3,4,6,7-tetrahydro-[1,4]diazepino[6,7,1-hi]indol-3-yl)-4-oxo-3,4dihydro-2-quinazolinylacetate. (I); A=CH$_3$, Z=CH, B=CH$_2$—O—CO—CH$_3$, X$_1$=H, X$_2$=H. (process A1a)

In a reactor protected from moisture, according to a process similar to Example 15, the intermediate 2.a and 2-(2-acetoxyacetylamino)benzoic acid, obtained by reacting anthranilic acid with methyl (chlorocarbonyl)acetate, are reacted in $CH_2Cl_2$ in the presence of triethylamine. The product is purified by chromatography on a silica column, eluting with the solvent C/A20. Yld 15%—M.p.=208–210° C.—TLC (C/A30): Rf=0.22.

$^1$H NMR δ (ppm): 2.05 (s, 3H); 3.1 (m, 1H); 3.35 (m, 1H); 3.4 (m, 1H); 4.0 (q, 1H); 4.55 (t, 1H); 4.9 (d, 1H); 5.6 (d, 1H); 6.85 (s, 1H); 7.5 (m, 7H); 7.75 (d, 1H); 8.15 (d, 1H); 8.95 (t, 1H)

IR: 3400, 1760, 1690, 1670, 1600, 1560, 1400, 1220, 1180, 780, 700 $cm^{-1}$

Example 17A

9-Methyl-3-(2-methyloxymethyl-4-oxo-4H-quinazolin-3-yl)-1-phenyl-6,7-dihydro-3H-[1,4]diazepino[6,7,1-hi]indol-4-one. (I); $A=CH_3$, $Z=CH$, $B=CH_2OCH_3$, $X_1=H$, $X_2=H$ (process A12c).

In the same way as in Example 2A, starting with the intermediate racemic amine 2.a and 2-methoxyacetylaminobenzoic acid, and after chromatographic purification, the product is obtained in the form of a powder (Yld=17%).—M.p.=220° C.—TLC (DA5): Rf=0.15.

$^1$H NMR δ (ppm): 2.3 (s, 3H); 3.1 (m, 11H); 3.2 (s, 3H); 3.4 (m, 1H); 3.65 (d, 1H); 3.9 (q, 1H); 4.4 (d, 1H); 4.55 (dd, 11H); 4.7 (d, 11H); 6.85 (s, 1H); 7.05 (s, 11H); 7.2 (d, 1H); 7.5 (m, 7H); 7.9 (t, 1H); 8.1 (d, l1H).

IR: 3400, 2900, 1670, 1590, 1470, 780, 700 $cm^{-1}$.

Example 17B

9-Methyl-3-(2-hydroxymethyl-4-oxo-4H-quinazolin-3-yl)-1-phenyl-6,7-dihydro-3H-[1,4]diazepino[6,7,1-hi]indol-4-one. (I); $A=CH_3$, $Z=CH$, $B=CH_2OH$, $X_1=H$, $X_2=H$ (process A12c).

In the same way as in Example 7B, starting with the product of Example 17, and after chromatographic purification, a powder is obtained (Yld=67%).

$^1$H NMR δ (ppm): 2.3 (s, 3H); 3.1 (m, 11H); 3.4 (m, 11H); 4.0 (m, 11H); 4.4 (q, 1H); 4.6 (t, 11H); 4.8 (d, 1H); 5.05 (m, 1H); 6.9 (s, 1H); 7.0 (s, 1H); 7.5 (m, 7H); 7.7 (d, 1H); 7.9 (m, 1H); 8.1 (d, 1H).

IR: 3400,1680,1580, 1560, 780,700 $cm^{-1}$.

Example 17C

[3-(9-Methyl-4-oxo-1-phenyl-3,4,6,7-tetrahydro-[1,4]diazepino[6,7,1-hi]indol-3-yl)-4-oxo-3,4-dihydroquinazolin-2-yl]methyl hydrogen succinate (I); $A=CH_3$, $Z=CH$, $B=CH_2OCO(CH_2)_2COOH$, $X_1=H$, $X_2=H$ (process A13c).

Starting with 0.750 g (1.06 mmol) of the product of Example 17B in 20 ml of $CH_2Cl_2$, 0.183 g (1.83 mmol) of succinic anhydride and 0.203 g of triethylamine (2 mmol) are added with stirring. After stirring for 4 h at room temperature, the mixture is evaporated and the residue is chromatographed on silica in DM5. 580 mg of powder are obtained. Yld=63%.

$^1$H NMR δ (ppm):2.3 (s, 3H); 2.4 (m, 2H); 2.6 (m, 2H); 3.1 (m, 1H); 3.35 (m, 1H); 4.0 (m, 1H); 4.5 (t, 1H); 4.9 (d, 1H); 5.1 (d, 1H); 6.8 (s, 1H); 7.0 (s, 1H); 7.5 (m, 7H); 7.7 (d, 1H); 7.9 (t, 1H); 8.1 (d, 1H).

IR: 3400, 1740, 1680, 1600, 1160, 780, 700 $cm^{-1}$.

Example 17D

[3-(9-Methyl-4-oxo-1-phenyl-3,4,6,7-tetrahydro-[1,4]diazepino[6,7,1-hi]iondol-3-yl)-4-oxo-3,4-dihydroquinazolin-2-yl]methanol [2-(2-methoxyethoxy)ethoxy]acetate.

(I); $A=CH_3$, $Z=CH$, $B=CH_2OCOCH_2O[(CH_2)_2O]_2CH_3$, $X_1=H$, $X_2=H$ (Process A14c).

Starting with 0.300 g (0.666 mmol) of the product of Example 17B in 20 ml of $CH_2Cl_2$, 0.141 g of triethylamine (1.4 mmol) and then 0.5 g (2.37 mmol) of 3,6,9-trioxadecanoyl chloride are added with stirring. After stirring for 24 h at 20–25° C., the mixture is evaporated, washed with saturated $NaHCO_3$ solution, dried, evaporated and chromatographed on silica in DM10. 285 mg are obtained. Yld=42%.—M.p.=153–155° C.—TLC (DM10): Rf=0.17.

$^1$H NMR δ (ppm): 2.35 (s, 3H); 3.15 (m, 1H); 3.2 (s, 4H); 3.4 (m, 3H); 3.5 (m, 4H); 3.6 (m, 2H); 4.0 (m, 1H); 4.2 (d, 2H); 4.6 (t, 1H); 5.05 (d, 1H); 5.7 (d, 1H); 6.85 (s, 1H); 7.05 (s, 1H); 7.15 (d, 1H); 7.5 (m, 7H); 7.9 (t, 1H); 8.1 (d, 1H).

IR: 3400, 2900, 1760, 1680, 1600, 1140, 1100, 780, 700 $cm^{-1}$.

Example 17E 3-(9-Methyl-4-oxo-1-phenyl-3,4,6,7-tetrahydro-[1,4]diazepino[6,7,1-hi]indol-3-yl)-4-oxo-3,4-dihydroquinazolin-2-ylmethyl N-(2-morpholin-4-ylethyl)succinamate.

(I); $A=CH_3$, $Z=CH$, $B=CH_2OCO(CH_2)_2CONH(CH_2)_2N[(CH_2)_2]_2O$, $X_1=H$, $X_2=H$.

(Process Al 4c).

Starting with 0.400 g (0.73 mmol) of the product of Example 17C in 20 ml of $CH_2Cl_2$, 0.129 g of phosphorus trichloride (0.94 mmol) is added with stirring, the mixture is left for 20 min then 0.113 g (0.87 mmol) of 2-(N-morpholino)ethylamine is added. After stirring for 24 h at 20–25° C., the mixture is evaporated, washed with saturated $NaHCO_3$ solution, dried, evaporated and chromatographed on silica in DM2, then DM3 and then DM5. 0.40 g of powder is obtained. Yld=83%.—TLC (DMN5): Rf=0.22.

$^1$H NMR δ (ppm): 2.35 (m, 11H); 2.6 (m, 2H); 3.15 (m, 3H); 3.4 (m, 1H); 3.4 (m, 1H); 3.5 (m, 4H); 4.0 (q, 1H); 4.5 (t, 1H); 4.9 (d, 1H); 5.6 (d, 1H); 6.9 (s, 1H); 7.1 (s, 1H); 7.5 (m, 7H); 7.7 (m, 2H); 7.9 (m, 1H); 8.1 (d, 1H).

IR: 3400, 2900, 1740, 1680, 1600, 1240, 1160, 1170, 750, 700 $cm^{-1}$.

Example 17F 3-(9-Methyl-4-oxo-1-phenyl-3,4,6,7-tetrahydro-[1,4]diazepino[6,7,1-hi]indol-3-yl)-4-oxo-3,4-dihydroquinazolin-2-ylmethyl 2-morpholin-4-ylethyl succinate.

(I); $A=CH_3$, $Z=CH$, $B=CH_2OCO(CH_2)_2COO(CH_2)_2N[(CH_2)_2]_2O$, $X_1=H$, $X_2=H$. (Process Al5c).

Starting with 0.500 g (0.9 mmol) of the product of Example 17C in 10 ml of $CH_2Cl_2$, 0.15 g of phosphorus trichloride (1.1 mmol) is added with stirring, the mixture is left for 20 min and then 0.12 g (0.99 mmol) of 2-(N-morpholino)ethanol is added. After stirring for 24 h at 20–25° C., the mixture is evaporated, washed with saturated $NaHCO_3$ solution, dried, evaporated and chromatographed, a first time on silica in DMN3 and a second time in DMN1. 0.150 g of a yellow powder is obtained. Yld=25%.—M.p.=95° C.—TLC (DMN5): Rf=0.33.

$^1$H NMR δ (ppm): 2.35 (m, 7H); 2.45–2.55 (m, 4H); 2.6–2.7 (m, 4H); 3.05–3.02 (m, 1H); 3.3–3.45 (m, 1H); 3.5 (m, 4H); 3.9–4.05 (m, 1H); 4.1 (t, 2H); 4.5–4.6 (m, 1H); 4.9–5 (d, 1H); 5.6–5.7 (d, 1H); 6.85 (s, 1H); 7.05 (s, 1H); 7.4–7.65 (m, 7H); 7.7 (d, 1H); 7.9 (t, 1H); 8.1 (d, 1H).

IR: 3450, 2950, 1740, 1670, 1600, 1570, 1300, 1230, 1150, 1110, 1030, 770, 700 $cm^{-1}$.

Example 17G

Methyl 6-t-butoxycarbonylamino-2-{3-[3-(9-methyl-4-oxo-1-phenyl-3,4,6,7-tetrahydro-[1,4]diazepino[6,7,1-hi]indol- 3-yl)-4-oxo-3,4-dihydroquinazolin-2-ylmethoxycarbonyl]propionylamino}hexanoate
(I); A=CH3, Z=CH, B=CH$_2$OCO(CH$_2$)$_2$CONHCH[(CH$_2$)$_4$NHCO$_2$C(CH$_3$)$_3$]CO$_2$CH$_3$, X, H, X$_2$=H (process A15c).

Starting with 0.60 g (1.08 mmol) of the product of Example 17C in 20 ml of CH$_2$Cl$_2$, 0.25 g of phosphorus trichloride (1.85 mmol) is added with stirring; the mixture is left for 20 min and 0.625 g (1.63 mmol) of methyl (N-ε-t-butoxycarbonyl)-(L)-lysinate is then added. After stirring for 24 h at room temperature, the mixture is evaporated, washed with saturated NaHCO$_3$ solution, dried, evaporated and chromatographed in DM1 and then DM2. 0.170 g of a yellow powder is obtained. Yld=25%.—M.p.=95° C.—TLC (DMN5): Rf=0.33.

$^1$H NMR δ (ppm): 1.2 (m, 4H); 1.25 (s, 18H); 1.65 (m, 2H); 1.9 (s, 2H); 2.25 (s, 6H); 2.4 (m, 4H); 2.65 (m, 4H); 3.0 (m, 6H); 3.25 (m, 2H); 3.6 (m, 4H); 3.9 (q, 2H); 4.5 (m, 2H); 4.6 (m, 6H); 5.1 (m, 2H); 5.7 (q, 2H); 6.4 (d, 1H); 6.6 (d, 1H); 7.0 (m, 4H); 7.25–7.5 (m, 14H); 7.7 (s, 4H); 8.1 (d, 2H) mixture of two diastereoisomers.

Example 17H

Ethyl 3-[3-(9-methyl 4oxo-1-phenyl-3,4,6,7-tetrahydro[1,4]diazepino[6,7,1-hi]indol-3-yl)-4-oxo-3,4-dihydroquinazolin-2-yl]propanoate.
(I); A=CH$_3$, Z=CH, B=(CH$_2$)$_2$—CO$_2$Et, X, H, X$_2$=H. (Process A1a)

In the same way as in Example 15, the intermediate 2 is reacted with 2-(3-ethoxycarbonylpropanoylamino)benzoic acid obtained by reaction of anthranilic acid with ethyl 3-chlorocarbonylpropanoate in CH$_2$Cl$_2$ in the presence of triethylamine, according to a method adapted from Tetrahedron Lett. 50 (1994) 34, 10331. The product is purified by flash chromatography on a column of silica, eluting with the solvent C/A30.

Yld=43%.—M.p. 192° C.—TLC (C/A30): Rf=0.44

$^1$H NMR δ (ppm): 1.1 (t, 3H); 2.35 (s, 3H); 2.6–2.75 (m, 1H); 2.8–2.95 (m, 1H); 2.95–3.05 (m, 1H); 3.05–3.2 (m, 1H); 3.3–3.4 (m, 1H); 3.45–3.55 (m, 1H); 3.9–4 (m, 3H); 4.5–4.6 (m, 1H); 6.95 (m, 1H); 7.05 (s, 1H); 7.4–7.5 (m, 2H); 7.5–7.6 (m, 5H); 7.62 (d, 1H); 7.85 (t, 1H); 8.1 d (d, 1H).

IR: 3800, 2900, 1730, 1670, 1590, 1570, 1470, 1390, 1230, 1170, 880, 770, 700, 660 cm$^{-1}$.

Example 18

3(9-Methyl-3-oxo-4H-quinazolin-3-yl)-1-phenyl-6,7-dihydro-3H-[1,4]diazepino[6,7,1-hi]indol-4one (I); A=CH$_3$, Z=CH, B=H, X$_1$=H, X$_2$=H.

200 mg (0.4 mmol) of the product of Example 14, dissolved in 5 ml of methanol containing 5% of KOH, are introduced into a reactor, and the mixture is brought to reflux. After 45 min, the mixture is cooled and acidified with a few drops of concentrated hydrochloric acid. A precipitate forms, which is washed with cold water and purified by flash chromatography on silica, eluting with the solvent D/MNIO. Weight=70 mg. Yld: 41%—yellow solid—M.p.=139° C.—TLC (C/A20): Rf=0.32.

$^1$H NMR δ (ppm): 2.35 (s, 3H); 3.05–3.2 (m, 1H); 3.3–3.45 (m, 1H); 3.94 (m, 1H); 4.4–4.55 (m, 1H); 6.3 (s, 1H); 7.05 (s, 1H); 7.4–7.65 (m, 7H); 7.75 (d, 1H); 7.85–7.95 (t, 1H); 8.15 (d, 1H); 8.7 (s, 1H).

IR: 3400, 2900, 1670, 1610, 1560, 1470, 1380, 1270, 1240, 1160, 880, 780, 700 cm$^{-1}$

Example 19

(3S)-3-(2-Methyl-4-oxo-4H-pyrido[3,4-d]-pyrimidin-3-yl)-9-methyl-1-phenyl-6,7-dihydro-3H-[1,4]diazepino[6,7,1-hi]indol-1-one.
(I); A=CH$_3$, Z=N, B=CH$_3$, X$_1$=H, X$_2$=H (process A1b)

In a reactor protected from moisture and under a nitrogen atmosphere, 0.515 g (2.86 mmol) of 3-acetamidoisonicotinic acid and 0.316 g (3.13 mmol) of N-methylmorpholine are dissolved in 20 ml of CH$_2$Cl$_2$ dried over molecular sieve. The mixture is cooled to 0C and 3.13 mmol of isobutyl chloroformate are added dropwise to the mixture, which is then stirred for 3 h at 0C. 0.833 g (2.86 mmol) of the intermediate amine 2.b of R configuration dissolved in 3 ml of CH$_2$Cl$_2$ is added. The mixture is maintained for 2 h at 0C and then for 12 h at room temperature. The solvent is evaporated off under vacuum and the residue weighing 1.87 g is purified by flash chromatography on a silica column, eluting successively with the solvents D/A4, D/A6, D/M3 and D/M5. The intermediate fractions are pooled and chromatographed again, eluting with the solvent D/M2. The fractions determined pure by TLC are pooled, the solvent is evaporated and 0.07 g of a white foam is obtained.

Yld=5.6%—M.p.=245° C.—ee=97% (HPLC, DNBPG covalent Pirkle column) TLC (D/M5): Rf=0.6

$^1$H NMR δ (ppm): 2.3 (s, 3H); 2.85 (s, 3H); 3.1 (m, 1H); 3.3 (m, 1H); 3.90 (q, 1H); 4.7 (t, 1H); 7–7.6 (m, 8H); 8 (d, 1H); 8.65 (d, 1H); 9.15 (d, 1H).

IR: 3500, 1680, 1580, 1420, 1400, 1260, 1220, 700 cm$^{-1}$.

Example 19A 3-(2-Methyl-4-oxo-4H-pteridin-3-yl)-9-methyl-1-phenyl-6,7-dihydro-3H-[1,4]diazepino[6,7,1-hi]indol-4-one.
(I); A=CH$_3$, Z=CH, Z$_1$=N, Z$_2$=N, B=CH$_3$, X$_1$=H, X$_2$=H. (Process A11c)

The compound is prepared in two steps, using 2.0 g of methyl 3-aminopyrazolecarboxylate, which is refluxed for 6 h in 6.27 g of trimethyl orthoacetate. The volatile products are evaporated and stripped off under high vaccum. The intermediate compound is not purified, and is used directly in the following step. 1.25 g of the amine 2.a in 20 ml of methanol are added and the mixture is refluxed for 16 h under a nitrogen atmosphere. The product is purified by flash chromatography on silica in the mixture D/M1. Mass: 0.30 g.—Yld: 16%—Solid—M.p.=178–183° C.—TLC (D/MN5): Rf=0.44.

$^1$H NMR δ (ppm): 2.3 (s, 3H); 2.85 (s, 3H); 3.0 –3.15 (m, 3H); 3.3–3.4 (m, 1H); 3.85–4.0 (m, 1H); 4.6–4.7 (m, 1H); 7.0–7.5 (m, 8H); 8.7 (s, 1H); 8.9 (s, 1H).

IR: 3400, 2850, 1680, 1580, 1540, 1460, 1430, 1380, 1260, 1210, 1100, 720, 700.

Example 20

3-(2-Methyl-4-oxo-4H-quinazolin-3-yl)-9-nitro-1-phenyl-6,7-dihydro-3H-[1,4]diazepino-[6,7,1-hi]indol-4-one.
(I); A=NO$_2$, Z=CH, B=CH$_3$, X$_1$=H, X$_2$=H (process A1c)

In a reactor protected from moisture and at 0° C., 14.7 g (45.6 mmol) of the intermediate amine 3.a are dissolved with stirring in 250 ml of anhydrous CH$_2$Cl$_2$. At a temperature in the region of 20° C., 9 g (50 mmol) of 2-acetamidobenzoic acid and 14.96 g (45.6 mmol) of OTUT are then added. The mixture is cooled to 0° C. and 11.79 g (91.2 mmol) of DIEA are added. The mixture is maintained for 1 min at 0° C. and then for 12 h at room temperature. 14.96 g of OTUT and 11.79 g of DIEA are then added under the same conditions; the mixture is kept stirring for 1 h and the solvent is then evaporated off under vacuum. The residue is purified by chromatography on silica, eluting with the solvent D/A1 and then D/Al.5. Weight=17 g—Yld: 80%.

$^1$H NMR δ (ppm): 2.75 (s, 3H); 3.25 (m, 1H); 3.45 (m, 1H); 4.05 (m, 1H); 4.7 (m, 1H); 7.2 (s, 1H); 7.35–7.55 (m, 6H); 7.7 (m, 1H); 7.75 (m, 1H); 8.15 (m, 2H); 8.3 (s, 1H).

The products of Examples 21 to 26 are prepared according to the process A1c (Table 1) from the nitro intermediate 3.a and the appropriate substituted 2-acetamidobenzoic acids.

TABLE 1

| | | | | Synthesis | | | | |
|---|---|---|---|---|---|---|---|---|
| Ex. No. | A | Z | B | $X_1$ | $X_2$ | Process | Yld | M.p. | Rf |
| 20 | $NO_2$ | CH | $CH_3$ | H | H | Alc | 75% | — | — |
| 21 | $NO_2$ | CH | $CH_3$ | H | 5-$CH_3$ | Alc | 24% | — | 0.85 (D/M5) |
| 22 | $NO_2$ | CH | $CH_3$ | H | 6-$CH_3$ | Alc | 27% | 250° C. | 0.38 (D/M2) |
| 23 | $NO_2$ | CH | $CH_3$ | H | 7-$CH_3$ | Alc | 30% | 215° C. | 0.36 (D/M2) |
| 24 | $NO_2$ | CH | $CH_3$ | H | 8-$CH_3$ | Alc | 13% | — | 0.47 (D/M2) |
| 25 | $NO_2$ | CH | $CH_3$ | 6-$CH_3$ | 8-$CH_3$ | Alc | 27% | 172° C. | 0.79 (D/M2) |
| 26 | $NO_2$ | CH | $CH_3$ | 6-$CH_3$ | 8-Br | Alc | 2% | — | 0.81 (D/M2) |
| 27 | $NO_2$ | N | $CH_3$ | H | H | B | 44% | — | 0.55 (D/M5) |

Example 21
3-(2,5-Dimethyl-4-oxo-4H-quinazolin-3-yl)-9-nitro-1-phenyl-6,7-dihydro-3H-[1,4]diazepino-[6,7,1-hi]indol-4-one.

$^1$H NMR δ (ppm): 2.7 (d, 6H); 3.3 (2m, 2H); 4.1 (q, 1H); 4.7 (m, 1H); 7.2 (m, 2H); 7.4 (m, 7H); 8.1 (s, 1H); 8.2 (s, 1H).

Example 22
3-(2,6-Dimethyl-4-oxo-4H-quinazolin-3-yl)-9-nitro-1-phenyl-6,7-dihydro-3H-[1,4]diazepino-[6,7,1-hi]indol-4-one.

$^1$H NMR δ (ppm) 2,4 (s, 3H); 2.7 (s, 3H); 3.2 (m, 1H); 3.4 (m, 1H); 4.1 (q, 1H); 4.7 (t, 1H); 7.2 (s, 1H); 7.5 (m, 7H); 7.9 (s, 1H); 8.2 (s, 1H); 8.3 (s, 1H).

Example 23
3-(2,7-Dimethyl-4-oxo-4H-quinazolin-3-yl)-9-nitro-1-phenyl-6,7-dihydro-3H-[1,4]diazepino-[6,7,1-hi]indol-4-one.

$^1$H NMR δ (ppm): 2.4 (s, 3H); 2.7 (s, 3H); 3.15 (m, 1H); 3.35 (m, 1H); 4 (q, 1H); 4,7 (t, 1H); 7.4 (m, 8H); 8.0 (d, 1H); 8.1 (s, 1H); 8.2 (s, 1H).

Example 24
3-(2,8-Dimethyl-4-oxo-4H-quinazolin-3-yl)-9-nitro-1-phenyl-6,7-dihydro-3H-[1,4]diazepino-[6,7,1-hi]indol-4-one.

$^1$H NMR δ (ppm): 2.7 (s, 3H); 2.8 (s, 3H); 3.3 (m, 1H); 3.5 (m, 1H); 4.2 (q, 1H); 4.8 (t, 1H); 7.4 (m, 8H); 8 (d, 1H); 8.2 (s, 1H); 8.3 (s, 1H).

Example 25
3(2,6,8-Trimethyl-4-oxo-4H-quinazolin-3-yl)-9-nitro-1-phenyl-6,7-dihydro-3H-[1,4]diazepino[6,7,1-hi]indol-4-one.

$^1$H NMR δ (ppm): 2.4 (s, 3H); 2.6 (s, 3H); 2.7 (s, 3H); 3.2 (m, 1H); 3.4 (m, 1H); 4 (q, 1H); 4.7 (t, 1H); 7.2 (s, 1H); 7.4 (m, 6H); 7.7 (s, 1H); 8.1 (s, 1H); 8.2 (s, 1H).

Example 26
3-(8-Bromo-2,6-dimethyl-4-oxo-4H-quinazolin-3-yl)-9-nitro-1-phenyl-6,7-dihydro-3H-[1,4]diazepino-[6,7,1-hi]indol-4-one.

$^1$H NMR δ (ppm): 2.4 (s, 3H); 2.7 (s, 3H); 3.2 (m, 1H); 3.4 (m, 1H); 4.1 (q, 1H); 4.7 (t, 1H); 7.1 (s, 1H); 7.4 (m, 5H); 7.8 (s, 1H); 7.9 (s, 1H); 8.2 (s, 1H); 8.3 (s, 1H).

Example 27
(3S)-3-(2-Methyl-4-oxo-4H-pyrido [3,4-dJ -pyrimidin-3-yl)-9-nitro-1-phenyl-6,7-dihydro-3H-[1,4]diazepino[6,7,1-hi]indol-4-one.

(I); A=$NO_2$,Z=N,B=$CH_3$,$X_1$=H, $X_2$=H. (process B)

Stage 1: Preparation of (3R)-3-acetylaminoN-(9-nitro-4-oxo-1-phenyl-3,4,6,7-tetrahydro-[1,4]diazepino[6,7,1-hi]indol-3-yl)isonicotinamide.

In a 500-ml round-bottomed flask equipped with a $CaCl_2$ guard tube, 5.1 g (11.5 mmol) of (3R)-3-amino-N-(9-nitro-4-oxo-1-phenyl-3,4,6,7-tetrahydro-[1,4]diazepino[6,7,1-hi]indol-3-yl)isonicotinamide, the preparation of which is described under the intermediate 5, are introduced into 100 ml of pyridine, 50 ml of acetic anhydride are added and the mixture is stirred for 16 h at 20–25° C. The mixture is cooled in ice, and 250 ml of water are added. After stirring for 4 h at room temperature, the mixture is extracted with ethyl acetate and the organic phase is washed with saturated $NaHCO_3$ and then with water. The solvent is evaporated off and the residue purified by flash chromatography on silica, eluting with D/A10, D/A20, and then D/A30. Weight=2.7 g—Yld=49%.

Stage 2: In a 100-ml round-bottomed flask protected from moisture and under nitrogen, 1.7 g (3.5 mmol) of the acetylated derivative obtained in the preceding step are introduced into 40 ml of 1,2-dichlorobenzene. The medium is brought to 1 90° C. for 24 h; after cooling, the reaction medium is purified directly on a silica column, eluting with D/M1.

Weight=0.7 g—Yld=43%—TLC (D/M5): Rf=0.55.

$^1$H NMR δ (ppm): 2.8 (s, 3H); 3.4 (2m, 2H); 4.2 (q, 1H); 4.8 (m, 1H); 7.1 (m, 1H); 7.4–7.6 (m, 5H); 8.0 (s, 1H); 8.2 (s, 1H); 8.4 (s, 1H); 8.7 (s, 1H); 9.1 (s, 1H).

Example 28
(3S)-9-Amino-3-(2-methyl-4oxo-4H-quinazolin-3-yl)-1-phenyl-6,7-dihydro-3H-[1,4]diazepino[6,7,1-hi]indol-4-one.

(I) (3S); A=$NH_2$,Z=CH, B=$CH_3$, $X_1$=H, $X_2$=H (process A1c)

The compound is prepared according to the procedure of Example 3 from the intermediate 4 of R configuration and N-acetylanthranilic acid.

$^1$H NMR δ (ppm): 2.8 (s, 3H); 3 (m, 1H); 3.2 (m, 1H); 3.85 (q, 1H); 4.5 (q, 1H); 6.4 (s, 1H); 6.8 (s, 1H); 7.1 (s, 1H); 7.4–7.6 (m, 7H); 7.7 (m, 2H); 7.9 (m, 1H); 8.15 (d, 1H).

IR: 3300, 1660, 1580, 1480, 1380, 1300, 1240, 1100, 880, 780, 700 cm$^{-1}$.

Example 28A
Methyl 3-(9-amino-4-oxo-1-phenyl-3,4,6,7-tetrahydro-[1,4]diazepino[6,7,1-hi]indol-3-yl)-2-methyl-4-oxo-3,4-dihydroquinazoline-7-carboxylate (I); A=$NH_2$, Z=CH, B=$CH_3$, $X_1$=H, $X_2$=$CO_2CH_3$ (process A4)

The compound is prepared from the intermediate 4 and an ester derivative of 2-aminoterephthalic acid:

Stage 1: Preparation of Dimethyl 2-(1-methoxyethylideneamino)terephthalate 3.8 g (32 mmmol) of 1,1,1-trimethoxyethane and 1.5 g (7.17 nmuol) of dimethyl 2-aminoterephthalate are introduced into a reactor. The medium is stirred and refluxed for 5 h, and then concentrated to dryness at 50° C. under a vacuum of less than 1 mm Hg. 1.4 g of a thick brown oil are obtained.—TLC (99/1 $CH_2Cl_2$/MeOH): Rf=0.7 –0.8.

¹H NMR δ (ppm): 1.8 (s, 3H); 3.78 (s, 3H); 3.82 (s, 3H); 3.90 (s, 3H); 7.4 (s, 1H); 7.65 (d, 1H); 7.85 (d, 1H).

Stage 2: 3 ml of methanol and 1.5 g (5.13 mmol) of the intermediate 4 are added to the product obtained in stage 1 above. The solution is refluxed for 16 h. A yellow suspension is obtained, which is diluted with methanol and filtered off. 10 ml of methanol are added to the precipitate to purify it, and the mixture is brought to reflux. 1.2 g (Yld=47.4%) are obtained.—M.p.=276° C.—TLC (95/5 $CH_2Cl_2$/MeOH): Rf=0.8.

¹H NMR δ (ppm): 2.85 (s, 3H); 3–3.1 (m, 1H); 3.25–3.35 (m, 1H); 3.6–3.85 (m, 2H); 3.85–3.95 (m, 1H); 3.95 (s, 3H); 4.6–4.7 (m, 1H); 6.45 (s, 1H); 6.85 (s, 1H); 7.15 (s, 1H); 7–7.6 (m, 5H); 8.0 (d, 1H); 8.25 (d, 1H); 8.45 (s, 1H).

IR: 3400, 3300, 3220, 1770, 1650, 1620, 1590, 1560, 1480, 1440, 1380, 1300, 1240, 1160, 1090, 1010, 760, 710 cm⁻¹.

Example 28B

The enantiomers are separated on a preparative HPLC system (of the Merck type, by injecting the racemate onto a Chiralcel OJ 20×250 mm chiral column, particles of 10 μm, 3 0 thermostatically adjusted to 35° C.), or an analytical column (Chiralcel OJ 250×4.5 rnm column, thermostatically adjusted to 35° C., eluent: 50/50 hexane/ethanol, flow rate 1.2 ml/min). Under the latter conditions, the enantiomer A has a retention time of 9.3 min.

Example 28C

Under these same conditions, the enantiomer B has a retention time of 16.5 min.

Example 28D 3-(9-Amino-4oxo-1-phenyl-3,4,6,7-tetrahydro[1,4]diazepino[6,7,1-hi]indol-3-yl)-2-methyl-4-oxo-3,4-dihydroquinazoline-7-carboxylic acid (I); A=$NH_2$, Z=CH, B=$CH_3$, $X_1$=H, $X_2$=$CO_2H$ 0.6 g (1.22 mmmol) of the product of Example 28A and 30 ml of THF are introduced into a reactor. After solubilization, a solution of 0.135 g of KOH in 8 ml of water is added and the mixture is kept stirring for 3 h at 20–25° C. The mixture is neutralized with 0.1 N HCl to pH 6.8 and the THF is evaporated off at 50° C. under a vacuum of 20 rnm Hg. The residue is chromatographed, eluting with $CH_2Cl_2$ progressively enriched with methanol. The product obtained is crystallized from 10 ml of $CH_2Cl_2$ and the precipitate is filtered off. 0.25 g is obtained (Yld=42.7%). M.p.>275° C.—TLC (85/15 $CH_2Cl_2$/MeOH): Rf=0.35.

¹H NMR δ (ppm): 2.7 (s, 3H); 3.0–3.1 (m, 1H); 3.3–3.4 (m, 1H); 3.4–3.7 (m, 3H exch.); 3.8–3.95 (m, 1H); 4.45–4.55 (m, 1H); 6.45 (s, 1H); 6.9 (s, 1H); 6.95 (s, 1H); 7.4–7.6 (m, 5H); 7.95–8.2 (m, 3H).

IR: 3350, 1680, 1480, 1380, 1300, 1240, 1170, 1110, 1010, 790, 690 cm⁻¹.

Example 29

9-Amino-3-(2-methyl-4-oxo-4H-quinazolin-3-yl)-1-phenyl-6,7-dihydro-3H-[1,4]diazepino[6,7,1-hi]indol-4-one.

(I); A=$NH_2$, Z=CH, B=$CH_3$, $X_1$=H, $X_2$=H (process C1)

The compound is prepared by reduction of the product of Example 20 with sodium sulfide, which is the preferred agent according to the process C1: 0.5 g (1.07 mmol) of the product of Example 20, 0.672 g (2.8 mmol) of $Na_2S.9H_2O$ and 3.21 ml of ethanol are introduced into a reactor. The mixture is heated to 60° C. with stirring for 2 h. The solvent is evaporated off and the residue taken up with water and extracted with $CH_2Cl_2$. After purification by flash chromatography on silica, eluting with the solvent D/A2, 190 mg of a yellow solid are obtained.

Weight=0.19 g—Yld: 41%—M.p.=291° C.

¹H NMR δ (ppm): identical to the product of Example 28 above.

An alternative process consists in using titanium trichloride as reducing agent. Thus, in a reactor under nitrogen, protected from moisture and equipped with a magnetic stirrer, 5.0 g (10.7 minol) of the product of Example 20 are introduced into 42.8 ml of acetic acid. 64 mmol of $TiCl_3$ (in 30% solution in 2N HCl) are added dropwise and the mixture is kept stirring for 30 min. It is then alcalinized with sodium hydroxide to a pH of 9, the medium being cooled by adding ice.

The mixture is then extracted with ethyl acetate. After evaporation of the solvent, the product is purified by flash chromatography on silica. Yld: 10%.

Example 30

9-Amino-3-(2,5-dimethyl-4-oxo-4H-quinazolin-3-yl)-1-phenyl-6,7-dihydro-3H-[1,4]diazepino[6,7,1-hi]indol-4-one.

(I); A=$NH_2$,Z=CH, B=$CH_3$, $X_1$=H, $X_2$=$CH_3$ at position 5 (process C1)

The product is obtained by reducing the compound of Example 21 with $Na_2S$.

¹H NMR δ (ppm): 2.65 (s, 3H); 2.7 (s, 3H); 3 (m, 1H); 3.3 (m, 1H); 4.4 (q, 1H); 4.5 (t, 1H); 5.7 (s, 1H); 6.4 (s, 1H); 6.9 (d, 2H); 7.5 (m, 9H).

Example 31

9-Amino-3-(2,6dimethyl-4-oxo-4H-quinazolin-³-yl)-1-phenyl-6,7-dihydro-3H-[1,4]diazepino[6,7,1-hi]indol-4-one.

(I); A=$NH_2$, Z=CH, B=$CH_3$, $X_1$=H, $X_2$=$CH_3$ at position (process C1)

The product is obtained by reducing the compound of Example 22 with $Na_2S$.

¹H NMR δ (ppm): 2.4 (s, 3H); 2.7 (s, 3H); 3 (m, 1H); 3.3 (m, 1H); 3.9 (q, 1H); 4.5 (t, 1H); 5.4 (s, 2H); 6.4 (s, 1H); 6.9 (d, 2H); 7.5 (m, 7H), 7.9 (s, 1H).

Example 32

9-Amino-3-(2,8-dimethyl-4-oxo-4H-quinazolin-3-yl)-11-phenyl-6,7-dihydro-3H-[1,4]diazepino[6,7,1-hi]indole-4-one.

(I); A=$NH_2$, Z=CH, B=$CH_3$, $X_1$=H, $X_2$=$CH_3$ at position 8 (process C2)

In a 100-ml round-bottomed flask equipped with a condenser, 550 mg (1.15 mnmol) of the product of Example 24 are introduced into 20 ml of absolute ethanol. The medium is heated to permit dissolution. 1.3 g (5.75 mmol) of $SnCl_2.2H_2O$ are added. The temperature is maintained for 1 h at 50° C., 30 ml of ice are then introduced and the mixture is alkalinized to a pH of 12 with 1N NaOH. The medium is extracted with $CH_2Cl_2$; the organic phase is washed with saturated aqueous NaCl solution and then dried over $Na_2SO_4$. The product is purified by flash chromatography on a silica column, eluting with the solvent D/M1 and then D/M2. A yellow solid is obtained—Weight=60 mg—Yld=12%.

¹H NMR δ (ppm): 2.6 (s, 3H); 2.7 (s, 3H); 3 (m, 1H); 3.3 (m, 1H); 3.9 (q, 1H); 4.5 (t, 1H); 5.4 (s, 2H); 6.4 (s, 1H); 6.95 (d, 2H); 7.5 (m, 6H); 7.7 (d, 1H); 7.9 (d, 1H).

Example 33

9-Amino-3-(2,6,8-trimethyl-4-oxo-4H-quinazolin-3-yl)-1-phenyl-6,7-dihydro-3H-[1,4]diazepino[6,7,1-hi]indol-4-one.

(I); A=NH$_2$, Z=CH, B=CH$_3$, X$_1$=CH$_3$ at position 6, X$_2$=CH$_3$ at position 8 (process C2)

The product is obtained in the form of a yellow solid from the compound of Example 25, the reducing agent being SnCl$_2$.

$^1$H NMR δ (ppm): 2.4 (s, 3H); 2.55 (s, 3H); 2.7 (s, 3H); 3 (m, 1H); 3.3 (m, 1H); 3.9 (q, 1H); 4.5 (t, 11H); 5.4 (s, 2H); 6.4 (s, 11H); 6.9 (s, 11H); 6.95 (s, 11H); 7.5 (m, 6H); 7.7 (s, 11H).

Example 34

9-Amino-3-(2-methyl-4-oxo-4H-pyrido[3,4-d]pyrimidin-3-yl)-1-phenyl-6,7-dihydro-3H-[1,4]diazepino[6,7,1-hi]indol-4-one.

(I); A=NH$_2$, Z=N, B=CH$_3$, X$_1$=X$_2$=H (process C2)

The product is obtained in the form of a yellow solid from the compound of Example 19, the reducing agent being SnCl$_2$.

$^1$H NMR δ (ppm): 2.7 (s, 3H); 3.05 (m, 1H); 3.3 (m, 1H); 3.9 (q, 111); 4.5 (t, 1H); 5.4 (s, 2H); 6.4 (s, 1H); 6.85 (s, 1H); 6.9 (s, 1H); 7.5 (m, 5H); 7.9 (d, 1H); 8.7 (d, 1H); 9.1 (s, 1H).

Example 34A

5-Chloro-2-methyl-3-(9-nitro-4-oxo-1-phenyl-3,4,6,7-tetrahydro[1,4]diazepino[6,7,1-hi]indol-3-yl)-4-oxo-3,4-dihydroquinazoline.

(I); A=NO$_2$, Z=CH, B=CH$_3$, X$_1$=H, X$_2$=Cl at 5 (process A2)

A mixture of 7 g (35.7 mmol) of 5-chloro-2-methyl-4-oxo-4H-benzo[d][1,3]oxazine (prepared from 6-chloro-2-aminobenzoic acid and acetic anhydride, according to J. Am. Chem. Soc. (1907) 29: p. 86) and 8.87 g (27.5 mmol) of the intermediate 3.a in 50 ml of CH$_2$Cl$_2$ is maintained at 100° C. under a pressure of 4 bar for 8 h in an autoclave. The medium is cooled, the solvent is evaporated off and the residue is purified by flash chromatography on a column of silica, eluting with the solvents D/M0.5 and D/M1.5. The fractions of interest are combined and evaporated. 6.7 g of an amorphous solid are obtained. Yld=43%.—TLC: (D/M0.5): Rf=0.35.

$^1$H NMR δ (ppm): 2.35 (s, 3H); 2.65 (s, 3H); 3.1 (m, 1H); 3.35 (q, 1H); 3.95 (q, 1H); 4.45 (t, 1H); 6.95 (s, 1H); 7.05 (s, 1H); 7.4–7.55 (m, 6H); 8.0 (d, 1H); 8.1 (d, 2H).

Example 34B

9-Amino-3-(5-chloro-2-methyl-4-oxo-4H-quinazolin-3-yl)-1-phenyl-6,7-dihydro-3H-[1,4]diazepino[6,7,1-hi]indol-4-one.

(I); A=NH$_2$, Z=CH, B=CH$_3$, X$_1$=H, X$_2$=Cl at 5 (process C1).

The compound is prepared by reduction of 3.54 g (7.14 mmol) of the product of Example 34A with Na$_2$S, which is the preferred agent according to the process C1, as in Example 29, with heating for 12 h. After purification by chromatography on silica, eluting with the solvent DM2, 530 mg of a yellow solid are obtained. Yld=31%.—M.p.= 272° C.—TLC (D/M2): Rf=0.35.

$^1$H NMR δ (ppm): 2.8 (s, 3H); 3.0 (m, 1H); 3.4 (m, 1H); 3.9 (q, 1H); 4.7 0; 6.5 (s, 1H); 6.9 (s, 1H); 7.2–7.8 (m, 9H).

IR: 3300, 3200, 1660, 1580, 1450, 1380, 1320, 1270, 1160, 780, 700 cm$^{-1}$.

Examples 35 to 35I

Preparation of the Common Intermediate:
Pentafluorophenyl 2-methyl-3-(9-methyl-4-oxo-1-phenyl-3,4,6,7-tetrahydro-[1,4]diazepino[6,7,1-hi]indol-3-yl)-4-oxo-3,4-dihydroquinazoline-7-carboxylate.

(I); A=CH$_3$, Z=CH, B=CH$_3$, X$_1$=H, X$_2$=CO$_2$–C$_6$F$_5$ at 7. (Process D11a)

4.6 g (9.6 mmmol) of the acid obtained in Example 7 in 200 ml of CH$_2$Cl$_2$ dried over sieves are introduced into a reactor protected from moisture; 3.54 g (19 mmol) of pentafluorophenol, 8.3 g (4.3 mmol) of N-ethyl-N-3-dimethylaminopropylcarbodiimide hydrochloride and 0.48 g (0.25 mmol) of 4-dimethylaminopyridine para-toluenesulfonate are added.

The solution is stirred for 5 h at 20–25° C. It is washed with 200 ml of water and then with 200 ml of 5% NaHCO$_3$ solution. The organic phase is dried and evaporated. The product is recrystallized from ether (60 ml). 5.54 g of white powder are obtained. Yld=89%—TLC (D/M2): Rf=0.92.

Example 35

General Process 185 mg (0.1 rnrmol) of Fmoc-valine (9-fluorenylmethoxyarbonyl-(L)-valine) which are bound to a Wang resin, are placed in 4.8 ml of DMF with stirring; after stirring for 1 h which is intended to make the resin swell, 1.2 ml of piperidine are added with stirring for a further 1.5 h, and the resin is rinsed three times with 5 ml of DMF and then with three times 5 ml of methanol and finally three times with 5 ml of CH$_2$Cl$_2$.100 mg (0. 1 5 mmol) of the above pentafluorophenyl ester in 8 ml of CH$_2$Cl$_2$ are added and the mixture is stirred for 20 h at room temperature. The phases are separated after settling has taken place and the resin is rinsed three times with 5 ml of DMF and then three times with 5 ml of methanol and finally three times with 5 ml of CH$_2$Cl$_2$. The coupling operation is repeated a second time. The rinsed resin is stirred in a 50/50 (v/v) trifluoroacetic acid/CH$_2$Cl$_2$ mixture for 1 h at 25° C. The resin is filtered off and rinsed with CH$_2$Cl$_2$. It is concentrated and stripped off the CH$_2$Cl$_2$ several times. The purity is determined by high-pressure chromatography on a Nucleosil C18 column, the mobile phase being a 65/35 (v/v) KH$_2$PO$_4$ buffer/acetonitrile mixture. The flow rate is 1 ml/min; the UV absorption at 240 nm is recorded.

TLC (66/17/17 n-butanol/acetic acid/water): Rf=0.89.

50 mg of N-(2-methyl-3-(9-methyl-4-oxo-1-phenyl-3,4,6, 7-tetrahydro[1,4]diazepino[6,7,1-hi]indol-3-yl)-4-oxo-3,4-dihydroquinazoline-7-carbonyl)valine are obtained.

Nine other products are prepared in the same way:

Example 35A

N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)tyrosine.

Example 35B

N2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)alanine.

Example 35C

N-(2-Methyl-3-(9-methyl-4-oxo-1-phenyl-3,4,6,7-tetrahydrol[1,4]diazepino[6,7,1-hi]indol-3-yl)-4-oxo-3,4-dihydroquinazoline-7-carboxyl)phenylalanine.

Example 35D

N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)glycine.

Example 35E

N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)leucine.

Example 35F

N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)aspartic acid.

Example 35G
N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)proline.

Example 35H
N-(2-Methyl-3-(9-methyl-4-oxo-1-phenyl-3,4,6,7-tetrahydro[1,4]diazepino[6,7,1-hi]indol-3-yl)-4-oxo-3,4-dihydroquinazoline-7-carboxyl)glutamic acid.

Example 35I
N-(2-Methyl-3-(9-methyl-4-oxo-1-phenyl-3,4,6,7-tetrahydrol 1,4]diazepino[6,7,1-hi]indol-3-yl)-4-oxo-3,4-dihydroquinazoline-7-carboxyl)lysine.

| Example: | Resin | Mass (mg) | Purity (%) | Rf (TLC) | Retention time (HPLC) |
|---|---|---|---|---|---|
| 35 | N-Fmoc-valine | 50 | 94.6 | 0.89 | 10.95 min |
| 35A | N-Fmoc-O-t-Bu-tyrosine | 40 | 77.5 | 0.94 | 16.55 |
| 35B | N-Fmoc-alanine | 40 | 78.4 | 0.94 | 18.63 |
| 35C | N-Fmoc-phenylalanine | 20 | 87.8 | 0.93 | 28.77/30.63 |
| 35D | N-Fmoc-glycine | 60 | 97.6 | 0.83 | 8.09 |
| 35E | N-Fmoc-leucine | 40 | 94.1 | 0.97 | 40.36/44.13 |
| 35F | N-Fmoc-γ-O-t-Bu-aspartic acid | 40 | 94.4 | 0.78 | 6.09 |
| 35G | N-Fmoc-proline | 80 | 97.5 | 0.79 | 10.89 |
| 35H | N-Fmoc-δ-O-t-Bu-glutamic acid | 60 | 96.0 | 0.86 | 7.53 |
| 35I | N-Fmoc-ε-N-Boc-lysine | 70 | 96.6 | 0.38 | 8.84 |

Example 36
Ethyl 2-{[2-methyl-3-(9-methyl-4-oxo-1-phenyl-3,4,6,7-tetrahydro[1,4]diazepino[6,7,1-hi]indol-3-yl)-4-oxo-3,4-dihydroquinazolin0e-7-carbonyl]amino}-3-phenyl-(L)-propionate.

(I); A=$CH_3$, Z=CH, B=$CH_3$, $X_1$=H, $X_2$ (at 7)=CONHCH($CH_2C_6H_5$)$CO_2CH_2CH_3$ (Process D11a)

The compound is prepared as described in Example 35, the amidation being carried out by a solution of ethyl (L)-phenylalaninate in $CH_2Cl_2$. The product, after chromatogrOaphic purifications, is obtained in the form of a white powder. Yld=81%. M.p.=135° C.—TLC (50/50 AEC): Rf=0.30.

$^1$H NMR δ (ppm): 1.7 (t, 3H); 2.3 (s, 3H); 2.8 (s, 3H); 3.0 (m, 1H); 3.3 (m, 1H); 3.9 (q, 2H); 4.2 (m, 1H); 4.6 (dt, 1H); 5.0 (m, ); 6.7 (d, 1H); 7.0 (s, 1H); 7.1 (m, 1H); 7.2 (m, XH); 7.3 (m, H); 7.4 (m, H); 7.5 (d,); 7.7 (d,); 7.9 (t,); 8.2 (d,).

IR: 3350, 3000, 2900, 1720, 1680, 1620, 1580, 1560, 1480, 1440, 1420, 1400, 1340, 1180, 1120, 1020, 960, 740, 700 cm$^{-1}$.

Biological Activity
Phosphodiesterase-Inhibiting Activity

The capacity of the compounds of formula (I) of the invention to inhibit cyclic nucleotide phosphodiesterases is evaluated by measuring their $IC_{50}$ (concentration necessary for inhibiting 50% of the enzyme activity). In the case of the PDE4 enzymes, this value is compared with that of rolipram, a specific PDE4 inhibitor. The different types of phosphodiesterases are obtained partially purified on a DEAE-cellulose column from guinea pig trachea and dog aorta according to a method adapted from W. J. Thompson et al., 1979, Advances in Cyclic Nucleotide Research, Vol. 10: 69–92, ed. G. Brooker et al. Raven Press, New York, and from P. J. Silver et al., 1988, Eur. J. Pharrnacol. 150: 85–94, and from the cell line of human origin U937 according to a method adapted from T. J. Torphy et al., 1992, J. Pharm. Exp. Ther. 263: 1195 –1205. Measurement of the enzyme activity of the different types of PDE, and especially of the PDE4 enzymes, is then carried out according to a method adapted from W. J. Thompson, ibidem. For the determination of the $IC_{50}$, the enzyme activity is measured in the presence of the inhibitor in a concentration range from $10^{-10}$ to $10^{-4}$ M.

The following table illustrates PDE4-inhibiting activity of Examples according to the invention on an enzyme preparation obtained from the U937 cell line.

| Example | Enzyme |
|---|---|
| 1 | 0.448 |
| 2 | 0.146 |
| 2A | 0.183 |
| 2B | 0.067 |
| 2C | 0.108 |
| 3 | 0.141 |
| 4 | 0.553 |
| 5 | 0.832 |
| 6 | 3.016 |
| 6A | 0.133 |
| 6B | 1.418 |
| 6C | 0.838 |
| 6D | 0.372 |
| 6E | >100.000 |
| 6F | >100.000 |
| 7 | 0.052 |
| 7A | 0.157 |
| 7B | 0.057 |
| 7C | 0.066 |
| 7D(R) | 0.982 |
| 7E(S) | 0.035 |
| 8 | 0.050 |
| 8A | n.t. |
| 8B | 0.028 |
| 9 | 0.063 |
| 9A | 0.122 |
| 9B | 0.095 |
| 9C | 0.069 |
| 9D | 0.119 |
| 9E | n.t. |
| 9F | 0.192 |
| 9G | 0.137 |
| 9H | n.t. |
| 9I | 0.119 |
| 10 | 0.183 |
| 10A | 0.108 |
| 10B | 0.155 |
| 10C | 0.081 |
| 10D | 0.042 |
| 10E | 0.075 |
| 11 | 0.079 |
| 12 | 0.088 |
| 13 | 0.083 |
| 14 | 0.310 |
| 15 | 0.082 |
| 16 | 0.260 |
| 17 | 0.746 |
| 17A | 0.137 |
| 17B | 0.221 |
| 17C | 0.339 |
| 17D | 0.286 |
| 17E | 0.222 |
| 17F | 0.147 |
| 17G | 0.516 |
| 17H | 0.184 |
| 18 | 0.823 |
| 19 | 0.193 |
| 19A | 1.477 |
| 20 | n.t. |
| 21 | n.t. |
| 22 | 1.734 |
| 23 | 0.497 |

-continued

| Example | Enzyme |
|---|---|
| 24 | 30.564 |
| 25 | >100.000 |
| 26 | 90.620 |
| 27 | n.t. |
| 28 | 0.005 |
| 28A | 0.005 |
| 28B | 0.003 |
| 28C | 0.070 |
| 28D | 0.009 |
| 29 | 0.013 |
| 30 | 0.008 |
| 31 | 0.087 |
| 32 | 0.055 |
| 33 | 0.155 |
| 34 | 0.042 |
| 34A | n.t. |
| 34B | 0.003 |
| 35 | 0.106 |
| 35A | 0.088 |
| 35B | 0.190 |
| 35C | 0.111 |
| 35D | 0.065 |
| 35E | 0.082 |
| 35F | 0.547 |
| 35G | 0.291 |
| 35H | 0.219 |
| 35I | 0.120 |
| 36 | 0.312 |
| rolipram | 0.792 | n.t.: not tested

Inspection of the results in the above table shows that the products of the invention generally inhibit the PDE4 enzyme of human origin much more effectively than rolipram, and in some cases are approximately 100 times as active as rolipram.

Moreover, tests carried out on PDEs of different types, purified from guinea pig trachea or from dog aorta, show that the $IC_{50}$ values obtained with the products of the invention with respect to PDEs of type 3 and of type 1 and 5 are much higher than those measured for the type 4 PEDs. These results are evidence of a potent and selective inhibitory activity for the products of the invention with respect to the PDE4 enzymes.

Examples 28A, 28B, 28C, 28D, 34, and 34B at concentrations lower than $5 \times 10^{-6}$ M have proved capable of inhibiting bacterial LPS-induced production of TNF-a in whole human blood.

Anti-Inflammatory and Anti-Allergic Activity in vivo

The effects of the products of the invention were studied in rats in a model of eosinophil infiltration induced by an antigenic stimulation, according to a methodology adapted from Lagente V. et al., (1994) Br. J. Pharmacol. 112, 83P.

The administration a number of products of the Examples at 10 mg/kg p.o. significantly decreased the number of eosinophils in the bronchoalveolar lavage fluid.

These results demonstrate the anti-inflammatory and/or anti-allergic activity of the products of the invention. Hence the products of the invention will be especially useful for the treatment or prevention of:

allergic pathologies, and in particular asthma and atopic dermatitis; inflammatory pathologies, in particular those affecting the bronchus, but also rheumatoid arthritis and inflammatory intestinal complaints (hemorrhagic rectocolitis and Crohn's disease); including, where it is present, an autoimmune component.

Pharmaceutical Formulation

The products of the invention are administered in the form of compositions suited to the nature and extent of the complaint to be treated. The daily dosage in man is usually between 2 mg and 1 g of product, which can be taken in one or several doses. The compositions are prepared in forms which are compatible with the administration route envisaged, such as, for example, tablets, dragees, capsules, mouthwashes, aerosols, powders for inhalation, suppositories, gels or suspensions. These compositions are prepared by methods familiar to a person skilled in the art, and comprise from 0.5 to 60% by weight of active principle (compound of formula I) and 40 to 99.5% by weight of suitable pharmaceutical vehicle which is compatible with the active principle and the physical form of the composition envisaged. The composition and preparation of tablets containing a compound of the invention are presented by way of example:

Active substance of formula (I) I to 75 mg

Lactose 124 to 74 mg

Microcrystalline cellulose 36 to 60 mg

Polyvinylpyrrolidone 6 mg

Sodium carboxymethyl starch 8 mg

Magnesium stearate 1 mg

Mix the active substance, lactose, microcrystalline cellulose and carboxymethyl starch. Wet and granulate using an aqueous or alcoholic solution of polyvinylpyrrolidone of appropriate concentration. Dry and size the granule. Mix the magnesium stearate homogeneously. Tablet on the basis of 200 mg per tablet.

What is claimed is:

1. A compound of formula I

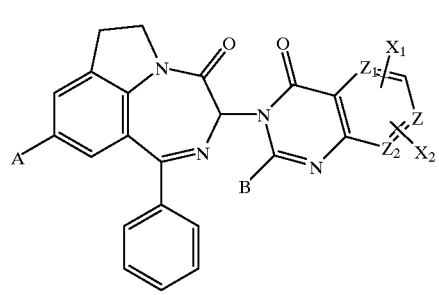

wherein:

A is hydrogen, $C_1$–$C_4$alkyl, $OR^1$, hydroxy, nitro, cyano, —$NH_2$—, —$NHR^1$, or —$NR^1R^2$;

$R^1$ and $R^2$ independently are $C_1$–$C_4$alkyl, cyclopropyl, cyclopropylmethyl, or $NR^1R^2$ taken together with the nitrogen to which they are bound complete a ring having 4 or 5 carbon atoms;

B is hydrogen, $C_1$–$C_4$alkyl, —$CH_2OM$, —$CH_2OC(=O)$ $(CH_2)_a(CO)_bY^1Y^2$, or —$(CH_2)_cC(=O)OM$;

Y1 is —$(VCH_2CH_2)_c$—, with V=—NH— or —O—; or $Y^1$ is —$NHCHR^A$—$C(=O)$—;

$Y^2$ is hydrogen, hydroxy, —$OCH_3$, or 4-morpholinyl;

M is hydrogen or $C_1$–$C_4$alkyl;

a=1 or 2; b=0 or 1; c=0, 1, or 2;

Z is CH, then $Z_1$ and $Z_2$ both are CH or N; or

Z is N, then $Z_1$ and $Z_2$ are CH;

$X_1$ and $X_2$ independently are hydrogen, $C_1$–$C_4$alkyl, —$(CH_2)_n$—$OR^3$, halogen, cyano,

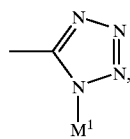

—O—$C_1$-$C_6$alkyl, —C(=O)$R_3$, —C(=O)O$R_3$, —C(=O)N$R^4R^5$, or

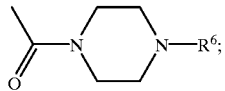

$R^3$ is hydrogen, $C_1$-$C_6$alkyl, benzyl, phenethyl, or —$Q^1$-$Q^2$;
$R^4$ is hydrogen, or $C_1$-$C_4$alkyl;
$R^5$ is hydrogen, $C_1$-$C_4$alkyl, —CHR$^A$—C(=O)OM1, or —$Q^3$-$Q^4$;
$R^6$ is hydrogen, $C_1$-$C_4$alkyl, or —$Q^3$-$Q^5$;
$R^A$ is a residue of a natural α-amino-acid, the carbon atom to which it is linked having either a S configuration, or a R configuration;
$Q^1$ is —(CH$_2$)$_n$—(CHOH)$_m$—(CH$_2$)$_p$—;
$Q^2$ is hydroxy, —O—$C_1$-$C_6$alkyl, —OC(=O)—$C_1$-$C_6$alkyl, or 4-morpholinyl;
$Q^3$ is —(CH$_2$)$_n$—;
$Q^4$ is —NHM$^1$, —NM$^1$M$^2$, or 4-morpholinyl;
$Q^5$ is —M$^1$ or —OM$^1$;
$M^1$ and $M^2$ are independently hydrogen or $C_1$-$C_4$alkyl;
n is 1, 2, or 3; m is 0, 1, 2, 3, or 4; p is 0, 1, 2, or 3, provided that if m is not 0, then p is not 0;

its racemic form and each of its isomers, and the pharmaceutically acceptable salts thereof.

2. A compound of claim 1 wherein carbon 3 of the [1,4]diazepino[6,7,1-hi]-indol-4-one ring system has the S configuration.

3. A compound of claim 1 or 2 wherein:

A is hydrogen, methyl, hydroxy, —OCH$_3$, —NH$_2$, —NHCH$_3$; —N(CH$_3$)$_2$ or 1-pyrrolidinyl;

B is $C_1$-$C_4$alkyl, —CH$_2$O H, —CH$_2$OCH$_3$, —CO$_2$—CH$_2$—CH$_3$; and $X_1$ and $X_2$ are independently hydrogen, methyl, methoxy, —CH$_2$OH, F, Cl, Br, —C(=O)O$R^3$, or C(=O)N$R^4R^5$.

4. A compound of claim 1, 2, or 3 wherein

A is —CH$_3$ or —NH$_2$; and

B is —CH$_3$ or —CH$_2$OCH$_3$.

5. A compound of claim 1, 2, 3, or 4 wherein

Z, Z$_1$, Z$_2$ are CH; and $X_1$ or $X_2$ is methyl, F, Cl, or Br at position 5 of the quinazoline ring system.

6. A compound of claim 1, 2, 3, 4, or 5 wherein

Z, Z$_1$, Z$_2$ are CH;

A is —NH$_2$; and $X_1$ or $X_2$ is —C(O)O$R^3$ or —C(=O)N$R^4R^5$ at position 7 of the quinazoline ring system.

7. A compound selected from the group consisting of:

(3S)3-(2-Methyl-4-oxo-4H-quinazolin-3yl)-1-phenyl-6,7-dihydro-3H-[1,4]diazepino[6,7,1-hi]indol-4-one;

9-Methoxy-3-(2-methyl-4-oxo-4H-quinazolin-3yl)-1-phenyl-6,7-dihydro-3H-[1,4]diazepino[6,7,1-hi]indol-4-one;

2-Methyl-3-(9-methoxy-4-oxo-1-phenyl-3,4,6,7-tetrahydro-[1,4]diazepino[6,7,1-hi]indol-3-yl)-4-oxo-3,4-dihydro-quinazoline-7-carboxylic acid methyl ester;

2-Methyl-3-(9-methoxy-4-oxo-1-phenyl-3,4,6,7-tetrahydro-[1,4]diazepino[6,7,1-hi]indol-3-yl)-4-oxo-3,4-dihydro-quinazoline-7-carboxylic acid.

8. A compound selected from the group consisting of:

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid methyl ester;

D-Glucamine 2-methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylate salt;

(3R) 2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

(3S) 2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-morpholin-4-yl-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-acetoxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-methoxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-hydroxy-ethyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 1-(2S)-glycerol ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid 2-hydroxy-3-morpholin-4-yl-propyl ester.

9. A compound selected from the group consisting of:

9-Methyl-3-(2-methyl-4-oxo-4H-quinazolin-3yl)-1-phenyl-6,7-dihydro-3H-[1,4]diazepino[6,7,1-hi]indol-4-one;

(3S) 9-Methyl-3-(2,5-dimethyl-4-oxo-4H-quinazolin-3yl)-1-phenyl-6,7-dihydro-3H-[1,4]diazepino[6,7,1-hi]indol-4-one;

(3S) 9-Methyl-3-(2,6-dimethyl-4-oxo-4H-quinazolin-3yl)-1-phenyl-6,7-dihydro-3H-[1,4]diazepino[6,7,1-hi]indol-4-one;

(3S) 9-Methyl-3-(2,8-dimethyl-4-oxo-4H-quinazolin-3yl)-1-phenyl-6,7-dihydro-3H-[1,4]diazepino[6,7,1-hi]indol-4-one;

3-(5-Methoxy-2-methyl-4-oxo-4H-quinazolin-3yl)-9-methyl-1-phenyl-6,7-dihydro-3H-[1,4]diazepino[6,7,1-hi]indol-4-one;

3-(7-Methoxy-2-methyl-4-oxo-4H-quinazolin-3yl)-9-methyl-1-phenyl-6,7-dihydro-3H-[1,4]diazepino[6,7,1-hi]indol-4-one;

3-(6-Methoxy-2-methyl-4-oxo-4H-quinazolin-3yl)-9-methyl-1-phenyl-6,7-dihydro-3H-[1,4]diazepino[6,7,1-hi]indol-4-one;

3-(6-Bromo-2-methyl-4-oxo-4H-quinazolin-3yl)-9-methyl-1-phenyl-6,7-dihydro-3H-[1,4]diazepino[6,7,1-hi]indol-4-one;

3-(5-Hydroxymethyl-2-methyl-4-oxo-4H-quinazolin-3yl)-9-methyl-1-phenyl-6,7-dihydro-3H-[1,4]diazepino[6,7,1-hi]indol-4-one;

2-Methyl-3-(9-methyl-4-oxo-1-phenyl-3,4,6,7-tetrahydro-[1,4]diazepino[6,7,1-hi]indol-3-yl)-4-oxo-3,4-dihydroxy-quinazoline-5-carboxylic acid tertiobutyl ester;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-5-carboxylic acid;

3-(7-Hydroxymethyl-2-methyl-4-oxo-4H-quinazolin-3yl)-9-methyl-1-phenyl-6,7-dihydro-3H-[1,4]diazepino[6,7,1-hi]indol-4-one;

(3S) 3-(5-Fluoro-2-methyl-4-oxo-4H-quinazolin-3-yl)-9-methyl-1-phenyl-6,7-dihydro-3H-[1,4]diazepino[6,7,1-hi]indol-4-one;

3-(5-Chloro-2-methyl-4-oxo-4H-quinazolin-3-yl)-9-methyl-1-phenyl-6,7-dihydro-3H-[1,4]diazepino[6,7,1-hi]indol-4-one;

(9-Methyl-3-oxo-4H-quinazolin-3-yl)-1-phenyl-6,7-dihydro-3H-[1,4]diazepino-[6,7,1-hi]indol-4-one.

10. A compound selected from the group consisting of:

3-(9-Methyl-4-oxo-1-phenyl-3,4,6,7-tetrahydro-[1,4]diazepino[6,7,1-hi]indol-3-yl)-4-oxo-3,4-dihydro-quinazoline-2-carboxylic acid ethyl ester;

5-Chloro-3-(9-methyl-4-oxo-1-phenyl-3,4,6,7-tetrahydro-[1,4]diazepino[6,7,1-hi]indol-3-yl)-4-oxo-3,4-dihydro-quinazoline-2-carboxylic acid ethyl ester;

[3-(9-Methyl-4-oxo-1-phenyl-3,4,6,7-tetrahydro-[1,4]diazepino[6,7,1-hi]indol-3-yl)-4-oxo-3,4-dihydro-quinazolin-2-yl]-acetic acid ethyl ester;

Acetic acid 3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethyl ester;

9-Methyl-3-(2-methyloxy-4-oxo-4H-quinazolin-3yl)-1-phenyl-6,7-dihydro-3H-[1,4]diazepino[6,7,1-hi]indol-4-one;

9-Methyl-3-(2-hydroxymethyl-4-oxo-4H-quinazolin-3yl)-1-phenyl-6,7-dihydro-3H-[1,4]diazepino[6,7,1-hi]indol-4-one;

Succinic acid mono-[3-(9-methyl-4-oxo-1-phenyl-3,4,6,7-tetrahydro-[1,4]diazepino [6,7,1-hi]indol-3-yl)-4-oxo-3,4-dihydro-quinazolin-2-ylmethyl ester;

[2-(2-Methoxy-ethoxy)-ethoxy]-acetic acid mono-[3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethyl] ester;

N-(2-Morpholin-4-yl-ethyl)-succinamic acid 3-(9-methyl-4-oxo-1-phenyl-3,4,6,7-tetrahydro-[1,4]diazepino[6,7,1-hi]indol-3-yl)-4-oxo-3,4-dihydro-quinazolin-2-yl-methyl ester;

Succinic acid 3-(9-methyl-4-oxo-1-phenyl-3,4,6,7-tetrahydro-[1,4]diazepino-[6,7,1-hi]indol-3-yl)-4-oxo-3,4-dihydro-quinazolin-2-ylmethyl ester 2-morpholin-4-yl-ethyl ester;

6-t-butoxycarbonylamino-2-{3-[3-(9-methyl-4-oxo-1-phenyl-3,4,6,7-tetrahydro-[1,4]diazepino[6,7,1-hi]indol-3-yl)-4-oxo-3,4-dihydro-quinazolin-2-ylmethoxycarbonyl]-propionylamino}-hexanoic acid methyl ester;

3-[3-(9-Methyl-4-oxo-1-phenyl-3,4,6,7-tetrahydro-[1,4]diazepino[6,7,1-hi]indol-3-yl)-4-oxo-3,4-dihydro-quinazolin-2-yl]-propionic acid ethyl ester.

11. A compound selected from the group consisting of:

(3S) 3-(2-Methyl-4-oxo-4H-pyrido[3,4-d]pyrimidin-3-yl)-9-methyl-1-phenyl-6,7-dihydro-3H-[1,4]diazepino[6,7,1-hi]indol-1-one;

3-(2-Methyl-4-oxo-4H-pteridin-3-yl)-9-methyl-1-phenyl-6,7-dihydro-3H-[1,4]diazepino[6,7,1-hi]indol-4-one;

9-Amino-3-(2-methyl-4-oxo-4H-pyrido[3,4-d]pyrimidin-3-yl)-1-phenyl-6,7-dihydro-3H-[1,4]diazepino[6,7,1-hi]indol-3-yl)-4-one.

12. A compound selected from the group consisting of:

3-(2-Methyl-4-oxo-4H-quinazolin-3-yl)-9-nitro-1-phenyl-6,7-dihydro-3H-[1,4]diazepino[6,7,1-hi]indol-4-one;

3-(2,5-Dimethyl-4-oxo-4H-quinazolin-3-yl)-9-nitro-1-phenyl-6,7-dihydro-3H-[1,4]diazepino[6,7,1-hi]indol-4-one;

3-(2,6-Dimethyl-4-oxo-4H-quinazolin-3-yl)-9-nitro-1-phenyl-6,7-dihydro-3H-[1,4]diazepino[6,7,1-hi]indol-4-one;

3-(2,7-Dimethyl-4-oxo-4H-quinazolin-3-yl)-9-nitro-1-phenyl-6,7-dihydro-3H-[1,4]diazepino[6,7,1-hi]indol-4-one;

3-(2,8-Dimethyl-4-oxo-4H-quinazolin-3-yl)-9-nitro-1-phenyl-6,7-dihydro-3H-[1,4]diazepino[6,7,1-hi]indol-4-one;

3-(2,6,8-Trimethyl-4-oxo-4H-quinazolin-3-yl)-9-nitro-1-phenyl-6,7-dihydro-3H-[1,4]diazepino[6,7,1-hi]indol-4-one;

3-(8-Bromo-2,6-dimethyl-4-oxo-4H-quinazolin-3-yl)-9-nitro-1-phenyl-6,7-dihydro-3H-[1,4]diazepino[6,7,1-hi]indol-4-one;

(3S) 3-(2-Methyl-4-oxo-4H-pyrido[3,4-d]pyrimidin-3-yl)-9-nitro-1-phenyl-6,7-dihydro-3H-[1,4]diazepino[6,7,1-hi]indol-4-one;

5-Chloro-2-methyl-3-(9-nitro-4-oxo-1-phenyl-3,4,6,7-tetrahydro-[1,4]diazepino-[6,7,1-hi]indol-3-yl)-4-oxo-3,4-dihydro-quinazoline.

13. A compound selected from the group consisting of:

(3S) 9-Amino-3-(2-methyl-4-oxo-4H-quinazolin-3-yl)-1-phenyl-6,7-dihydro-3H-[1,4]diazepino[6,7,1-hi]indol-4-one;

3-(9-Amino-4-oxo-1-phenyl-3,4,6,7-tetrahydro-[1,4]diazepino[6,7,1-hi]indol-3-yl)-2-methyl-4-oxo-3,4-dihydro-quinazoline-7-carboxylic acid methyl ester, and its enantiomers;

3-(9-Amino-4-oxo-1-phenyl-3,4,6,7-tetrahydro-[1,4]diazepino[6,7,1-hi]indol-3-yl)-2-methyl-4-oxo-3,4-dihydro-quinazoline-7-carboxylic acid;

9-Amino-3-(2-methyl-4-oxo-4H-quinazolin-3-yl)-1-phenyl-6,7-dihydro-3H-[1,4]diazepino[6,7,1-hi]indol-4-one;

9-Amino-3-(2,5-dimethyl-4-oxo-4H-quinazolin-3-yl)-1-phenyl-6,7-dihydro-3H-[1,4]diazepino[6,7,1-hi]indol-4-one;

9-Amino-3-(2,6-dimethyl-4-oxo-4H-quinazolin-3-yl)-1-phenyl-6,7-dihydro-3H-[1,4]diazepino[6,7,1-hi]indol-4-one;

9-Amino-3-(2,8-dimethyl-4-oxo-4H-quinazolin-3-yl)-1-phenyl-6,7-dihydro-3H-[1,4]diazepino[6,7,1-hi]indol-4-one;

9-Amino-3-(2,6,8-trimethyl-4-oxo-4H-quinazolin-3-yl)-1-phenyl-6,7-dihydro-3H-[1,4]diazepino[6,7,1-hi]indol-4-one;

9-Amino-3-(5-chloro-2-methyl-4-oxo-4H-quinazolin-3-yl)-1-phenyl-6,7-dihydro-3H-[1,4]diazepino[6,7,1-hi]indol-4-one.

14. A compound selected from the aroup consisting of:

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carbonitrile;

9-Methyl-3-[2-methyl-4-oxo-7-(1H-tetrazol-5-yl)-4H-quinazolin-3-yl]-1-phenyl-6,7-dihydro-3H-[1,4]diazepino[6,7,1-hi]indol-4-one;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-N-methylcarboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-N-dimethylcarboxamide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid (2-morpholin-4-yl-ethyl)-amide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid (3-morpholin-4yl-propyl)-amide;

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-(2-amino)-ethylcarboxamide, and the hydrochloride salt thereof;

3-{7-[4-(2-Hydroxy-ethyl)-piperazine-1-carbonyl]-2-methyl-4-oxo-4H-quinazolin-3-yl}-9-methyl-1-phenyl-6,7-dihydro-3H-[1,4]diazepino[6,7,1-hi]indol-4-one, and the hydrochloride salt thereof;

(2S) 6-t-Butoxycarbonylamino-2-{[2-methyl-3-(9-methyl-4-oxo-1-phenyl-3,4,6,7-tetrahydro-[1,4]diazepino[6,7,1-hi]indol-3-yl)-4-oxo-3,4-dihydro-quinazolin-7-carbonyl]-amino}-hexanoic acid methyl ester;

(2S) 6-Amino-2-{[2-methyl-3-(9-methyl-4-oxo-1-phenyl-3,4,6,7-tetrahydro-[1,4]diazepino[6,7,1-hi]indol-3-yl)-4-oxo-3,4-dihydro-quinazolin-7-carbonyl]-amino}-hexanoic acid methyl ester.

15. A compound selected from the group consisting of:

2-Methyl-3-(9-methyl-4-oxo-1-phenyl-3,4,6,7-tetrahydro-[1,4]diazepino[6,7,1-hi]indol-3-yl)-4-oxo-3,4-dihydro-quinazoline-7-carboxylic acid pentafluorophenyl ester;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-tyrosine;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-alanine;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-phenylalanine;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-glycine;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-leucine;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-aspartic acid;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-glutamic acid;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-lysine;

2 {[2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carbonyl]-amino}-3-phenyl-(L)-propionic acid ethyl ester;

N-(2-Methyl-3-(9-methyl-4-oxo-1-phenyl-3,4,6,7-tetrahydro-[1,4]diazepino-[6,7,1-hi]indol-3-yl)-4-oxo-3,4-dihydro-quinazoline-7-carboxyl-)-proline.

16. Process for the preparation of the compounds (I) according to claim 1 which consists:

i)—for preparing optically active compounds (I)

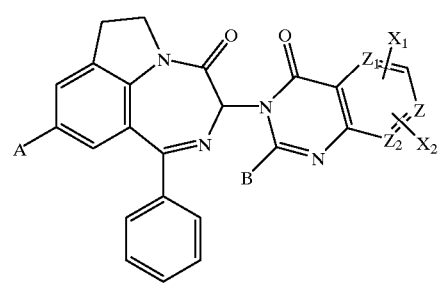

in reacting an optically active amine (IVd)

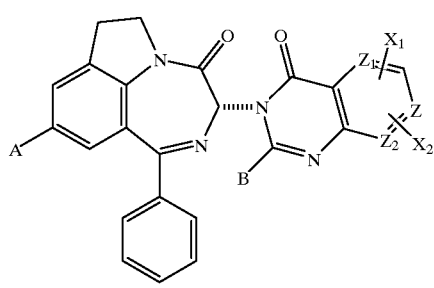

with an ortho-ester B—C(OMe)$_3$, to obtain the imine derivative (Vd)

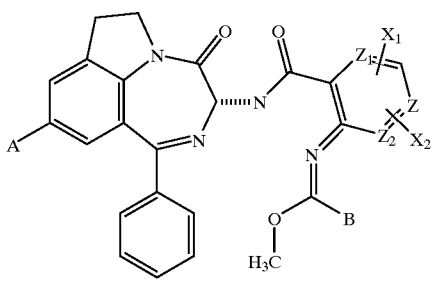

(Vd)

and cyclizing this intermediate in a neutral solvent with an acid catalyst;

ii)—for preparing compounds (I) in which A and Z have the designations of (I), B the designations of (I) except for those comprising a carboxylic acid function, and $X_1$ and $X_2$ the meanings of (I) except for those comprising a reactive hydroxyl function, in reacting an intermediate aminodiazepinoindolone (II) of formula

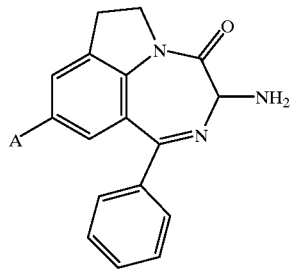

(II)

in which A has the designations of (I), with an aromatic 2-amido acid (IIIa) of formula

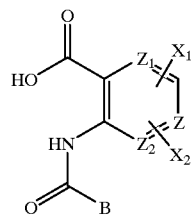

(IIIa)

in which B, Z, $Z_1$, $Z_2$, $X_1$ and $X_2$ have the designations defined above, or
with a 4-oxo-4H-oxazine (IIIb) of formula

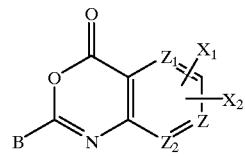

(IIIb)

in which B, Z, $X_1$ and $X_2$ have the designations defined above, or
with a mixture comprising from 95 to 5% by weight of an intermediate (IIIa) with from 5 to 95% of an intermediate (IIIb), in which B, Z, $X_1$ and $X_2$, which are identical for both intermediates, have the designations defined above, the intermediates (IIIa) and (hIb) being isolated or otherwise after their preparation by N-acylation and then, where appropriate, cyclization of an aromatic 2-amino acid (III) of formula

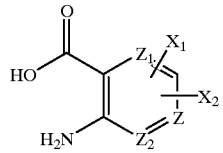

(III)

with 1,1,1-trimethoxyethane, or with a reactant $(B—CO)_nW$ in which B has the designations of (I) except for those comprising a carboxylic acid fuinction, and W is halogen, in particular chlorine or bromine, when n has the value 1, or alternatively is oxygen when n has the value 2; or finally
with an imine of formula (IIIc):

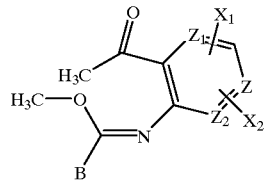

(IIIc)

and in cyclizing the intermediate obtained; the imine (IIIc) is first obtained by condensation of an aromatic amine of formula (IVc)

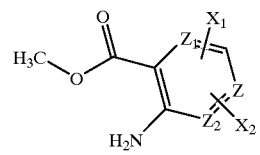

(IVc)

with a 1,1,1-trimethoxy-alkane;

iii)—for preparing compounds (I) in which B and Z have the designations of (I), A the designations of (I) except for amino and $X_1$ or $X_2$ the meanings of (I) except for those comprising a reactive hydroxyl function, in N-acylating an intermediate diazepinoindolone (IV) of formula

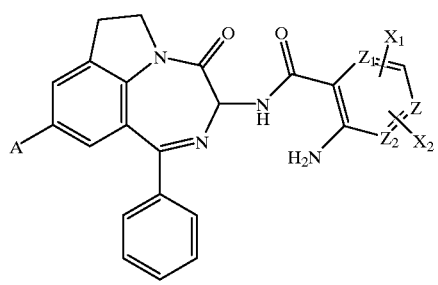

in which A, Z, $X_1$ and $X_2$ have the designations defined above, with a reactant $(B—CO)_nW$ defined above in which B has the meanings designated above, to obtain an intermediate (V) of formula

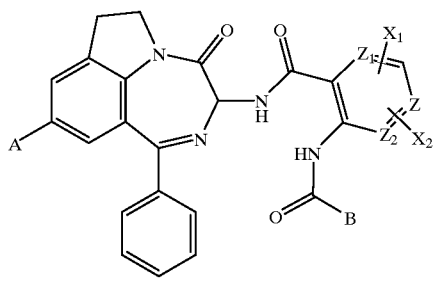

which is cyclized to a diazepinoindolone (I);

iv)—for preparing a compound (I) in which A is amino and where B, Z, $X_1$ and $X_2$ have the meanings of (I), in reducing with sodium sulfide or a metal chloride, a compound (I) in which A is nitro; or in hydrolyzing in an acid or alkaline medium a compound (I) comprising an amide (—CO—N<) or ester (—CO—O— or —O—CO—) function, to obtain a corresponding acid or alcohol compound (I);

in reducing with a complex metal hydride or organometallic hydride a compound (I) comprising an acid (—CO—OH) or ester (—CO—O—) function, to obtain a corresponding alcohol compound (I);

in carrying out the hydrogenolysis in the presence of a metal catalyst of a compound (I) comprising an ether, in particular a benzyl ether (—O—$CH_2$–$C_6H_5$), function, to obtain a corresponding alcohol compound (I);

in esterifying or transesterifying with an alcohol a compound (I) having an acid (—$CO_2$H) or ester (—CO—O—) function, to obtain a compound (I) ester of said alcohol; or in amidating with ammonia or a primary or secondary amine a compound (I) comprising an acid (—CO—OH) or ester (—CO—O) function, to obtain a corresponding primary, secondary or tertiary amide compound (I).

17. A method of treating a patient suffering from asthma, atopic dermatitis or rheumatoid arthritis comprising administering a therapeutically effective amount of a compound according to claim 1.

18. A method of treating a patient suffering from an inflammatory bowel disease, ulcerative colitis or Crohn's disease comprising administering a therapeutically effective amount of a compound according to claim 1.

19. A method of treating a patient suffering from primary or secondary pulmonary hypertension comprising administering a therapeutically effective amount of a compound according to claim 1.

20. A method of treating a patient suffering from hepatic failure comprising administering a therapeutically effective amount of a compound according to claim 1.

21. A method of treating a patient suffering from bone loss comprising administering a therapeutically effective amount of a compound according to claim 1.

22. A method of treating a patient suffering from septic shock comprising administering a therapeutically effective amount of a compound according to claim 1.

23. A method of treating a patient suffering from multiple sclerosis comprising administering a therapeutically effective amount of a compound according to claim 1.

24. A pharmaceutical composition comprising a compound of one of claims 1 to 15 together with a pharmaceutically acceptable carrier, diluent or excipient therefor.

* * * * *